US011976099B2

(12) United States Patent
Papo et al.

(10) Patent No.: US 11,976,099 B2
(45) Date of Patent: *May 7, 2024

(54) COMPOSITIONS AND METHODS FOR TREATMENT OF BONE ASSOCIATED DISEASES

(71) Applicants: THE NATIONAL INSTITUTE FOR BIOTECHNOLOGY IN THE NEGEV LTD., Beer Sheva (IL); B. G. NEGEV TECHNOLOGIES AND APPLICATIONS LTD., AT BEN-GURION UNIVERSITY, Beer Sheva (IL)

(72) Inventors: Niv Papo, Raanana (IL); Noam Levaot, Lehavim (IL); Yuval Zur, Tel Aviv (IL); Lior Rosenfeld, Modiin (IL)

(73) Assignees: THE NATIONAL INSTITUTE FOR BIOTECHNOLOGY IN THE NEGEV LTD., Beer Sheva (IL); B. G. NEGEV TECHNOLOGIES AND APPLICATIONS LTD., AT BEN-GURION UNIVERSITY, Beer Sheva (IL)

( * ) Notice: Subject to any disclaimer, the term of this patent is extended or adjusted under 35 U.S.C. 154(b) by 79 days.

This patent is subject to a terminal disclaimer.

(21) Appl. No.: 17/393,593

(22) Filed: Aug. 4, 2021

(65) Prior Publication Data

US 2021/0403514 A1 Dec. 30, 2021

Related U.S. Application Data

(63) Continuation of application No. 16/326,456, filed as application No. PCT/IL2017/050921 on Aug. 17, 2017, now Pat. No. 11,098,091.

(30) Foreign Application Priority Data

Aug. 18, 2016 (IL) .......................................... 247369

(51) Int. Cl.

| | |
|---|---|
| ***C07K 14/435*** | (2006.01) |
| ***A61K 38/00*** | (2006.01) |
| ***A61K 38/19*** | (2006.01) |
| ***A61P 19/00*** | (2006.01) |
| ***C07K 14/52*** | (2006.01) |
| ***C07K 14/535*** | (2006.01) |
| ***C12N 15/11*** | (2006.01) |
| *C07K 14/53* | (2006.01) |

(52) U.S. Cl.

CPC ............ *C07K 14/435* (2013.01); *A61K 38/19* (2013.01); *A61P 19/00* (2018.01); *C07K 14/52* (2013.01); *C07K 14/535* (2013.01); *C12N 15/11* (2013.01); *A61K 38/00* (2013.01); *A61K 38/193* (2013.01); *C07K 14/53* (2013.01)

(58) Field of Classification Search

None

See application file for complete search history.

(56) References Cited

U.S. PATENT DOCUMENTS

| | | | | |
|---|---|---|---|---|
| 5,288,931 | A * | 2/1994 | Chang .................. | C07K 1/1133 530/825 |
| 5,464,764 | A | 11/1995 | Capecchi et al. | |
| 5,487,992 | A | 1/1996 | Capecchi et al. | |
| 5,932,447 | A | 8/1999 | Siegall | |
| 7,112,660 | B1 * | 9/2006 | Domingues ............. | A61P 37/08 424/85.2 |
| 11,098,091 | B2 * | 8/2021 | Papo .................... | C07K 14/435 |
| 2003/0045474 | A1 * | 3/2003 | Sailer ................. | A61K 38/1875 514/8.8 |
| 2014/0154743 | A1 * | 6/2014 | Levy .............. | C12Y 502/01008 435/69.6 |
| 2015/0037889 | A1 | 2/2015 | Cochran et al. | |
| 2021/0403514 | A1 * | 12/2021 | Papo ....................... | A61P 19/00 |

FOREIGN PATENT DOCUMENTS

WO 2007016285 A2 2/2007

OTHER PUBLICATIONS

Tokuriki et al., 2009, Curr. Opin. Struc. Biol. 19:596-604.*

Bhattacharya et al. (2017, PLoS ONE 12(3): e0171355, https://doi.org/10.1371/journal.pone.0171355).*

Alaoui-Ismaili (2009, Cytokine Growth Factor Rev. 20(5-6):501-7).*

Guo et al. (2004, PNAS USA 101(25):9205-10).*

Ulloa-Aguirre et al. (2004, Traffic 5:821-837).*

Bernier et al. (2004, Curr. Opin. Pharmacol. 4:528-533).*

Otwinowski et al. (1997), Processing of X-Ray Diffraction Data Collected in Oscillation Mode, Processing of X-Ray Diffraction Data, Methods Enzymo. 276: 307-326. Retrieved Oct. 14, 2021; PMID: 27754618.

McCoy et al., Phaser crystallographic software, Journal of Applied Crystallography (2007) 40, 658-674. Retrieved Oct. 14, 2021; doi:10.1107/S0021889807021206.

Winn et al., Overview of the CCP4 suite and current developments, Biological Crystallography, (2011) Sect. D 67, 235-242. Retrieved Oct. 14, 2021; doi:10.1107/S0907444910045749.

Emsley et al., Coot: model-building tools for molecular graphics, Biological Crystallography (2004) 60, 2126-2132. Retrieved Oct. 14, 2021; doi:10.1107/S0907444904019158.

Adams et al., Phenix: a comprehensive Python-based system for macromolecular structure solution, Biological Crystallography (2010) 66, 213-221. Retrieved Oct. 14, 2021; doi:10.1107/S0907444909052925.

(Continued)

*Primary Examiner* — Elizabeth C. Kemmerer
(74) *Attorney, Agent, or Firm* — The Roy Gross Law Firm, LLC; Roy Gross

(57) ABSTRACT

Mutant M-CSF protein, comprising $\alpha_v\beta_3$ integrin binding motif and pharmaceutical compositions comprising same, are provided. Further, use of the composition for the treatment and or prevention of diseases associated with increased bone resorption are provided.

8 Claims, 39 Drawing Sheets

Specification includes a Sequence Listing.

(56) References Cited

OTHER PUBLICATIONS

Kosloff et al., Integrating energy calculations with functional assays to decipher the specificity of G protein-RGS protein interactions, 2011; Nat. Struct. Mol. Biol. 18, 846-853. Retrieved Oct. 14, 2021; doi:10.1038/nsmb.2068.

Sheinerman et al., Sequence, Structure and Energetic Determinants of Phosphopeptide Selectivity of SH2 Domains, J. Mol. Biol. (2003) 334, 823-841. Retrieved Oct. 14, 2021; doi:10.1016/j.jmb.2003.09.075.

Rosenfeld et al. (2015) Macrophage Colony-stimulating Factor (M-CSF) and Its Receptor c-FMS Combinatorial and Computational Approaches to Identify Interactions of Macrophage Colony-stimulating Factor (M-CSF) and Its Receptor c-FMS. J. Biol. Chem. 2015, 290:26180-26193. Retrieved Oct. 14, 2021; doi: 10.1074/jbc.M115.671271.

Tuukkanen et al., Progress in small-angle scattering from biological solutions at high-brilliance synchrotrons, IUCrJ (2017). 4, 518-528. Retrieved Oct. 14, 2021 from: https://doi.org/10.1107/S2052252517008740.

Svergun et al., Determination of Domain Structure of Proteins from X-Ray Solution Scattering, (1992) . J. Appl. Crystallogr. 25, 495-503. Retrieved Oct. 14, 2021; doi: 10.1016/S0006-3495(01)76260-1.

Volkov et al., Uniqueness of ab initio shape determination in small-angle scattering, (2003) J. Appl. Crystallogr. 36, 860-864. Retrieved Oct. 14, 2021 from: https://doi.org/10.1107/S0021889803000268.

Levaot et al., 3BP2-deficient mice are osteoporotic with impaired osteoblast and osteoclast functions, J Clin Invest. 2011;121(8):3244-3257. Retrieved Oct. 14, 2021 from: https://doi.org/10.1172/JCI45843.

Elegheert et al., Allosteric competitive inactivation of hematopoietic CSF-1 signaling by the viral decoy receptor BARF1, Nat Struct Mol Biol, 2012. 19(9): p. 938-47. Retrieved Oct. 14, 2021; doi:10.1038/nsmb.2367.

Gramoun et al., Effects of Vitaxin, a Novel Therapeutic in Trial for Metastatic Bone Tumors, on Osteoclast Functions In Vitro, Journal of Cellular Biochemistry 102:341-352 (2007). Retrieved Oct. 14, 2021; DOI 10.1002/jcb.21296.

Jung et al., DICAM Inhibits Osteoclast Differentiation Through, Attenuation of the Integrin aVb3 Pathway, Journal of Bone and Mineral Research, vol. 27, No. 9, Sep. 2012, pp. 2024-2034. Retrieved Oct. 14, 2021; DOI: 10.1002/jbmr.1632.

Zanella et al., Synthesis, Characterization, and Biological Evaluation of aDual-Action Ligand Targeting avb Integrin and VEGF, ChemistryOpen 2015, 4(5), 633-641. Retrieved Oct. 14, 2021; DOI: 10.1002/open.201500062.

Faccio et al., "c-Fms and the alphavbeta3 integrin collaborate during osteoclast differentiation", Journal of Clinical Investigation, vol. 111, No. 5, 2003. Retrieved Oct. 14, 2021 from: https://doi.org/10.1172/JCI16924.

Database Geneseq [Online], "Human macrophage colony stimulating factor beta (M-CSFbeta) protein.", XP002797194, Retrieved from EBI accession No. GSP: AER59047, 2007.

Zur et al., "A dual-specific macrophage colony-stimulating factor antagonist of c-FMS and [alpha]v[beta]3 integrin for osteoporosis therapy", PLOS Biology, vol. 16, No. 8, 2018. https://doi.org/10.1371/journal.pbio.2002979.

Tokuriki et al. (2017). Stability effects of mutations and protein evolvability. Current Opinion in Structural Biology, 19 (5), 596-604. Retrieved Oct. 14, 2021; doi:10.1016/j.sbi.2009.08.003 Retrieved Oct. 14, 2021; DOI 10.1016/j.sbi.2009.08.003.

Bhattacharya et al. (2017). : Impact of genetic variation on three dimensional structure and function of proteins.PLoS ONE 12(3): e0171355. Retrieved Oct. 14, 2021 from: https://doi.org/10.1371/journal.pone.0171355.

Alaoui-Ismali et al. (2009). Design of second generation therapeutic recombinant bone morphogenetic proteins. Cytokine & Growth Factor Reviews, 20 (5-6), 501-507. Retrieved Oct. 14, 2021; doi:10.1016/j.cytogfr.2009.10.

Guo et al. (2004). Protein tolerance to random amino acid change. PNAS, Jun. 22, 2004 101(25) 9205-9210; Retrieved Oct. 14, 2021 from: https://doi.org/10.1073/pnas.0403255101.

Ulloa-Aguirre et al.(2004). Pharmacological Rescue of Conformationally-Defective Proteins: Implications for treatment of human disease. Traffic, vol. 5, 821-837. Retrieved Oct. 14, 2021; doi: 10.1111/j.1600-0854.2004.00232.x.

Bernier et al. (2004). Pharmacological chaperone action on G-protein-coupled receptors. Current Opinion in Pharmacology, 4(5), pp. 528-533. Retrieved Oct. 14, 2021 from: https://doi.org/10.1016/j.coph.2004.08.001.

PCT International Search Report for International Application No. PCT/IL2017/050921, dated Nov. 29, 2017, 5pp.

PCT Written Opinion for International Application No. PCT/IL2017/050921, dated Nov. 29, 2017, 6pp.

PCT International Preliminary Report on Patentability for International Application No. PCT/IL2017/050921, completed Nov. 28, 2017, 7pp.

Wiktor-Jedrzejczak, W. et al. (1990) Total absence of colony-stimulating factor 1 in the macrophage-deficient osteopetrotic (op/op) mouse. Proc. Natl. Acad. Sci. U.S.A. 87, 4828-4832.

Yoshida, H. et al. (1990) The murine mutation osteopetrosis is in the coding region of the macrophage colony stimulating factor gene. Nature 345, 442-444.

Dai, X. M. et al. (2002) Targeted disruption of the mouse CSF-1 receptor gene results in osteopetrosis, mononuclear phagocyte deficiency, increased primitive progenitor cell frequencies and reproductive defects. Blood 99, 111-120.

GeneBank: BAD92189.1 retreived Dec. 14, 2021 <https://www.ncbi.nlm .nih.gov/protein/BAD92189.1?report=genbank&log$=protalign& blast_rank=1&RID=VGYMKP6S013>.

* cited by examiner

*

EEVSEYCSHMIGSGHLQSLQRLIDSQMETSCQITFEFVDQEQLKDPVCYLKKAFLL
VQDIMEDTMRFRDNTPNAIAIVQLQELSLRLKSCFTKDYEEHDKACVRTFYETPLQ
LLEKVKNVFNETKNLLDKDWNIFSKNCNNSFAECSSQGHERQSEGS (SEQ ID NO: 2)

FIG. 1A

EEVSEYCSHMIGSGHLQSLQRLIDXXXRGDXXXITFEFVDQEQLKDPVCYLKKAFL
LVQDIMEDTMRFRDNTPNAIAIVQLQELSLRLKSCFTKDYEEHDKACVRTFYETPL
QLLEKVKNVFNETKNLLDKDWNIFSKNCNNSFAECSSQGHERQSEGS (SEQ ID NO: 19)

FIG. 1B

EEVSEYCSHMIGSGHLQSLQRLIDSQMETSSQITFEFVDQEQLKDPVCYLKKAFLL
VQDIMEDXXXRGDXXXPNAIAIVQLQELSLRLKSCFTKDYEEHDKACVRTFYETPL
QLLEKVKNVFNETKNLLDKDWNIFSKNCNNSFAECSSQGHERQSEGS

FIG. 1C

| Clone | Sequence |
|---|---|
| 4.22 (library 1) | QTS *RGD* SPS |
| 4.24 (library 2) | EPV *RGD* NIN |
| 5.6 (library 1) | TYP *RGD* MCS |

FIG. 1D

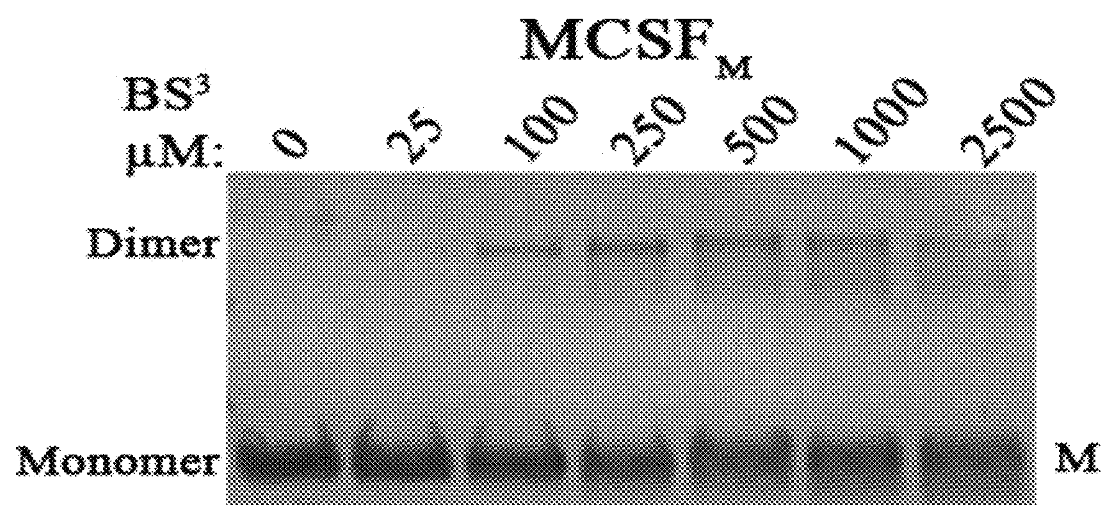
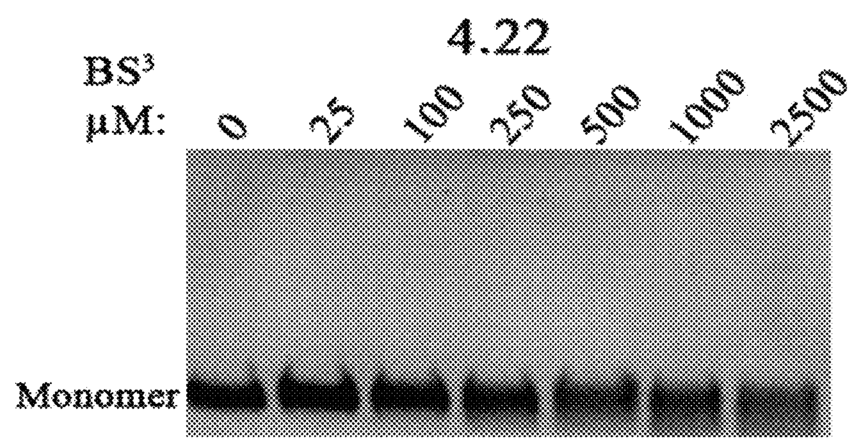
FIG. 8

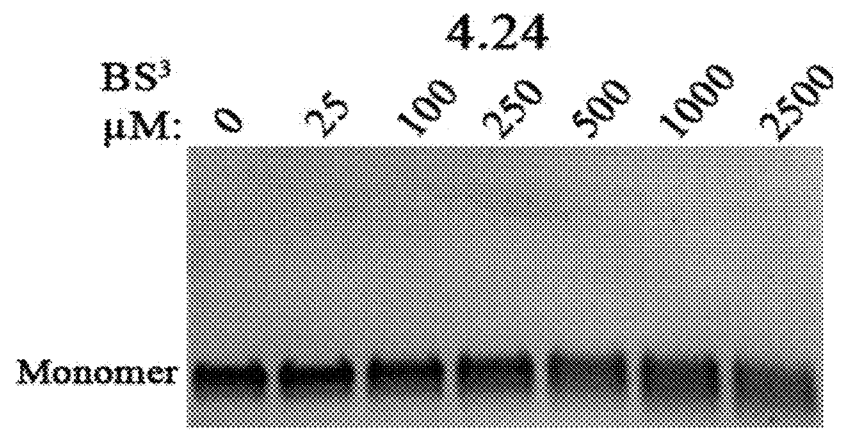
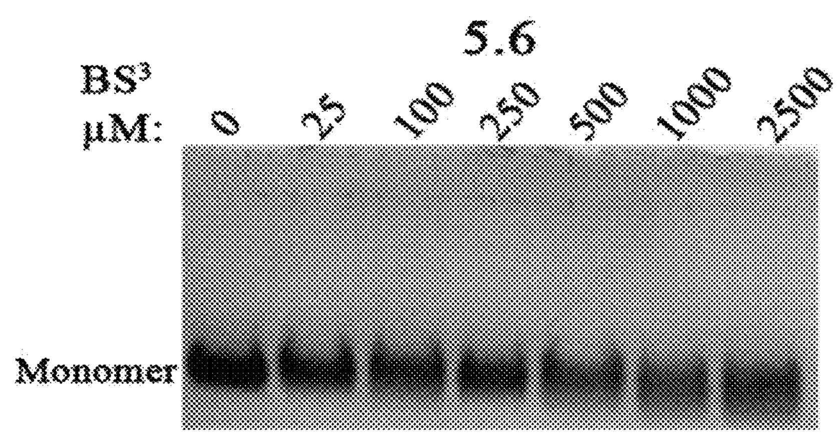
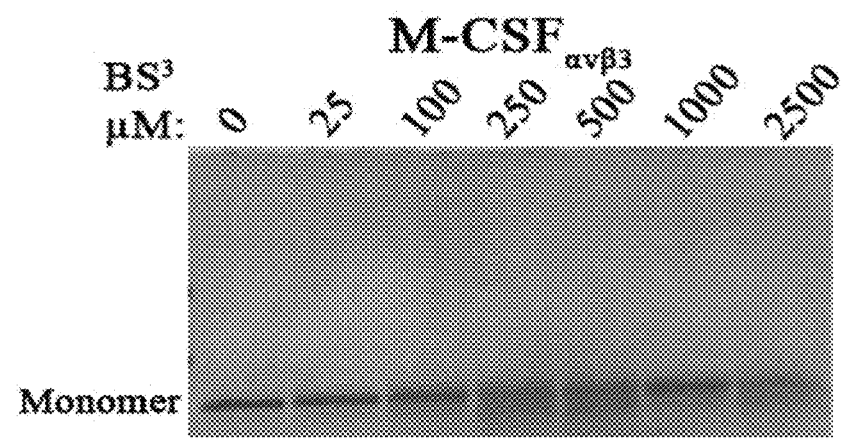
FIG 8 Continued

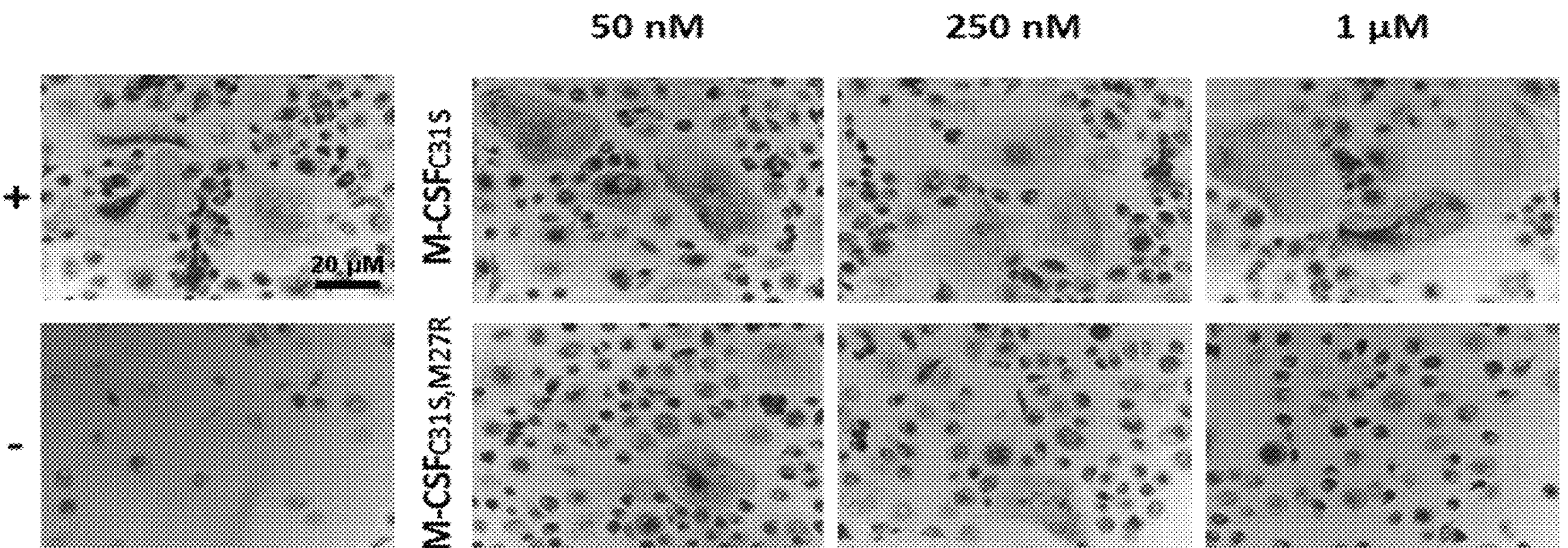
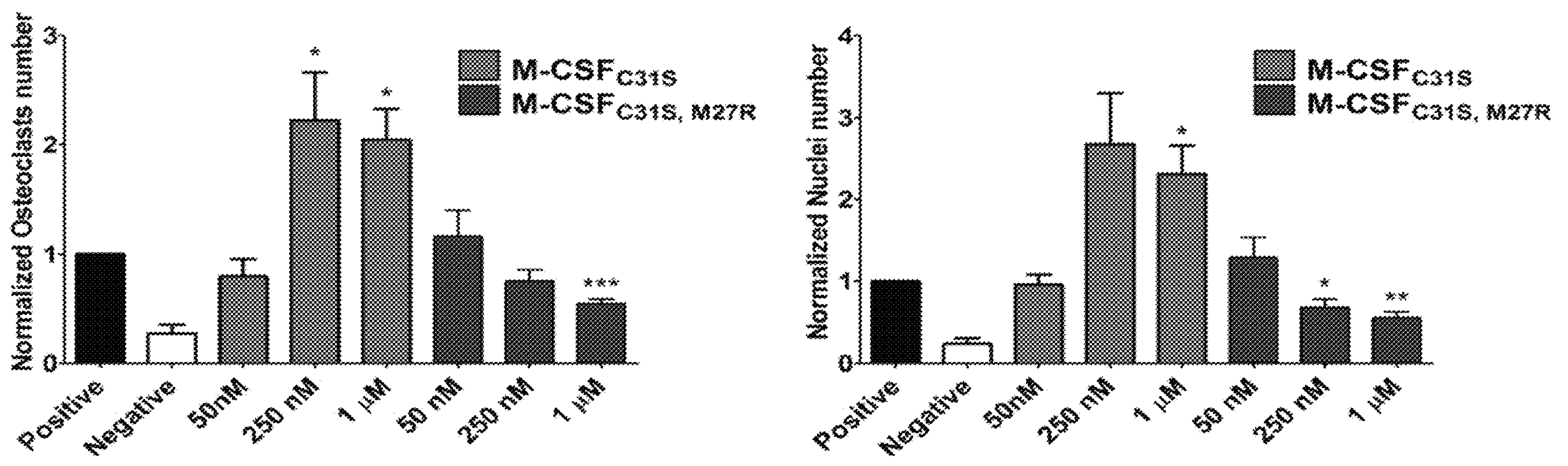
FIG. 19B

FIG. 20B

COMPOSITIONS AND METHODS FOR TREATMENT OF BONE ASSOCIATED DISEASES

CROSS-REFERENCE TO RELATED APPLICATIONS

This application is a continuation of U.S. patent application Ser. No. 16/326,456 filed Feb. 19, 2019, now U.S. Pat. No. 11,098,091, which is a national phase of PCT Patent Application No. PCT/IL2017/050921 filed Aug. 17, 2017, which claims the benefit of priority from IL Patent Application No. 247369 filed Aug. 18, 2016, entitled "MODIFIED M-CSF POLYPEPTIDES AND USE THEREOF", incorporated herein by reference in their entirety.

REFERENCE TO AN ELECTRONIC SEQUENCE LISTING

The contents of the electronic sequence listing (NIBN-P-016-US1-SQL.txt; size: 24,768 bytes; and date of creation: Aug. 19, 2023) is herein incorporated by reference in its entirety.

FIELD OF INVENTION

The present invention is directed to, inter alia, modified polypeptides and use thereof such as in the therapy of bone associated diseases.

BACKGROUND OF THE INVENTION

Osteoporosis, a common chronic skeletal disorder in both women and men beyond the age of 50, is the underlying cause of more than 8.9 million fractures annually worldwide, with the obvious resulting social and economic costs. The drugs initially used for the management of osteoporosis in women were based on estrogens, but long-term administration of these drugs was associated with increased risk of breast cancer, cardiovascular disease, and dementia. To date, the most commonly prescribed drugs for osteoporosis are bisphosphonates, but these drugs, too, have nonspecific adverse side effects such as gastrointestinal toxicity, renal toxicity, hypercalcemia, osteonecrosis of the jaw and more. Thus, there is a pressing need for new efficient and highly specific drugs for the management of osteoporosis.

Excessive bone resorption by osteoclasts is central to the pathogenesis of osteoporosis. Osteoclasts differentiate from cells of the monocyte/macrophage lineage upon stimulation of two essential factors, the monocyte/macrophage colony stimulating factor (M-CSF) and the receptor for activation of the NF-κB ligand (RANKL). In recent years, antibodies targeting M-CSF and RANKL have proved efficient for the inhibition of osteoclast differentiation and hence for the treatment of osteoporosis, but the expression of these ligands on cells other than osteoclasts has raised concerns as to their safety.

The importance of M-CSF and its receptor c-FMS in osteoclast function has been previously illustrated in a study showing that both M-CSF- and c-FMS-deficient mice suffer from retarded skeletal growth and osteopetrosis. Likewise, αvβ3 integrin is essential for osteoclast functioning; interaction of αvβ3 integrin with the bone matrix induces cytoskeleton organization that polarizes the osteoclast's resorptive machinery to the bone-cell interface, where it creates an isolated resorptive compartment consisting of an actin ring surrounding a ruffled border. This is reflected by the observation that integrin β3 knockout mice have increased bone mass due to a functional defect in osteoclasts.

Interestingly, in addition to the distinctive roles of c-FMS and αvβ3 integrin in osteoclast activity, it has been shown that the two factors play a cooperative role in bone resorption. M-CSF signaling regulates bone resorption by cross-talk through its receptor c-FMS, with signaling being activated by αvβ3 integrin. c-FMS plays a significant role in regulating bone resorption by collaborating with αvβ3 integrin in osteoclast cytoskeleton re-arrangement, as both factors stimulate the same c-Src-initiated signaling complex. Finally, c-FMS alters the conformation of αvβ3 from a low- to a high-affinity state, and it activates Rac in an integrin-αvβ3-dependent manner. Importantly, it was shown that both c-FMS and αvβ3 integrin co-localize to the osteoclast cytoskeleton suggesting that the crosstalk between these receptors takes place at the same cellular sites. Thus, the functional and spatial coupling of c-FMS and αvβ3 integrin in osteoclast differentiation and function together with the exclusive presentation of both of these receptors suggest that an antagonist that binds simultaneously to both of these target receptors could serve as a highly specific and effective anti-resorptive drug.

Some work on targeting individually c-FMS and αvβ3 integrin for osteoporosis therapy has already been started, but it has not developed towards clinical application. For example, several studies utilizing two anti c-FMS antibodies, designated AFS98 and M279, and a recently developed c-FMS humanized anti c-FMS monoclonal antibody (mAb) addressed the functional role of M-CSF signaling in cancer pathology but their efficacy in the inhibition of osteoclast activity in vivo has not been explored. An additional—and perhaps more important—problem is that the development of low-molecular-weight kinase domain inhibitors that target c-FMS is particularly challenging in light of factors such as toxicity, drug resistance, or off-target effects.

Recent research has focused on antibodies to αvβ3 integrin, peptidomimetics of the Arg-Gly-Asp ("RGD") tripeptide motif, and small-molecule αvβ3 integrin antagonists, which have been shown to be efficacious in in vitro and in vivo models of bone resorption, indicating that inhibitors of αvβ3 integrin would be suitable agents for the treatment of osteoporosis.

SUMMARY OF THE INVENTION

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

According to one aspect, there is provided a polypeptide comprising an amino acid sequence having at least 90% homology to SEQ ID NO: 1, said polypeptide comprising at least one mutation selected from: mutation of the methionine residue at position 27 of SEQ ID NO: 1, or substitution of amino acids 25-32 or amino acids 64-71 of SEQ ID NO: 1 with an RGD motif, said RGD motif comprises the amino acid sequence as set forth in SEQ ID NO: 6.

According to another embodiment, said mutation of the methionine residue at position 27 of SEQ ID NO: 1, is a substitution to an amino acid selected from arginine (Arg), histidine (His) or lysine (Lys). According to another embodiment, said polypeptide comprises the amino acid sequence as set forth in SEQ ID NO: 11.

According to another embodiment, said mutation of the methionine residue at position 27 of SEQ ID NO: 1, is a substitution to arginine (Arg). According to another embodiment, said polypeptide comprises the amino acid sequence as set forth in SEQ ID NO: 15.

According to another embodiment, said RGD motif comprises at least 9 amino acid residues. According to another embodiment, said RGD motif comprises the amino acid sequence as set forth in SEQ ID NO: 7 (XXXRGDXXX), wherein X is, independently, any amino acid. According to another embodiment, said RGD motif is selected from the group consisting of: SEQ ID NO: 8 (QTSRGDSPS), SEQ ID NO: 9 (TYPRGDMCS), and SEQ ID NO: 10 (EPVRGDNIN).

According to another embodiment, said polypeptide comprises a substitution of amino acids 25-32 of SEQ ID NO: 1 with said RGD motif. According to another embodiment, said RGD motif is selected from the group consisting of: SEQ ID NO: 8 (QTSRGDSPS), and SEQ ID NO: 9 (TYPRGDMCS).

According to another embodiment, said polypeptide comprises a substitution of amino acids 64-71 of SEQ ID NO: 1 with said RGD motif. According to another embodiment, said RGD motif comprises the amino acid sequence as set forth in SEQ ID NO: 10 (EPVRGDNIN).

According to another embodiment, said polypeptide is incapable of forming homodimers. According to another embodiment, said polypeptide binds c-FMS and $\alpha_v\beta_3$ integrin.

According to another embodiment, said polypeptide comprises an amino acid sequence having at least 97% homology to the amino acid sequence as set forth in formula I (EEVSEYCSHMIGSGHLQSLQRLID(SQMETSSQ)$_b$(X$_1$X$_2$X$_3$RGDX$_4$X$_5$S)$_{(1-b)}$ITFEFVDQEQLKDPVCYLKKAFLLVQDIMED(TMRFRDNT)$_{(1-b)}$(EPVRGDNIN)$_b$PNAIAIVQLQELSLRLKSCFTKDYEEHDKACVRTFYETPLQLLEKVKNVFNETKNLLDKDWNIFSKNCNNSFAECSS), wherein b is an integer selected from 0 and 1, and wherein: $X_1$ is Q or T, $X_2$ is T or Y, $X_3$ is S or P, $X_4$ is S or M, and $X_5$ is P or C, wherein the polypeptide is incapable of forming homodimers, and wherein said mutant binds c-FMS and $\alpha_v\beta_3$ integrin.

According to another embodiment, said polypeptide comprises an amino acid sequence selected from the group consisting of: SEQ ID NO: 12, SEQ ID NO: 13, SEQ ID NO: 14, SEQ ID NO: 16, and SEQ ID NO: 17.

According to another aspect, there is provided a polypeptide comprising the amino acid sequence as set forth in formula I:

(EEVSEYCSHMIGSGHLQSLQRLID(SQMETSSQ)$_b$(X$_1$X$_2$X$_3$RGDX$_4$X$_5$S)$_{(1-b)}$ITFEFVDQEQLKDPVCYLKKAFLLVQDIMED(TMRFRDNT)$_{(1-b)}$(EPVRGDNIN)$_b$PNAIAIVQLQELSLRLKSCFTKDYEEHDKACVRTFYETPLQLLEKVKNVFNETKNLLDKDWNIFSKNCNNSFAECSS), wherein b is an integer selected from 0 and 1, and wherein: $X_1$ is Q or T, $X_2$ is T or Y, $X_3$ is S or P, $X_4$ is S or M, and $X_5$ is P or C.

According to another aspect, there is provided a polypeptide comprising an amino acid sequence selected from the group consisting of: SEQ ID NO: 11, SEQ ID NO: 12, SEQ ID NO: 13, SEQ ID NO: 14, SEQ ID NO: 16 and SEQ ID NO: 17.

According to another aspect, there is provided an isolated nucleic acid molecule encoding the polypeptide of the present invention. According to another aspect, there is provided an expression vector comprising the nucleic acid of the present invention. According to another aspect, there is provided a cell transformed or transfected with the expression vector of the present invention.

According to another aspect, there is provided a pharmaceutical composition comprising the polypeptide of the present invention and a pharmaceutical acceptable carrier. In some embodiments, said composition is for inhibition or reduction of osteoclast activity.

According to another aspect, there is provided a pharmaceutical composition comprising a therapeutically effective amount of the polypeptide of the present invention, and a pharmaceutical acceptable carrier, for use in the treatment or prevention of a disease associated with unregulated osteoclast activity in a subject in need thereof.

According to another aspect, there is provided use of a pharmaceutical composition comprising a therapeutically effective amount of the polypeptide of the present invention, and a pharmaceutical acceptable carrier, in the preparation of a medicament for the treatment or prevention of a disease associated with unregulated osteoclast activity in a subject in need thereof.

According to another aspect, there is provided a method for treating a disease associated with increased bone resorption in a subject in need thereof, the method comprising the step of administering to said subject a pharmaceutical composition comprising the polypeptide the present invention and a pharmaceutical acceptable carrier, thereby treating a disease associated with increased bone resorption in a subject in need thereof.

In some embodiments, said disease is associated with increased bone resorption. In some embodiments, said disease associated with increased bone resorption is osteoporosis.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIGS. 1A-1D demonstrate amino acid sequences of M-CSF, M-CSF$_{RGD}$ libraries and the three M-CSF$_{RGD}$ variants that were chosen after affinity maturation process. FIGS. 1A-1C show amino acids sequences of: (1A) M-CSF with C31 (SEQ ID NO: 2) required for dimerization marked by asterisk, the two flexible loops in the dimerization interface are underlined with one line (loop AB, residues 25-32) and with two lines (loop 3, residues 64-71), (1B) M-CSF$_{RGD}$ library 1 (SEQ ID NO: 19), where residues 25-32 were replaced with an RGD motif having three random amino acids on each side, and (1C) M-CSF$_{RGD}$ library 2 (SEQ ID NO: 20), where residues 64-71 where replaced with an RGD motif with three random amino acids on each side and C31 was replaced with serine to inhibit disulfide-linked homo-dimerization; FIG. 1D is a table presenting sequences of the mutated loop of the three M-CSF$_{RGD}$ clones that were selected after four (4.22 and 4.24) and five (5.6) rounds of the affinity maturation process;

FIG. 8 shows photographs of gels presenting monomers and dimers of the purified variants M-CSF$_{\alpha v\beta 3}$ (4.22, 4.24, 5.6), M-CSF$_{\alpha v\beta 3}$, and M-CFS$_{M}$ following incubation with increasing concentrations of the cross linker $BS^3$;

(FIG. 12A) Cells were fixed and stained for Tartrate-resistant acid phosphatase (TRAP). (FIGS. 12B-D) Cells were examined for: (FIG. 12B) number of mature osteoclasts, (FIG. 12C) bone marrow monocytes. Results were normalized to the positive control.

FIG. 14A depicts the solved X-ray structure of the dimeric M-CSF$_{C31S}$ mutant, shown in ribbon diagram with S31 visualized as sticks. FIG. 14B depicts a close-up of the C31-C31 disulfide bond in the wild-type M-CSF structure (PDB ID 3UF2), visualized as spheres and colored by atom. The structure is rotated 90° about X in relation to the M-CSF$_{C31S}$ mutant shown in 14A. FIG. 14C is an overlay of the M-CSF$_{C31S}$ mutant structure on the M-CSF wild-type structure, with the two C31 residues from the latter shown as spheres. FIG. 14D is a close-up of the S31 residues in the M-CSF$_{C31S}$ mutant dimer, visualized as in 14B.

FIG. 15A. M-CSF$_{C31S}$ residues calculated to contribute significantly to interactions across the dimer interface (see Table 1), shown as sticks and colored by the type of their energy contribution as follows: magenta (polar/electrostatic contribution from the side chain+a non-polar contribution), cyan (polar/electrostatic contribution from the main chain+a non-polar contribution), green (non-polar contribution only). The opposing monomer is shown as surface representation colored wheat. FIG. 15B is similar to 15A, rotated 180° about X. FIG. 15C illustrates the orientation of Q26 and M27, which contribute significantly and were deemed to be particularly influential on dimer formation and therefore chosen for further mutagenesis, shown as sticks (Q26 from both monomers and one of the M27 residues) and spheres (the M27 residue from the opposing monomer).

FIG. 16A is an SDS-PAGE gel depicting different M-CSF variants cross-linked with $BS^3$ reagent, the quantities of monomer (20 kDa) and dimer (40 kDa) were visualized on SDS-PAGE gel for human M-CSF (upper left), murine M-CSF (lower left), M-$CSF_{C31S}$ (upper right) and M-$CSF_{C31S,M27R}$ (lower right). FIG. 16B shows distribution of hydration radii for M-$CSF_{WT}$ (solid line), M-$CSF_{C31S}$ (dashed line) and M-$CSF_{C31S,M27R}$ (dotted line) as measured by DLS. The calculated hydration radius is presented for each variant. FIG. 16C shows Radii of gyration determined by in-house script for M-$CSF_{WT}$ and its two variants (M-$CSF_{C31S}$ and M-$CSF_{C31S,M27R}$). The dashed lines represent the theoretical $R_g$ values for the M-CSF monomer ($R_g$=17 Å) and M-CSF dimer ($R_g$=26 Å) calculated from the crystal structure [PDB ID: 3UF2] using CRYSOL.

FIGS. 19A-19B. M-$CSF_{C31S,M27R}$ inhibits monocyte differentiation into osteoclasts. (19A) Differentiation of bone marrow derived monocytes (BMMs) in the presence of murine M-CSF+RANKL (positive control), M-CSF without RANKL (negative control), and M-CSF+RANKL+M-$CSF_{C31S}$ or M-$CSF_{C31S,M27R}$ at concentrations of 50 nM, 1 μM was evaluated. Cells were stained using TRAP staining and photographed (upper panels). The number of osteoclasts (lower left) and number of nuclei in osteoclasts (lower right) were quantified. (19B) Differentiation of $CD14^+$ in the presence of human M-CSF+murine RANKL (positive control), M-CSF without RANKL (negative control), and M-CSF+RANKL+M-$CSF_{C31S}$ or M-$CSF_{C31S,M27R}$ at concentrations of 50 nM, 250 nM and 1 μM was evaluated. Cells were stained using TRAP staining and cells were photographed (upper panels). The number of osteoclasts (lower left) and number of nuclei in osteoclasts (lower right) were quantified. Statistical analysis was performed using a t-test, each sample was compared to the positive control. N=3. Values are means±SEM. *, $p<0.05$; * *, $p<0.01$; * * *, $p<0.005$.

FIGS. 20A-20C. M-CSF variants activate c-FMS with different potencies. (20A) Quantification of phosphorylated murine c-FMS in the presence of 0.5 nM murine M-CSF (positive control), no M-CSF (negative control), M-$CSF_{WT}$ (0.5, 5 and 10 nM), M-$CSF_{C31S}$ and M-$CSF_{C31S,M27R}$ (0.5, 5, 10, 50, 1000 and 5000 nM) in the absence of murine M-CSF. All signals were normalized to those of β-actin, c-FMS expression and the positive control in each experiment. Statistical analysis was calculated using a t-test, each sample was compared to the positive control. N=3. Values are means±SEM. (20B) An illustration showing c-FMS activation at different concentration of M-$CSF_{WT}$, M-$CSF_{C31S}$ and M-$CSF_{C31S,M27R}$. (20C) An illustration of the hypothesized inhibitory mechanism of M-$CSF_{WT}$, M-$CSF_{C31S}$ and M-$CSF_{C31S,M27R}$ at different oligomerization states as a function of their concentrations.

Figure 2:
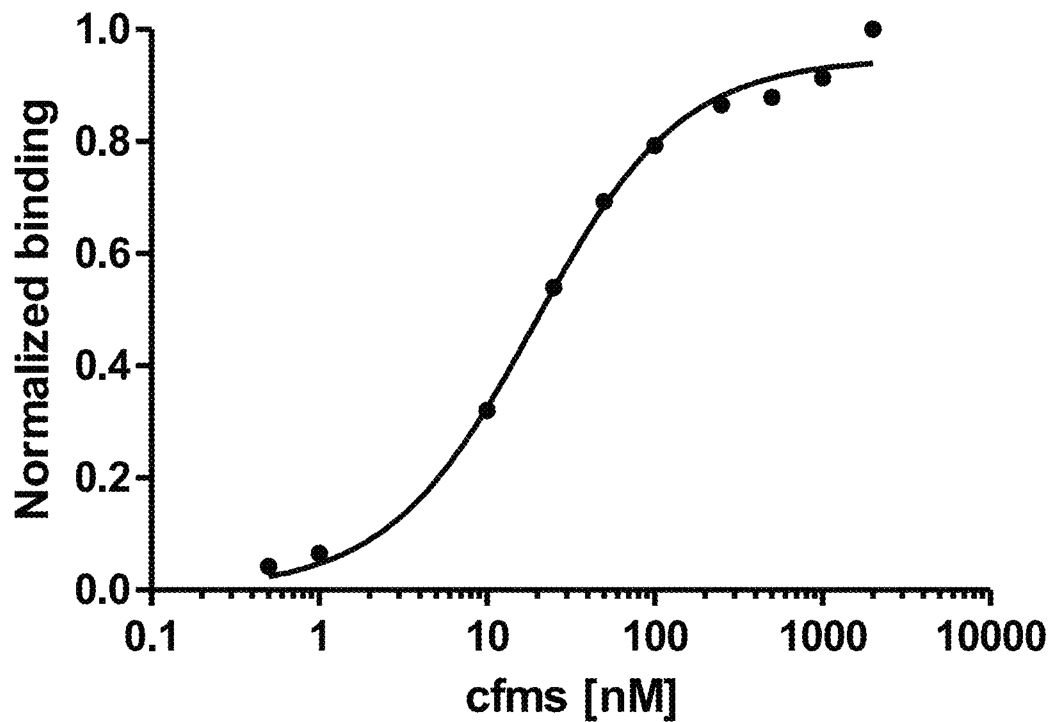
FIG. 2 is a graph showing a binding titration curve of YSD M-CSF$_{M}$.
Figure 3A:
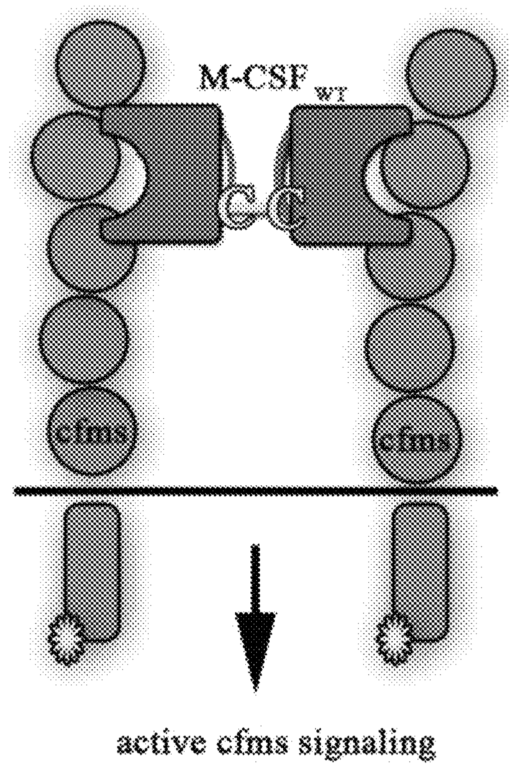
FIGS. 3A-3D are schematic illustrations of the different M-CSF constructs and their resulting signaling events: (3A) M-CSF$_{WT}$ is a disulfide-bond-linked homodimer which binds and activates cFMS, (3B) M-CSF monomer (designated M-CSF$_{M}$) designed with a cysteine to serine substitution in position 31 to prevent dimerization via a disulfide bond, which binds to c-FMS and inhibits its mediated signaling, (3C) Mono-specific M-CSF that can bind integrin $\alpha_v\beta_3$ (via an RGD motif) but not c-FMS (designated M-CSF$_{\alpha v\beta 3}$) due to mutations in positions 9 and 15 that prevent M-CSF binding to its receptor, and (3D) M-CSF$_{RGD}$ which was created by substituting one of the two loops (AB loop or CD loop) on the M-CSF dimerization site to an RGD motif with 3 random amino acids on each side that enables the M-CSF$_{RGD}$ to bind $\alpha_v\beta_3$ integrin as well as c-FMS and inhibit their mediated signaling events.
Figure 3B:
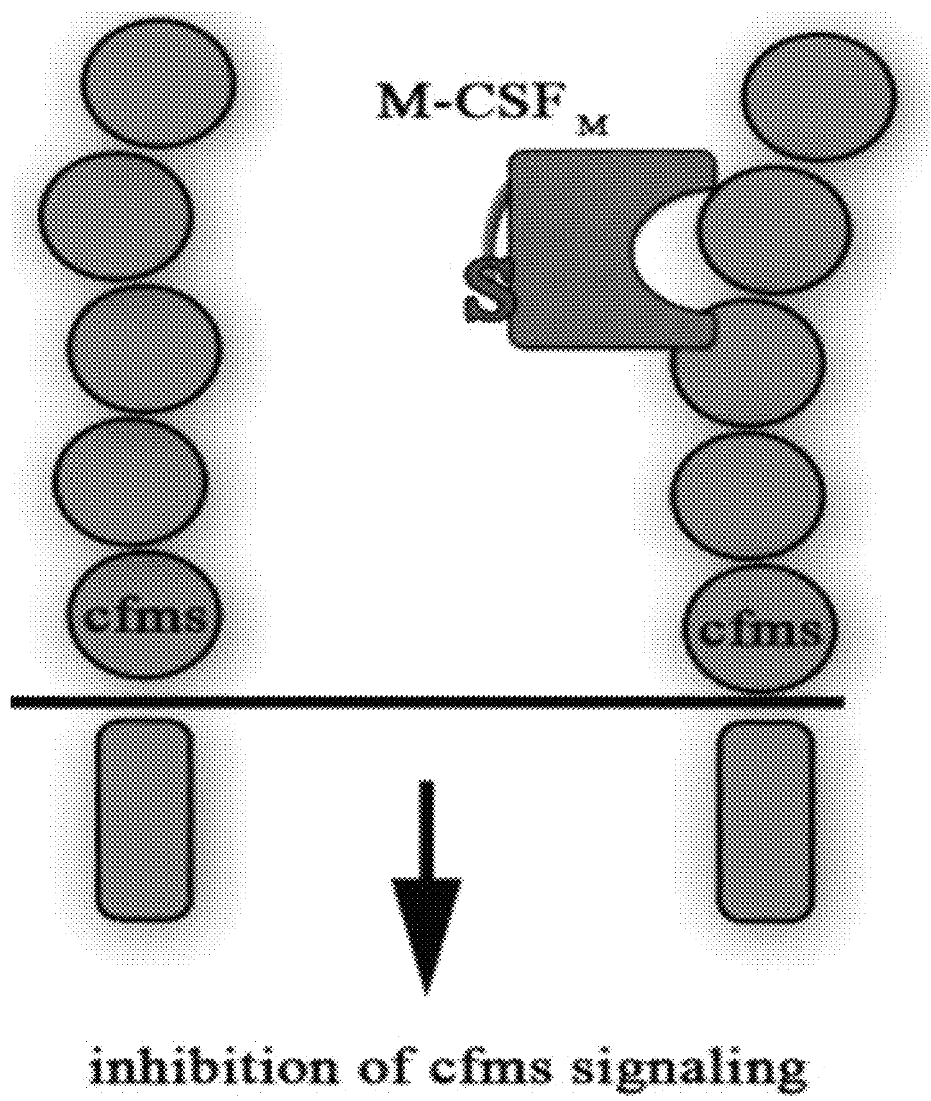
Figure 3C:
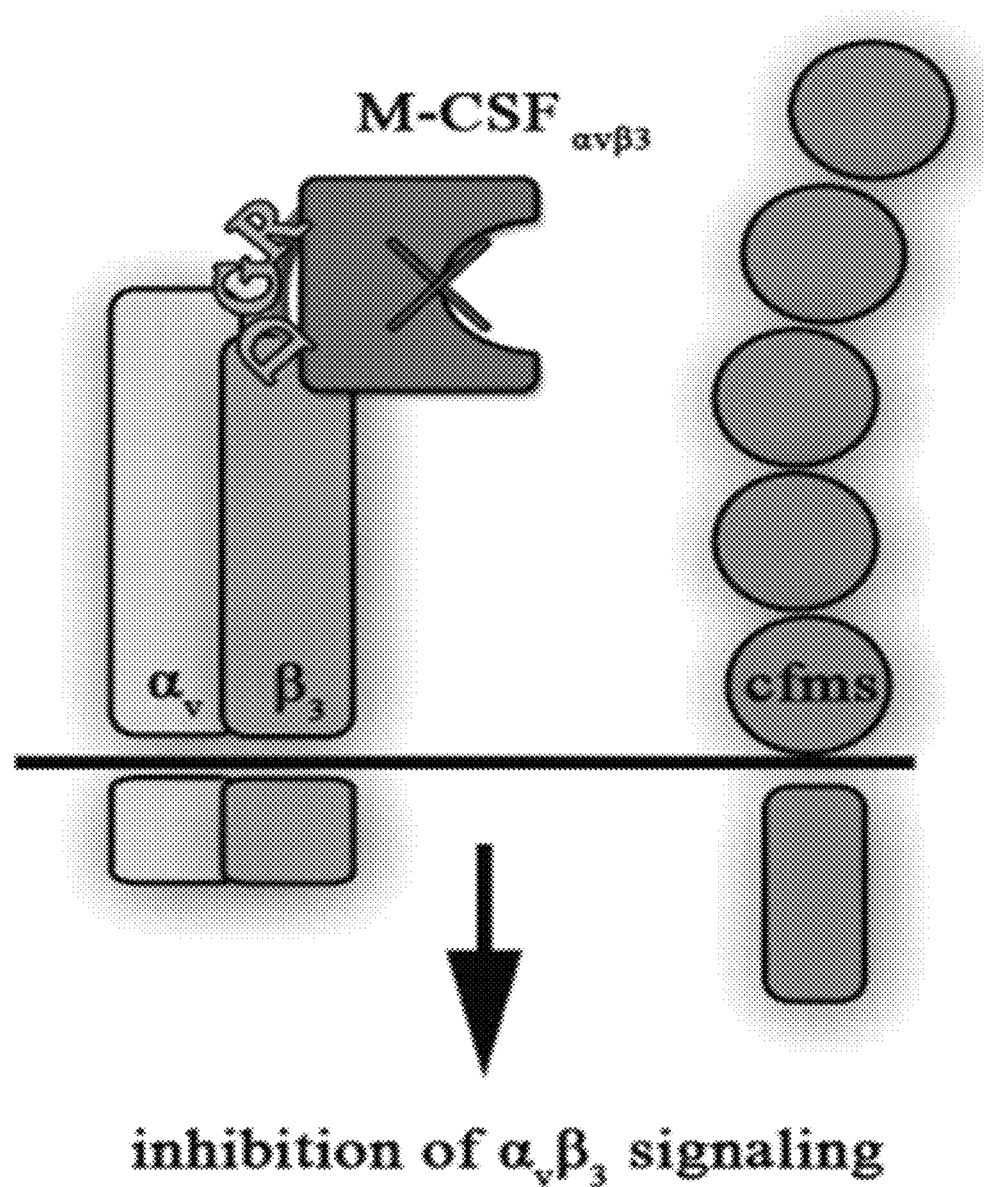
Figure 3D:
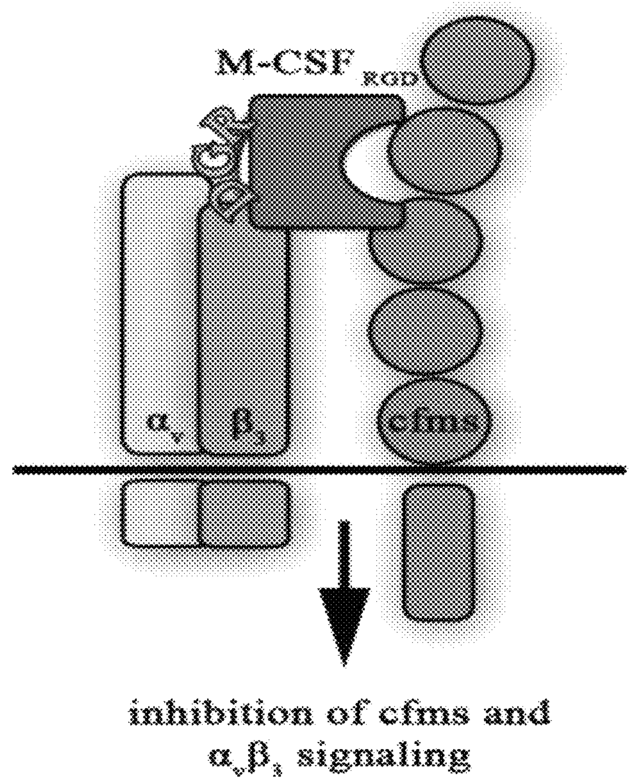

The patent or application file contains at least one drawing executed in color. Copies of this patent or patent application publication with color drawing(s) will be provided by the Office upon request and payment of necessary fee.

DETAILED DESCRIPTION OF THE INVENTION

The present invention provides a modified M-CSF protein and composition or kits comprising same. The invention further provides methods of treatment using said modified M-CSF. In some embodiments, the modified M-CSF of some embodiments of the invention is unable to undergo M-CSF homo-dimerization and has enhanced binding affinity to 43 and c-FMS. In some embodiment, the modified M-CSF comprises an RGD motif. In some embodiment, the modified M-CSF comprises a mutation of cysteine (Cys) at position 31 and methionine (Met) at position 27 of SEQ ID NO:1.

Advantageously, the modified M-CSF protein of some embodiments of the invention acts as an antagonist for both c-FMS and αvβ3 integrin. As known in the art, c-FMS and αvβ3 are typically expressed on membranes of osteoclasts and their activation is required for osteoclast differentiation. Hence, the modified M-CSF protein of the present invention is, in some embodiments, capable of inhibiting or reducing osteoclast differentiation. The modified M-CSF protein of the invention is, in additional embodiments, capable of reducing bone resorption. In some embodiments, the modified M-CSF of the invention is practically useful in the treatment and/or prevention of osteoporosis.

The present invention is based, in part, on the surprising finding that the modified M-CSF disclosed herein bind αvβ3 integrin and c-FMS and inhibit activity thereof. The present invention is further based, in part, on the surprising finding that the modified M-CSF disclosed herein inhibits osteoclast differentiation.

As exemplified in the example section below inhibition is achieved using modified M-CSF comprising substitution of cysteine 31 and an RGD motif inserted into a loop AB or a loop CD thereof. As further exemplified in the example section below, modified M-CSF comprising mutations in positions 9 and 15 of SEQ ID NO: 1 are incapable of binding c-FMS.

Modified M-CSF

According to one aspect, the invention provides a polypeptide comprising an amino acid sequence having at least 90% homology to SEQ ID NO: 1, said polypeptide comprising an RGD motif comprising the amino acid sequence as set forth in SEQ ID NO: 6 (RGD).

In some embodiments, the polypeptide comprises an amino acid sequence having at least 90%, 91%, 92%, 93%, or 94% homology to SEQ ID NO: 1

(EEVSEYCSHMIGSGHLQSLQRLIDSQMETSXQITFEFVDQEQLKDPVCYL
KKAFLLVQDIMEDTMRFRDNTEPVRGDNINPNAIAIVQLQELSLRLKSCFT
KDYEEHDKACVRTFYETPLQLLEKVKNVFNETKNLLDKDWNIFSKNCNNSF
AECSS), wherein X is any amino acid other than cysteine.

One skilled in the art will appreciate that monocyte/macrophage colony stimulating factor (M-CSF) have the Uniprot accession no. P09603 and comprise an AB loop (amino acids 25-32), a BC loop (amino acids 64-71), and a CD loop (amino acids 90-103).

In some embodiments, at least one loop selected from the AB loop and the CD loop comprises a modification of 3-10 contiguous amino acid residues compared to the corresponding AB loop or CD loop of SEQ ID NO: 1. In some embodiments the modification is selected from: deletion, substitution and addition of amino acid residues.

In some embodiments, at least one loop selected from the AB loop and the CD loop comprises the RGD motif. In some embodiments, the AB loop comprises the RGD motif. In some embodiments, the CD loop comprises the RGD motif.

In some embodiments, the polypeptide comprises one or more amino acid sequences selected from the group consisting of:

SEQ ID NO: 3
(EEVSEYCSHMIGSGHLQSLQRLID),

SEQ ID NO: 4
(ITFEFVDQEQLKDPVCYLKKAFLLVQDIMED),
and

SEQ ID NO: 5
(PNAIAIVQLQELSLRLKSCFTKDYEEHDKACVRTFYETPLQLLEKVKNVF
NETKNLLDKDWNIFSKNCNNSFAECSS).

In some embodiments, the mutant polypeptide is incapable of forming homodimers. In some embodiments, the polypeptide binds c-FMS and $\alpha_v\beta_3$ integrin.

In some embodiments, the polypeptide comprises an amino acid sequence as set forth in formula I (EEVSEYCSHMIGSGHLQSLQRLID(SQMETSSQ)$_b$($X_1X_2X_3$RGD$X_4X_5$
S)$_{(1-b)}$ITFEFVDQEQLKDPVCYLKKAFLLVQDIMED(TMRFRDN
T)$_{(1-b)}$(EPVRGDNIN)$_b$PNAIAIVQLQELSLRLKSCFTKDYEEHDKACV
RTFYETPLQLLEKVKNVFNETKNLLDKDWNIFSKNCNNSFAECSS), wherein b is an integer selected from 0 and 1, and wherein: $X_1$ is Q or T, $X_2$ is T or Y, $X_3$ is S or P, $X_4$ is S or M, and $X_5$ is P or C.

In some embodiments, the polypeptide comprises an amino acid sequence as set forth in SEQ ID NO: 12
(EEVSEYCSHMIGSGHLQSLQRLIDQTPRGDSPSITFEFVDQEQLKDPVCY
LKKAFLLVQDIMEDTMRFRDNTPNAIAIVQLQELSLRLKSCFTKDYEEHDK
ACVRTFYETPLQLLEKVKNVFNETKNLLDKDWNIFSKNCNNSFAECSS).

In some embodiments, the polypeptide comprises an amino acid sequence as set forth in SEQ ID NO: 13
(EEVSEYCSHMIGSGHLQSLQRLIDTYPRGDMCSITFEFVDQEQLKDPVCY
LKKAFLLVQDIMEDTMRFRDNTPNAIAIVQLQELSLRLKSCFTKDYEEHDK
ACVRTFYETPLQLLEKVKNVFNETKNLLDKDWNIFSKNCNNSFAECSS).

In some embodiments, the polypeptide comprises an amino acid sequence as set forth in SEQ ID NO: 14
(EEVSEYCSHMIGSGHLQSLQRLIDSQMETSSQITFEFVDQEQLKDPVCYL
KKAFLLVQDIMEDEPVRGDNINPNAIAIVQLQELSLRLKSCFTKDYEEHDK
ACVRTFYETPLQLLEKVKNVFNETKNLLDKDWNIFSKNCNNSFAECSS).

In some embodiments, the polypeptide comprises an amino acid sequence as set forth in formula II:

EEVSEYCSHMIGSGHLQSLQRLID(SQMETSSQ)$_b$($X_1X_2X_3$RGD$X_4X_5$
S)$_{(1-b)}$ITFEFVDQEQLKDPVCYLKKAFLLVQDIMED(TIVIRFRDN
T)$_{(1-b)}$(EPVRGDNIN)$_b$PNAIAIVQLQELSLRLKSCFTKDYEEHDKACV
RTFYETPLQLLEKVKNVFNETKNLLDKDWNIFSKNCNNSFAECSSQDVVTK
PDCNCLYPKAIPSSDPASVSPHQPLAPSMAPVAGLTWEDSEGTEGSSLLPG
EQPLHTVDPGSAKQRPPRSTCQSFEPPETPVVKDSTIGGSPQPRPSVGAFN
PGIVIEDILDSAMGTNWVPEEASGEASEIPVPQGTELSPSRPGGGSMQTEP
ARPSNFLSASSPLPASAKGQQPADVTGTALPRVGPVRPTGQDWNHTPQKTD
HPSALLRDPPEPGSPRISSLRPQGLSNPSTLSAQPQLSRSHSSGSVLPLGE
LEGRRSTRDRRSPAEPEGGPASEGAARPLPRFNSVPLTDTGHERQSEGS, wherein b is an integer selected from 0 and 1, and wherein: $X_1$ is Q or T, $X_2$ is T or Y, $X_3$ is S or P, $X_4$ is S or M, and $X_5$ is P or C.

As used herein "b" and "1-b" represent the number of repetitions of a sequence enclosed within the preceding adjacent brackets. The number of repetitions may vary between 0 and 1. For a non-limiting example when b equals 0, the preceding sequence within the brackets is not part of the sequence. "1-b" represents a mathematical equation resulting in an integer which equals 1 or 0.

In some embodiments, the polypeptide comprises an amino acid sequence as set forth in

SEQ ID NO: 16

```
(EEVSEYCSHMIGSGHLQSLQRLID X1X2X3RGDX4X5SITFEFVDQEQLK
DPVCYLKKAFLLVQDIMEDTMRFRDNTPNAIAIVQLQELSLRLKSCFTKDY
EEHDKACVRTFYETPLQLLEKVKNVFNETKNLLDKDWNIFSKNCNNSFAEC
SSQDVVTKPDCNCLYPKAIPSSDPASVPHQPLAPSMAPVAGLTWEDSEGTE
GSSLLPGEQPLHTVDPGSAKQRPPRSTCQSFEPPETPVVKDSTIGGSPQPR
PSVGAFNPGMEDILDSAMGTNWVPEEASGEASEIPVPQGTELSPSRPGGGS
MQTEPARPSNFLSASSPLPASAKGQQPADVTGTALPRVGPVRPTGQDWNHT
PQKTDHPSALLRDPPEPGSPRISSLRPQGLSNPSTLSAQPQLSRSHSSGSV
LPLGELEGRRSTRDRRSPAEPEGGPASEGAARPLPRFNSVPLTDTGHERQS
EGS)
```

wherein: $X_1$ is Q or T, $X_2$ is T or Y, $X_3$ is S or P, $X_4$ is S or M, and $X_5$ is P or C.

In some embodiments, the polypeptide comprises an amino acid sequence as set forth in

SEQ ID NO: 17

```
(EEVSEYCSHMIGSGHLQSLQRLIDSQMETSSQITFEFVDQEQLKDPVCY
LKKAFLLVQDIMEDEPVRGDNINPNAIAIVQLQELSLRLKSCFTKDYEEH
DKACVRTFYETPLQLLEKVKNVFNETKNLLDKDWNIFSKNCNNSFAECSS
QDVVTKPDCNCLYPKAIPSSDPASVSPHQPLAPSMAPVAGLTWEDSEGTE
GSSLLPGEQPLHTVDPGSAKQRPPRSTCQSFEPPETPVVKDSTIGGSPQP
RPSVGAFNPGMEDILDSAMGTNWVPEEASGEASEIPVPQGTELSPSRPGG
GSMQTEPARPSNFLSASSPLPASAKGQQPADVTGTALPRVGPVRPTGQDW
NHTPQKTDHPSALLRDPPEPGSPRISSLRPQGLSNPSTLSAQPQLSRSHS
SGSVLPLGELEGRRSTRDRRSPAEPEGGPASEGAARPLPRFNSVPLTDTG
HERQSEGS).
```

As used herein, the terms "peptide", "polypeptide" and "protein" are used interchangeably to refer to a polymer of amino acid residues. The terms "peptide", "polypeptide" and "protein" as used herein encompass native peptides, peptidomimetics (typically including non-peptide bonds or other synthetic modifications) and the peptide analogs peptoids and semi-peptoids or any combination thereof. In another embodiment, the terms "peptide", "polypeptide" and "protein" apply to amino acid polymers in which one or more amino acid residue is an artificial chemical analog of a corresponding naturally occurring amino acid.

In one embodiment, the polypeptide of the invention comprises or consists of the amino acid sequence as set forth in SEQ ID NO: 11, 12, 13, 14, 15, 16 or 17, or a sequence derived therefrom.

As used herein, the term "derived from" or "corresponding to" refers to construction of an amino acid sequence based on the knowledge of a sequence using any one of the suitable means known to one skilled in the art, e.g. chemical synthesis in accordance with standard protocols in the art.

One of skill in the art will recognize that individual substitutions, deletions or additions to a peptide, or protein sequence which alters, adds or deletes a single amino acid or a small percentage of amino acids in the encoded sequence is a conservatively modified variant where the alteration results in the substitution of an amino acid with a similar charge, size, and/or hydrophobicity characteristics, such as, for example, substitution of a glutamic acid (E) to aspartic acid (D).

In some embodiments, the polypeptide of the invention comprises a sequence derived from SEQ ID NO: 11, 12, 13, 14, 15, 16 or 17 with one or more conservative substitution. In some embodiments, the mutant polypeptide of the invention comprises a sequence derived from SEQ ID NO: 11, 12, 13, 14, 15, 16 or 17 with at most 1, 2, 3, 4, 5, 6, or 7 conservative substitutions. Each possibility represents a separate embodiment of the present invention. According to another embodiment of the invention, the polypeptide of the invention comprises a sequence homologous to SEQ ID NO: 11, 12, 13, 14, 15, 16, or 17. According to another embodiment of the invention, the polypeptide of the invention comprises a sequence having greater than 70%, 75%, 80%, 85%, 90%, 91%, 92%, 93%, 94%, 95%, 96%, 97%, 98%, or 99% homology to SEQ ID NO: 11, 12, 13, 14, 15, 16 or 17. Each possibility represents a separate embodiment of the present invention.

In some embodiments, the polypeptide of the invention comprises a sequence having at least 94%, 95%, 96%, 97%, 98%, or 99% homology to SEQ ID NO: 11, 12, 13, 14, 15, 16 or 17, wherein the mutant M-CSF is incapable of forming homodimers, wherein the mutant M-CSF binds c-FMS and wherein the mutant M-CSF binds $\alpha v\beta 3$ integrin. Each possibility represents a separate embodiment of the present invention.

In some embodiments, the polypeptide of the invention comprises a sequence having at least 94%, 95%, 96%, 97%, 98%, or 99% homology to a sequence selected from the group consisting of: SEQ ID NOs: 11, 12, 13, 14, 15, 16 and 17, wherein the polypeptide of the invention is incapable of forming homodimers, wherein the polypeptide of the invention binds c-FMS and wherein the polypeptide of the invention binds $\alpha v\beta 3$ integrin. Each possibility represents a separate embodiment of the present invention.

As used herein, the term "analog" includes any peptide having an amino acid sequence substantially identical to one of the sequences specifically shown herein in which one or more residues have been conservatively substituted with a functionally similar residue and which displays the abilities as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another. Each possibility represents a separate embodiment of the present invention.

As used herein, the phrase "conservative substitution" also includes the use of a chemically derivatized residue in place of a non-derivatized residue provided that such peptide displays the requisite function as specified herein.

In one embodiment, the polypeptide is a variant of SEQ ID NO: 11, 12, 13, 14, 15, 16 or 17.

In another embodiment, the term "variant" refers to a polypeptide or nucleotide sequence which comprises a modification of one or more amino acids or nucleotides as compared to another polypeptide or polynucleotide, respectively. In some embodiments, the modifications are substitution, deletion, and/or insertion of one or more amino acids or nucleotides as compared to another polypeptide or polynucleotide, respectively. In some embodiments, the changes may be of minor nature, such as conservative amino acid substitutions or for nucleotide sequence resulting in conservative amino acid substitutions that do not significantly affect the activity of the polypeptide. In some embodiments, the changes may be substitution of an amino acid molecule, resulting in an addition of a glycosylation site, thereby increasing glycosylation of the polypeptide.

Typically, the present invention encompasses derivatives of the polypeptides. The term "derivative" or "chemical derivative" includes any chemical derivative of the polypeptide having one or more residues chemically derivatized by reaction of side chains or functional groups. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides, which contain one or more naturally occurring amino acid derivatives of the twenty standard amino acid residues. For example: 4-hydroxyproline may be substituted for proline; 5-hydroxylysine may be substituted for lysine; 3-methylhistidine may be substituted for histidine; homoserine may be substituted or serine; and ornithine may be substituted for lysine.

In addition, a peptide derivative can differ from the natural sequence of the peptides of the invention by chemical modifications including, but are not limited to, terminal-NH2 acylation, acetylation, or thioglycolic acid amidation, and by terminal-carboxlyamidation, e.g., with ammonia, methylamine, and the like. Peptides can be either linear, cyclic or branched and the like, which conformations can be achieved using methods well known in the art.

The peptide derivatives and analogs according to the principles of the present invention can also include side chain bond modifications, including but not limited to —CH2-NH—, —CH2-S—, —CH2-S═O, OC—NH—, —CH2-O—, —CH2-CH2-, S═C—NH—, and —CH═CH—, and backbone modifications such as modified peptide bonds. Peptide bonds (—CO—NH—) within the peptide can be substituted, for example, by N-methylated bonds (—N(CH3)-CO—); ester bonds (—C(R)H—C—O—O—C(R)H—N); ketomethylene bonds (—CO—CH2-); a-aza bonds (—NH—N(R)—CO—), wherein R is any alkyl group, e.g., methyl; carba bonds (—CH2-NH—); hydroxyethylene bonds (—CH(OH)—CH2-); thioamide bonds (—CS—NH); olefmic double bonds (—CH═CH—); and peptide derivatives (—N(R)—CH2-CO—), wherein R is the "normal" side chain, naturally presented on the carbon atom. These modifications can occur at one or more of the bonds along the peptide chain and even at several (e.g., 2-3) at the same time.

The present invention also encompasses peptide derivatives and analogs in which free amino groups have been derivatized to form amine hydrochlorides, p-toluene sulfonylamino groups, carbobenzoxyamino groups, t-butyloxycarbonylamino groups, chloroacetylamino groups or formylamino groups. Free carboxyl groups may be derivatized to form, for example, salts, methyl and ethyl esters or other types of esters or hydrazides. The imidazole nitrogen of histidine can be derivatized to form N-im-benzylhistidine.

As used herein the term "salts" refers to both salts of carboxyl groups and to acid addition salts of amino or guanido groups of the peptide molecule. Salts of carboxyl groups may be formed by means known in the art and include inorganic salts, for example sodium, calcium, ammonium, ferric or zinc salts, and the like, and salts with organic bases such as salts formed for example with amines such as triethanolamine, piperidine, procaine, and the like. Acid addition salts include, for example, salts with mineral acids such as, for example, acetic acid or oxalic acid. Salts describe here also ionic components added to the peptide solution to enhance hydrogel formation and/or mineralization of calcium minerals.

The peptide analogs can also contain non-natural amino acids. Examples of non-natural amino acids include, but are not limited to, sarcosine (Sar), norleucine, ornithine, citrulline, diaminobutyric acid, homoserine, isopropyl Lys, 3-(2'-naphtyl)-Ala, nicotinyl Lys, amino isobutyric acid, and 3-(3'-pyridyl-Ala).

Furthermore, the peptide analogs can contain other derivatized amino acid residues including, but not limited to, methylated amino acids, N-benzylated amino acids, O-benzylated amino acids, N-acetylated amino acids, O-acetylated amino acids, carbobenzoxy-substituted amino acids and the like. Specific examples include, but are not limited to, methyl-Ala (Me Ala), MeTyr, MeArg, MeGlu, MeVal, MeHis, N-acetyl-Lys, O-acetyl-Lys, carbobenzoxy-Lys, Tyr-O-Benzyl, Glu-O-Benzyl, Benzyl-His, Arg-Tosyl, t-butylglycine, t-butylalanine, phenylglycine, cyclohexylalanine, and the like.

The invention further includes peptide analogs, which can contain one or more D-isomer forms of the amino acids. Production of retro-inverso D-amino acid peptides where at least one amino acid and perhaps all amino acids are D-amino acids is well known in the art. When all of the amino acids in the peptide are D-amino acids, and the N- and C-terminals of the molecule are reversed, the result is a molecule having the same structural groups being at the same positions as in the L-amino acid form of the molecule. However, the molecule is more stable to proteolytic degradation and is therefore useful in many of the applications recited herein. Diastereomeric peptides may be highly advantageous over all L- or all D-amino acid peptides having the same amino acid sequence because of their higher water solubility, lower immunogenicity, and lower susceptibility to proteolytic degradation. The term "diastereomeric peptide" as used herein refers to a peptide comprising both L-amino acid residues and D-amino acid residues. The number and position of D-amino acid residues in a diastereomeric peptide of the preset invention may be variable so long as the peptide is capable of displaying the function of disclosed by the modified M-SCF of the invention.

PEGylation

In some embodiments, the polypeptides of the present invention are conjugated to polyethylene glycol (PEG). Conjugation of PEG to polypeptides is known to prolong in-vivo half-life of polypeptides. PEGs are non-toxic polymers of ethylene oxide that are widely used in protein medications and other fields.

RGD Motifs

In some embodiment, the RGD motif comprises the amino acid sequence Arg-Gly-Asp as set forth in SEQ ID NO: 6 (RGD). In some embodiments, the RGD motif further comprises one or more randomized amino acid residues flanking either side or both sides of the RGD sequence. In some embodiments, the integrin binding motif comprises the amino acid sequence as set forth in SEQ ID NO: 7 (XXXRGDXXX), wherein each X individually represents any amino acid residue (e.g., a randomized amino acid residue). In some embodiments, the RGD motif exhibits a binding specificity to $\alpha_v\beta_3$. In some embodiments, the RGD motif has significantly higher binding affinity to $\alpha_v\beta_3$ than to other integrins (e.g., $\alpha_4\beta_7$, $\alpha_2\beta_{2b}$, $\alpha_5\beta_1$ and $\alpha_v\beta_5$).

In some embodiments, the RGD motif comprising the amino acid sequence as set forth in SEQ ID NO: 6 has a length of less than 30, 20, 18, 15, 12, 9, 8, 7, 6, 5, or 4 amino acids. Each possibility represents a separate embodiment of the present invention. In another embodiment, the RGD motif comprising the amino acid sequence as set forth in SEQ ID NO: 6 has a length of at least 3, 4, 5, 6, 7, 8, 9, 10, 11, 12, 13, 14, 15, 16, 17, 18, 19, 20, 21, 22, 23, 24, 25, 26, 27, 28, 29, or 30 amino acids derived from SEQ ID NO: 2. In another embodiment, the RGD motif comprising the amino acid sequence as set forth in SEQ ID NO: 6 has a length of 3 to 6, 3 to 7, 3 to 8, 3 to 9, 3 to 10, 3 to 11, 3 to 12, 3 to 14, 3 to 15, 3 to 16, 3 to 17, 3 to 18, 3 to 19, or 3 to 20. Each possibility represents a separate embodiment of the present invention. In some embodiments, the RGD motif comprises at least 9 amino acid residues. In some embodiments, the RGD motif comprises or consists of 9 amino acid residues. In some embodiments, the RGD motif has 3 to 20 amino acids, comprising the amino acid sequence as set forth in SEQ ID NO: 6 (RGD).

In some embodiments, the RGD motif comprises or consists of the amino acid sequence selected from the group consisting of: SEQ ID NO: 8 (QTSRGDSPS), SEQ ID NO: 9 (TYPRGDMCS), and SEQ ID NO: 10 (EPVRGDNIN). In some embodiments, the RGD motif is selected from the group consisting of: SEQ ID NO: 8 (QTSRGDSPS), SEQ ID NO: 9 (TYPRGDMCS).

In some embodiments, the RGD motif comprises or consists of the amino acid sequence as set forth in SEQ ID NO: 8 (QTSRGDSPS). In some embodiments, the RGD motif comprises or consists of the amino acid sequence as set forth in SEQ ID NO: 9 (TYPRGDMCS). In some embodiments, the RGD motif comprises or consists of the amino acid sequence as set forth in SEQ ID NO: 10 (EPVRGDNIN).

In some embodiments, the AB loop of the polypeptide comprises an RGD motif selected from the group consisting of: SEQ ID NO: 8 (QTSRGDSPS), SEQ ID NO: 9 (TYPRGDMCS). In some embodiments, the CD loop of the polypeptide comprises an RGD motif comprising or consisting of the amino acid sequence as set forth in SEQ ID NO: 10 (EPVRGDNIN).

Synthesizing the Polypeptide

According to one embodiment, the polypeptides of the present invention may be synthesized or prepared by any method and/or technique known in the art for peptide synthesis. According to another embodiment, the polypeptides may be synthesized by a solid phase peptide synthesis method of Merrifield (see J. Am. Chem. Soc, 85:2149, 1964). According to another embodiment, the polypeptides of the present invention can be synthesized using standard solution methods well known in the art (see, for example, Bodanszky, M., Principles of Peptide Synthesis, Springer-Verlag, 1984).

In general, the synthesis methods comprise sequential addition of one or more amino acids or suitably protected amino acids to a growing peptide chain bound to a suitable resin. Normally, either the amino or carboxyl group of the first amino acid is protected by a suitable protecting group. The protected or derivatized amino acid can then be either attached to an inert solid support (resin) or utilized in solution by adding the next amino acid in the sequence having the complimentary (amino or carboxyl) group suitably protected, under conditions conductive for forming the amide linkage. The protecting group is then removed from this newly added amino acid residue and the next amino acid (suitably protected) is added, and so forth. After all the desired amino acids have been linked in the proper sequence, any remaining protecting groups are removed sequentially or concurrently, and the peptide chain, if synthesized by the solid phase method, is cleaved from the solid support to afford the final peptide.

In the solid phase peptide synthesis method, the alpha-amino group of the amino acid is protected by an acid or base sensitive group. Such protecting groups should have the properties of being stable to the conditions of peptide linkage formation, while being readily removable without destruction of the growing peptide chain. Suitable protecting groups are t-butyloxycarbonyl (BOC), benzyloxycarbonyl (Cbz), biphenylisopropyloxycarbonyl, t-amyloxycarbonyl, isobornyloxycarbonyl, (alpha, alpha)-dimethyl-3 ,5 dimethoxybenzyloxycarbonyl, o-nitrophenylsulfenyl, 2-cyano-t-butyloxycarbonyl, 9-fluorenylmethyloxycarbonyl (FMOC) and the like. In the solid phase peptide synthesis method, the C-terminal amino acid is attached to a suitable solid support. Suitable solid supports useful for the above synthesis are those materials, which are inert to the reagents and reaction conditions of the stepwise condensation-deprotection reactions, as well as being insoluble in the solvent media used. Suitable solid supports are chloromethylpolystyrene-divinylbenzene polymer, hydroxymethyl-polystyrene-divinylbenzene polymer, and the like. The coupling reaction is accomplished in a solvent such as ethanol, acetonitrile, N,N-dimethylformamide (DMF), and the like. The coupling of successive protected amino acids can be carried out in an automatic polypeptide synthesizer as is well known in the art.

In another embodiment, polypeptides of the invention may be synthesized such that one or more of the bonds, which link the amino acid residues of the peptides are non-peptide bonds. In another embodiment, the non-peptide bonds include, but are not limited to, imino, ester, hydrazide, semicarbazide, and azo bonds, which can be formed by reactions well known to one skilled in the art.

The invention further encompasses a polynucleotide sequence comprising a nucleic acid encoding any of the polypeptides of the invention. In another embodiment, the nucleic acid sequence encoding the polypeptide is at least 70%, or alternatively at least 80%, or alternatively at least 90%, or alternatively at least 95%, or alternatively at least 99% homologous to the nucleic acid sequence encoding the nucleic acid sequence of the polypeptides of the invention or a fragment thereof.

In some embodiment, the invention provides a polynucleotide encoding the polypeptides of the invention.

In some embodiments, the polynucleotide of the present invention is ligated into an expression vector, comprising a transcriptional control of a cis-regulatory sequence (e.g., promoter sequence). In some embodiments, the cis-regulatory sequence is suitable for directing constitutive expression of the polypeptide of the present invention. In some embodiments, the cis-regulatory sequence is suitable for directing tissue-specific expression of the polypeptide of the present invention. In some embodiments, the cis-regulatory sequence is suitable for directing inducible expression of the polypeptide of the present invention.

The term "polynucleotide" refers to a nucleic acid (e.g., DNA or RNA) sequence that comprises coding sequences necessary for the production of a polypeptide. In one embodiment, a polynucleotide refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

In one embodiment, "complementary polynucleotide sequence" refers to a sequence, which results from reverse transcription of messenger RNA using a reverse transcriptase or any other RNA dependent DNA polymerase. In one embodiment, the sequence can be subsequently amplified in vivo or in vitro using a DNA polymerase.

In one embodiment, "genomic polynucleotide sequence" refers to a sequence derived (isolated) from a chromosome and thus it represents a contiguous portion of a chromosome.

In one embodiment, "composite polynucleotide sequence" refers to a sequence, which is at least partially complementary and at least partially genomic. In one embodiment, a composite sequence can include some exonal sequences required to encode the polypeptide of the present invention, as well as some intronic sequences interposing there between. In one embodiment, the intronic sequences can be of any source, including of other genes, and typically will include conserved splicing signal sequences. In one embodiment, intronic sequences include cis acting expression regulatory elements.

In some embodiments, polynucleotides of the present invention are prepared using PCR techniques as described in Example 1, or any other method or procedure known to one skilled in the art. In some embodiments, the procedure involves the ligation of two different DNA sequences (See, for example, "Current Protocols in Molecular Biology", eds. Ausubel et al., John Wiley & Sons, 1992).

In one embodiment, polynucleotides of the present invention are inserted into expression vectors (i.e., a nucleic acid construct) to enable expression of the recombinant polypeptide. In one embodiment, the expression vector of the present invention includes additional sequences which render this vector suitable for replication and integration in prokaryotes. In one embodiment, the expression vector of the present invention includes additional sequences which render this vector suitable for replication and integration in eukaryotes. In one embodiment, the expression vector of the present invention includes a shuttle vector which renders this vector suitable for replication and integration in both prokaryotes and eukaryotes. In some embodiments, cloning vectors comprise transcription and translation initiation sequences (e.g., promoters, enhancers) and transcription and translation terminators (e.g., polyadenylation signals).

In one embodiment, a variety of prokaryotic or eukaryotic cells can be used as host-expression systems to express the polypeptide of the present invention. In some embodiments, these include, but are not limited to, microorganisms, such as bacteria transformed with a recombinant bacteriophage DNA, plasmid DNA or cosmid DNA expression vector containing the polypeptide coding sequence; yeast transformed with recombinant yeast expression vectors containing the polypeptide coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the polypeptide coding sequence.

In some embodiments, non-bacterial expression systems are used (e.g. mammalian expression systems) to express the polypeptide of the present invention. In one embodiment, the expression vector is used to express polynucleotides of the present invention in mammalian cells.

In some embodiments, in bacterial systems of the present invention, a number of expression vectors can be advantageously selected depending upon the use intended for the polypeptide expressed. In one embodiment, large quantities of polypeptide are desired. In one embodiment, vectors that direct the expression of high levels of the protein product, possibly as a fusion with a hydrophobic signal sequence, which directs the expressed product into the periplasm of the bacteria or the culture medium where the protein product is readily purified are desired. In one embodiment, certain fusion protein engineered with a specific cleavage site to aid in recovery of the polypeptide. In one embodiment, vectors adaptable to such manipulation include, but are not limited to, the pET series of *E. coli* expression vectors [Studier et al., Methods in Enzymol. 185:60-89 (1990)].

In one embodiment, yeast expression systems are used. In one embodiment, a number of vectors containing constitutive or inducible promoters can be used in yeast as disclosed in U.S. Pat. No. 5,932,447. In another embodiment, vectors which promote integration of foreign DNA sequences into the yeast chromosome are used.

In one embodiment, the expression vector of the present invention may further include additional polynucleotide sequences that allow, for example, the translation of several proteins from a single mRNA such as an internal ribosome entry site (IRES).

In some embodiments, mammalian expression vectors include, but are not limited to, pcDNA3, pcDNA3.1 (±), pGL3, pZeoSV2(±), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

In some embodiments, expression vectors containing regulatory elements from eukaryotic viruses such as retroviruses are used by the present invention. SV40 vectors include pSVT7 and pMT2. In some embodiments, vectors derived from bovine papilloma virus include pBV-1MTHA, and vectors derived from Epstein Bar virus include pHEBO, and p2O5. Other exemplary vectors include pMSG, pAV009/A+, pMTO10/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

In some embodiments, recombinant viral vectors, which offer advantages such as lateral infection and targeting specificity, are used for in vivo expression of the polypeptide of the present invention. In one embodiment, lateral infection is inherent in the life cycle of, for example, retrovirus and is the process by which a single infected cell produces many progeny virions that bud off and infect neighboring cells. In one embodiment, the result is that a large area becomes rapidly infected, most of which was not initially infected by the original viral particles. In one embodiment, viral vectors are produced that are unable to spread laterally. In one embodiment, this characteristic can be useful if the desired purpose is to introduce a specified gene into only a localized number of targeted cells.

Various methods can be used to introduce the expression vector of the present invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

A person with skill in the art will appreciate that the polypeptide of the present invention can also be expressed from a nucleic acid construct administered to the individual employing any suitable mode of administration, described hereinabove (i.e., in vivo gene therapy). In one embodiment, the nucleic acid construct is introduced into a suitable cell via an appropriate gene delivery vehicle/method (transfection, transduction, homologous recombination, etc.) and an expression system as needed and then the modified cells are expanded in culture and returned to the individual (i.e., ex vivo gene therapy).

In one embodiment, in vivo gene therapy using a cytokine has been attempted in animal models such as rodents [Bohl et al., Blood. 2000; 95:2793-2798], primates [Gao et al., Blood, 2004, Volume 103, Number 9] and has proven successful in human clinical trials for patients with chronic renal failure [Lippin et al Blood 2005, 106, Number 7].

In one embodiment, plant expression vectors are used. In one embodiment, the expression of a polypeptide coding sequence is driven by a number of promoters. In some embodiments, viral promoters such as the 35S RNA and 19S RNA promoters of CaMV [Brisson et al., Nature 310:511 514 (1984)], or the coat protein promoter to TMV [Takamatsu et al., EMBO J. 6:307-311 (1987)] are used. In another embodiment, plant promoters are used such as, for example, the small subunit of RUBISCO [Coruzzi et al., EMBO J. 3:1671-1680 (1984); and Brogli et al., Science 224:838-843 (1984)] or heat shock promoters, e.g., soybean hsp17.5-E or hsp17.3-B [Gurley et al., Mol. Cell. Biol. 6:559-565 (1986)]. In one embodiment, constructs are introduced into plant cells using Ti plasmid, Ri plasmid, plant viral vectors, direct DNA transformation, microinjection, electroporation and other techniques well known to the skilled artisan. See, for example, Weissbach & Weissbach [Methods for Plant Molecular Biology, Academic Press, NY, Section VIII, pp 421 463 (1988)]. Other expression systems such as insects and mammalian host cell systems, which are well known in the art, can also be used by the present invention.

It will be appreciated that other than containing the necessary elements for the transcription and translation of the inserted coding sequence (encoding the polypeptide), the expression construct of the present invention can also include sequences engineered to optimize stability, production, purification, yield or activity of the expressed polypeptide.

In some embodiments, transformed cells are cultured under effective conditions, which allow for the expression of high amounts of recombinant polypeptide. In some embodiments, effective culture conditions include, but are not limited to, effective media, bioreactor, temperature, pH and oxygen conditions that permit protein production. In one embodiment, an effective medium refers to any medium in which a cell is cultured to produce the recombinant polypeptide of the present invention. In some embodiments, a medium typically includes an aqueous solution having assimilable carbon, nitrogen and phosphate sources, and appropriate salts, minerals, metals and other nutrients, such as vitamins. In some embodiments, cells of the present invention can be cultured in conventional fermentation bioreactors, shake flasks, test tubes, microtiter dishes and petri plates. In some embodiments, culturing is carried out at a temperature, pH and oxygen content appropriate for a recombinant cell. In some embodiments, culturing conditions are within the expertise of one of ordinary skill in the art.

In some embodiments, depending on the vector and host system used for production, resultant polypeptides of the present invention either remain within the recombinant cell, secreted into the fermentation medium, secreted into a space between two cellular membranes, such as the periplasmic space in *E. coli*; or retained on the outer surface of a cell or viral membrane. In one embodiment, following a predetermined time in culture, recovery of the recombinant polypeptide is affected.

In one embodiment, the phrase "recovering the recombinant polypeptide" used herein refers to collecting the whole fermentation medium containing the polypeptide and need not imply additional steps of separation or purification.

In one embodiment, polypeptides of the present invention are purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

In one embodiment, to facilitate recovery, the expressed coding sequence can be engineered to encode the polypeptide of the present invention and fused cleavable moiety. In one embodiment, a fusion protein can be designed so that the polypeptide can be readily isolated by affinity chromatography; e.g., by immobilization on a column specific for the cleavable moiety. In one embodiment, a cleavage site is engineered between the polypeptide and the cleavable moiety, and the polypeptide can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265:15854-15859 (1990)].

In one embodiment, the polypeptide of the present invention is retrieved in "substantially pure" form that allows for the effective use of the protein in the applications described herein.

As used herein, the term "substantially pure" describes a peptide/polypeptide or other material which has been separated from its native contaminants. Typically, a monomeric peptide is substantially pure when at least about 60 to 75% of a sample exhibits a single peptide backbone. Minor variants or chemical modifications typically share the same peptide sequence. A substantially pure peptide can comprise over about 85 to 90% of a peptide sample, and can be over 95% pure, over 97% pure, or over about 99% pure. Purity can be measured on a polyacrylamide gel, with homogeneity determined by staining. Alternatively, for certain purposes high resolution may be necessary and HPLC or a similar means for purification can be used. For most purposes, a simple chromatography column or polyacrylamide gel can be used to determine purity.

The term "purified" does not require the material to be present in a form exhibiting absolute purity, exclusive of the presence of other compounds. Rather, it is a relative definition. A peptide is in the "purified" state after purification of the starting material or of the natural material by at least one order of magnitude, 2 or 3, or 4 or 5 orders of magnitude.

In one embodiment, the polypeptides of the present invention are substantially free of naturally-associated host cell components. The term "substantially free of naturally-associated host cell components" describes a peptide or other material which is separated from the native contaminants which accompany it in its natural host cell state. Thus, a peptide which is chemically synthesized or synthesized in a cellular system different from the host cell from which it naturally originates will be free from its naturally-associated host cell components.

In one embodiment, the polypeptide of the present invention can also be synthesized using in vitro expression systems. In one embodiment, in vitro synthesis methods are well known in the art and the components of the system are commercially available.

Pharmaceutical Compositions

According to another aspect, the invention provides a pharmaceutical composition comprising as an active ingredient a therapeutically effective amount of the polypeptide of the present invention, and a pharmaceutically acceptable carrier and/or diluent. In some embodiments, the pharmaceutical composition facilitates administration of a compound to an organism.

In another embodiment, the pharmaceutical compositions of the invention may be formulated in the form of a pharmaceutically acceptable salt of the polypeptides of the present invention or their analogs, or derivatives thereof. In another embodiment, pharmaceutically acceptable salts include those salts formed with free amino groups such as salts derived from non toxic inorganic or organic acids such as hydrochloric, phosphoric, acetic, oxalic, tartaric acids, and the like, and those salts formed with free carboxyl groups such as salts derived from non-toxic inorganic or organic bases such as sodium, potassium, ammonium, calcium, ferric hydroxides, isopropylamine, triethylamine, 2-ethylamino ethanol, histidine, procaine, and the like.

As used herein, the term "carrier" refers to a diluent, adjuvant, excipient, or vehicle with which the therapeutic compound is administered. Such pharmaceutical carriers can be sterile liquids, such as water and oils, including those of petroleum, animal, vegetable or synthetic origin, such as peanut oil, soybean oil, mineral oil, sesame oil and the like, polyethylene glycols, glycerin, propylene glycol or other synthetic solvents. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfate; and agents for the adjustment of tonicity such as sodium chloride or dextrose are also envisioned. The carrier may comprise, in total, from about 0.1% to about 99.99999% by weight of the pharmaceutical compositions presented herein.

As used herein, the term "pharmaceutically acceptable" means suitable for administration to a subject, e.g., a human. For example, the term "pharmaceutically acceptable" can mean approved by a regulatory agency of the Federal or a state government or listed in the U. S. Pharmacopeia or other generally recognized pharmacopeia for use in animals, and more particularly in humans.

In another embodiment, the compositions of the invention take the form of solutions, suspensions, emulsions, tablets, pills, capsules, powders, gels, creams, ointments, foams, pastes, sustained-release formulations and the like. In another embodiment, the compositions of the invention can be formulated as a suppository, with traditional binders and carriers such as triglycerides, microcrystalline cellulose, gum tragacanth or gelatin. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in: Remington's Pharmaceutical Sciences" by E. W. Martin, the contents of which are hereby incorporated by reference herein. Such compositions will contain a therapeutically effective amount of the polypeptide of the invention, preferably in a substantially purified form, together with a suitable amount of carrier so as to provide the form for proper administration to the subject.

According to an embodiment of the invention, pharmaceutical compositions contain 0.1%-95% of the polypeptide(s) of the present invention, derivatives, or analogs thereof. According to another embodiment of the invention, pharmaceutical compositions contain 1%-70% of the polypeptide(s) derivatives, or analogs thereof. According to another embodiment of the invention, the composition or formulation to be administered may contain a quantity of polypeptide(s), derivatives, or analogs thereof, according to embodiments of the invention in an amount effective to treat the condition or disease of the subject being treated.

An embodiment of the invention relates to polypeptides of the present invention, derivatives, or analogs thereof, presented in unit dosage form and prepared by any of the methods well known in the art of pharmacy. In an embodiment of the invention, the unit dosage form is in the form of a tablet, capsule, lozenge, wafer, patch, ampoule, vial or pre-filled syringe. In addition, in vitro assays may optionally be employed to help identify optimal dosage ranges. The precise dose to be employed in the formulation will also depend on the route of administration, and the nature of the disease or disorder, and should be decided according to the judgment of the practitioner and each patient's circumstances. Effective doses can be extrapolated from dose-response curves derived from in-vitro or in-vivo animal model test bioassays or systems.

According to one embodiment, the compositions of the present invention are administered in the form of a pharmaceutical composition comprising at least one of the active components of this invention together with a pharmaceutically acceptable carrier or diluent. In another embodiment, the compositions of this invention can be administered either individually or together in any conventional oral, parenteral or transdermal dosage form.

As used herein, the terms "administering," "administration," and like terms refer to any method which, in sound medical practice, delivers a composition containing an active agent to a subject in such a manner as to provide a therapeutic effect.

Depending on the location of the tissue of interest, the polypeptide of the present invention can be administered in any manner suitable for the provision of the polypeptides to cells within the tissue of interest. Thus, for example, a composition containing the polypeptides of the present invention can be introduced, for example, into the systemic circulation, which will distribute the peptide to the tissue of interest. Alternatively, a composition can be applied topically to the tissue of interest (e.g., injected, or pumped as a continuous infusion, or as a bolus within a tissue, applied to all or a portion of the surface of the skin, etc.).

In some embodiments, the pharmaceutical compositions comprising the polypeptides are administered via oral, rectal, vaginal, topical, nasal, ophthalmic, transdermal, subcutaneous, intramuscular, intraperitoneal or intravenous routes of administration. The route of administration of the pharmaceutical composition will depend on the disease or condition to be treated. Suitable routes of administration include, but are not limited to, parenteral injections, e.g., intradermal, intravenous, intramuscular, intralesional, subcutaneous, intrathecal, and any other mode of injection as known in the art. Although the bioavailability of peptides administered by other routes can be lower than when administered via parenteral injection, by using appropriate formulations it is envisaged that it will be possible to administer the compositions of the invention via transdermal, oral, rectal, vaginal, topical, nasal, inhalation and ocular modes of treatment. In addition, it may be desirable to introduce the pharmaceutical compositions of the invention by any suitable route, including intraventricular and intrathecal injection; intraventricular injection may be facilitated by an intraventricular catheter, for example, attached to a reservoir. Pulmonary administration can also be employed, e.g., by use of an inhaler or nebulizer.

For topical application, a peptide of the present invention, derivative, analog or a fragment thereof can be combined with a pharmaceutically acceptable carrier so that an effective dosage is delivered, based on the desired activity. The carrier can be in the form of, for example, and not by way of limitation, an ointment, cream, gel, paste, foam, aerosol, suppository, pad or gelled stick.

For oral applications, the pharmaceutical composition may be in the form of tablets or capsules, which can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate; or a glidant such as colloidal silicon dioxide. When the dosage unit form is a capsule, it can contain, in addition to materials of the above type, a liquid carrier such as fatty oil. In addition, dosage unit forms can contain various other materials which modify the physical form of the dosage unit, for example, coatings of sugar, shellac, or other enteric agents. The tablets of the invention can further be film coated.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes.

According to some embodiments, the peptides of the present invention, derivatives, or analogs thereof can be delivered in a controlled release system. In another embodiment, an infusion pump can be used to administer the peptide such as the one that is used, for example, for delivering insulin or chemotherapy to specific organs or tumors. In another embodiment, the peptides of the invention are administered in combination with a biodegradable, biocompatible polymeric implant, which releases the peptide over a controlled period of time at a selected site. Examples of preferred polymeric materials include, but are not limited to, polyanhydrides, polyorthoesters, polyglycolic acid, polylactic acid, polyethylene vinyl acetate, copolymers and blends thereof (See, Medical applications of controlled release, Langer and Wise (eds.), 1974, CRC Pres., Boca Raton, Fla., the contents of which are hereby incorporated by reference in their entirety). In yet another embodiment, a controlled release system can be placed in proximity to a therapeutic target, thus requiring only a fraction of the systemic dose.

The presently described peptides, derivatives, or analogs thereof may also be contained in artificially created structures such as liposomes, ISCOMS, slow-releasing particles, and other vehicles which increase the half-life of the peptides or polypeptides in serum. Liposomes include emulsions, foams, micelles, insoluble monolayers, liquid crystals, phospholipid dispersions, lamellar layers and the like. Liposomes for use with the presently described peptides are formed from standard vesicle-forming lipids which generally include neutral and negatively charged phospholipids and a sterol, such as cholesterol. The selection of lipids is generally determined by considerations such as liposome size and stability in the blood. A variety of methods are available for preparing liposomes as reviewed, for example, by Coligan, J. E. et al, Current Protocols in Protein Science, 1999, John Wiley & Sons, Inc., New York, and see also U.S. Pat. Nos. 4,235,871, 4,501,728, 4,837,028, and 5,019,369.

The compositions also include incorporation of the active material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance.

In one embodiment, the present invention provides combined preparations. In one embodiment, "a combined preparation" defines especially a "kit of parts" in the sense that the combination partners as defined above can be dosed independently or by use of different fixed combinations with distinguished amounts of the combination partners i.e., simultaneously, concurrently, separately or sequentially. In some embodiments, the parts of the kit of parts can then, e.g., be administered simultaneously or chronologically staggered, that is at different time points and with equal or different time intervals for any part of the kit of parts. The ratio of the total amounts of the combination partners, in some embodiments, can be administered in the combined preparation. In one embodiment, the combined preparation can be varied, e.g., in order to cope with the needs of a patient subpopulation to be treated or the needs of the single patient which different needs can be due to a particular disease, severity of a disease, age, sex, or body weight as can be readily made by a person skilled in the art.

In one embodiment, it will be appreciated that the peptides of the present invention can be provided to the individual with additional active agents to achieve an improved therapeutic effect as compared to treatment with each agent by itself. In another embodiment, measures (e.g., dosing and selection of the complementary agent) are taken to adverse side effects which are associated with combination therapies.

In one embodiment, depending on the severity and responsiveness of the condition to be treated, dosing can be of a single or a plurality of administrations, with course of treatment lasting from several days to several weeks or until cure is effected or diminution of the disease state is achieved.

In some embodiments, the peptides are administered in a therapeutically safe and effective amount. As used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used in the presently described manner. In another embodiment, a therapeutically effective amount of the polypeptide is the amount of the polypeptide necessary for the in vivo measurable expected biological effect. The actual amount administered, and the rate and time-course of administration, will depend on the nature and severity of the condition being treated. Prescription of treatment, e.g. decisions on dosage, timing, etc., is within the responsibility of general practitioners or specialists, and typically takes account of the disorder to be treated, the condition of the individual patient, the site of delivery, the method of administration and other factors known to practitioners. Examples of techniques and protocols can be found in Remington: The Science and Practice of Pharmacy, 21st Ed., Lippincott Williams & Wilkins, Philadelphia, Pa., (2005). In some embodiments, preparation of effective amount or dose can be estimated initially from in vitro assays. In one embodiment, a dose can be formulated in animal models and such information can be used to more accurately determine useful doses in humans.

In one embodiment, toxicity and therapeutic efficacy of the active ingredients described herein can be determined by standard pharmaceutical procedures in vitro, in cell cultures or experimental animals. In one embodiment, the data obtained from these in vitro and cell culture assays and animal studies can be used in formulating a range of dosage for use in human. In one embodiment, the dosages vary depending upon the dosage form employed and the route of administration utilized. In one embodiment, the exact formulation, route of administration and dosage can be chosen by the individual physician in view of the patient's condition. [See e.g., Fingl, et al., (1975) "The Pharmacological Basis of Therapeutics", Ch. 1 p.1].

Pharmaceutical compositions containing the presently described polypeptide as the active ingredient can be prepared according to conventional pharmaceutical compounding techniques. See, for example, Remington's Pharmaceutical Sciences, 18th Ed., Mack Publishing Co., Easton, Pa. (1990). See also, Remington: The Science and Practice of Pharmacy, 21st Ed., Lippincott Williams & Wilkins, Philadelphia, Pa. (2005).

In one embodiment, compositions including the preparation of the present invention formulated in a compatible pharmaceutical carrier are prepared, placed in an appropriate container, and labeled for treatment of an indicated condition.

In one embodiment, compositions of the present invention are presented in a pack or dispenser device, such as an FDA approved kit, which contain one or more unit dosages forms containing the active ingredient. In one embodiment, the pack, for example, comprises metal or plastic foil, such as a blister pack. In one embodiment, the pack or dispenser device is accompanied by instructions for administration. In one embodiment, the pack or dispenser is accommodated by a notice associated with the container in a form prescribed by a governmental agency regulating the manufacture, use or sale of pharmaceuticals, which notice is reflective of approval by the agency of the form of the compositions or human or veterinary administration. Such notice, in one embodiment, is labeling approved by the U.S. Food and Drug Administration for prescription drugs or of an approved product insert.

Use of the Compositions

According to some aspects, there is provided a method for treating, ameliorating, reducing and/or preventing a condition associated with increased bone resorption in a subject in need thereof, the method comprising the step of: administering to a subject a pharmaceutical composition comprising an effective amount of the polypeptide of the invention, thereby treating, ameliorating, reducing and/or preventing a condition associated with increased bone resorption in a subject in need thereof.

In some embodiments, there is provided a method for treating a disease associated with increased bone resorption in a subject in need thereof, the method comprising the step of administering to said subject a pharmaceutical composition comprising an effective amount of an amino acid molecule comprising the amino acid sequence selected from the group consisting of SEQ ID NOs: 11-17 and a pharmaceutical acceptable carrier, thereby treating, ameliorating, reducing and/or preventing a disease associated with increased bone resorption in a subject in need thereof.

In another embodiment, the polypeptide of the invention or a composition comprising the polypeptide is for use in treatment, amelioration, reduction, and/or prevention of a condition associated with increased bone resorption in a subject in need thereof. In some embodiments, there is provided a composition comprising an effective amount of polypeptide for use in the treatment or prevention of a disease associated with increased bone resorption in a subject in need thereof. In some embodiments, there is provided a composition comprising an effective amount of an amino acid molecule comprising the amino acid sequence selected from the group consisting of SEQ ID NOs: 11-17 for use in the treatment or prevention of a disease associated with increased bone resorption in a subject in need thereof.

In some embodiments, there is provided a use of a composition comprising an effective amount of polypeptide in the preparation of a medicament for the treatment, amelioration, reduction, or prevention of a disease associated with increased bone resorption in a subject in need thereof. In some embodiments, the invention provides use of a composition comprising an effective amount of an amino acid molecule comprising the amino acid sequence selected from the group consisting of SEQ ID NOs: 11-17 in the preparation of a medicament for the treatment of a disease associated with increased bone resorption in a subject in need thereof.

In one embodiment, the polypeptide of the present invention is provided to the subject per se. In one embodiment, the polypeptide of the present invention is provided to the subject as part of a pharmaceutical composition where it is mixed with a pharmaceutically acceptable carrier.

Non-limiting examples of disease associated with increased bone resorption include Paget's disease, osteoporosis, and tumor-linked bone resorption disease.

In some embodiments, the disease associated with increased bone resorption is osteoporosis.

The term "subject" as used herein refers to an animal, more particularly to non-human mammals and human organism. Non-human animal subjects may also include prenatal forms of animals, such as, e.g., embryos or fetuses. Non-limiting examples of non-human animals include: horse, cow, camel, goat, sheep, dog, cat, non-human primate, mouse, rat, rabbit, hamster, guinea pig, pig. In one embodiment, the subject is a human. Human subjects may also include fetuses. In one embodiment, a subject in need thereof is a subject afflicted with and/or at risk of being afflicted with a condition associated with increased bone resorption.

As used herein, the terms "treatment" or "treating" of a disease, disorder, or condition encompasses alleviation of at least one symptom thereof, a reduction in the severity thereof, or inhibition of the progression thereof. Treatment need not mean that the disease, disorder, or condition is totally cured. To be an effective treatment, a useful composition herein needs only to reduce the severity of a disease, disorder, or condition, reduce the severity of symptoms associated therewith, or provide improvement to a patient or subject's quality of life.

As used herein, the term "prevention" of a disease, disorder, or condition encompasses the delay, prevention, suppression, or inhibition of the onset of a disease, disorder, or condition. As used in accordance with the presently described subject matter, the term "prevention" relates to a process of prophylaxis in which a subject is exposed to the presently described peptides prior to the induction or onset of the disease/disorder process. This could be done where an individual has a genetic pedigree indicating a predisposition toward occurrence of the disease/disorder to be prevented. For example, this might be true of an individual whose ancestors show a predisposition toward certain types of, for example, inflammatory disorders. The term "suppression" is used to describe a condition wherein the disease/disorder process has already begun but obvious symptoms of the condition have yet to be realized. Thus, the cells of an individual may have the disease/disorder but no outside signs of the disease/disorder have yet been clinically recognized. In either case, the term prophylaxis can be applied to encompass both prevention and suppression. Conversely, the term "treatment" refers to the clinical application of active agents to combat an already existing condition whose clinical presentation has already been realized in a patient.

As used herein, the term "condition" includes anatomic and physiological deviations from the normal that constitute an impairment of the normal state of the living animal or one of its parts, that interrupts or modifies the performance of the bodily functions.

Any concentration ranges, percentage range, or ratio range recited herein are to be understood to include concentrations, percentages or ratios of any integer within that range and fractions thereof, such as one tenth and one hundredth of an integer, unless otherwise indicated.

Any number range recited herein relating to any physical feature, such as polymer subunits, size or thickness, are to be understood to include any integer within the recited range, unless otherwise indicated.

As used herein, the terms "subject" or "individual" or "animal" or "patient" or "mammal," refers to any subject, particularly a mammalian subject, for whom therapy is desired, for example, a human.

In the discussion unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the specification and claims is considered to be the inclusive "or" rather than the exclusive or, and indicates at least one of, or any combination of items it conjoins.

It should be understood that the terms "a" and "an" as used above and elsewhere herein refer to "one or more" of the enumerated components. It will be clear to one of ordinary skill in the art that the use of the singular includes the plural unless specifically stated otherwise. Therefore, the terms "a," "an" and "at least one" are used interchangeably in this application.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In the description and claims of the present application, each of the verbs, "comprise," "include" and "have" and conjugates thereof, are used to indicate that the object or objects of the verb are not necessarily a complete listing of components, elements or parts of the subject or subjects of the verb.

Other terms as used herein are meant to be defined by their well-known meanings in the art.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, C T (1994); Mishell and Shiigi (eds), "Strategies for Protein Purification and Characterization—A Laboratory Course Manual" CSHL Press (1996); "Bacteriophage Methods and Protocols", Volume 1: Isolation, Characterization, and Interactions, all of which are incorporated by reference. Other general references are provided throughout this document.

Various embodiments and aspects of the present invention as delineated hereinabove and as claimed in the claims section below find experimental support in the following examples. Reference is now made to the following examples, which together with the above descriptions illustrate some embodiments of the invention in a non-limiting fashion.

Materials and Methods

Methods Designing and Constructing M-CSF$_M$, Two M-CSF$_{RGD}$ Libraries and M-CSF$_{\alpha v\beta 3}$ Using the 3D structure of the murine c-FMS/M-CSF complex (PDB: 3EJJ) and the 3D structure of human M-CSF (PDB: 1HMC), the binding interface of the complex was identified. The M-CSF monomer, designated M-CSF$_M$, which is made up of 158 amino acids, was designed with C31 S mutation that prevents homo-dimerization of the monomer (see Deng, P., et al., Biochemical and biophysical research communications, 1996. 228(2): p. 557-566). Two libraries of M-CSF$_M$ variants were then designed such that the two loops distant from the receptor binding site (residue numbering according to PDB: 3EJJ 25 to 32 and 64 to 71, respectively) were each replaced with an RGD motif flanked by three random amino acids on each side represented as XXXRGDXXX (designated M-CSF$_{RGD}$). To generate the random amino acids in each library, the DNA codons were synthesized as NNS sequences, where N can be any codon and S can be C or G. The M-CSF$_M$ gene and the two M-CSF$_{RGD}$ libraries were prepared for us by GenScript (Piscataway, NJ, USA) with pCTCON homology sites and ECORI and NheI restriction sites on the amine terminal and AvrII and BamHI restriction sites on the C terminal. The M-CSF$_M$ gene and M-CSF$_{RGD}$ library DNA sequences were amplified by PCR with Phusion DNA polymerase (New England Biolabs, Ipswich, MA, USA) and transformed into EBY100 *Saccharomyces cerevisiae* strain with a modified linear pCTCON plasmid [48] for homologous recombination using a Micropulser electroporator (Bio-Rad, USA). The DNA sequences were recovered in the tryptophan-selective medium SDCAA (2% dextrose, 0.67% yeast nitrogen base, 0.5% bacto casamino acids, 1.47% sodium citrate, 0.429% citric acid monohydrate, pH 4.5). To evaluate the diversities (sizes) of the two M-CSF$_{RGD}$ libraries, the yeasts were plated on SDCAA plates (0.54% $Na_2HPO_4$, 0.856% $Na_2HPO_4 \cdot H_2O$, 18.2% sorbitol, 1.5% agar, 2% dextrose, 0.67% yeast nitrogen base, 0.5% bacto casamino acids) at several dilutions and were counted manually. Library 1 was made up of $3.6\times10^6$ variants, and library 2 of $8.3\times10^6$ variants. Combining the two libraries into one resulted in $1.1\times10^7$ variants. To evaluate the initial variability of the libraries, 20 clones from each library were sequenced by GenScript. After identifying the best binders for c-FMS and $\alpha_v\beta_3$ integrin, one of them (4.22) was chosen to be mutated to become a 43 integrin but not a c-FMS binder, referred as M-CSF$_{\alpha v\beta 3}$. Two single point mutations were designed in positions 9 and 15 by replacing histidine with alanine. M-CSF$_{\alpha v\beta 3}$ gene was purchased on a pCTCON vector from Biomatik (Wilmington, DE, USA).

Flow Cytometry Sorting and Analysis

For expressing the M-CSF$_M$ gene and the two M-CSF$_{RGD}$ libraries on the yeast surface, the SDCAA medium was replaced by SGCAA medium (2% galactose, 0.67% yeast nitrogen base, 0.5% bacto casamino acids, 1.47% sodium citrate, 0.429% citric acid monohydrate) and the yeasts were incubated overnight at 30° C. until the culture reached $OD_{600}$=10.0 ($10^8$ cells per ml). A number of cells equal to ten times the library size was added to 1 ml of PBS containing 1% bovine serum albumin (PBSA); the suspension was centrifuged, and the supernatant was removed. For binding analysis of M-CSF$_M$ and the M-CSF$_{RGD}$ libraries to c-FMS, yeast cells were incubated with mouse anti c-myc antibody, 9E10 (Abcam, Cambridge, MA, USA) in a 1:50 ratio and different concentrations of soluble Fc conjugated human c-FMS (R&D systems, USA) for 1 h at room temperature. After an additional washing step, cells were labeled with secondary PE anti mouse (Sigma-Aldrich, St. Louis, MO, USA) and goat anti human Fc FITC antibodies (Sigma-Aldrich) for 30 min at 4° C. in the dark. For binding analysis of M-CSF$_{RGD}$ libraries to integrin, the experiment was performed with integrin binding buffer (IBB; 20 mM Tris, pH7.5, 2 mM $CaCl_2$, 100 mM NaCl, 1 mM $MgCl_2$, and 1 mM $MnCl_2$)+1% BSA. The yeast cells were incubated with chicken anti c-myc and different concentrations of soluble human $\alpha_v\beta_3$ integrin (R&D Systems, Minneapolis, MN, USA) for 1 h. After an additional washing step, cells were labeled with secondary PE-anti-chicken and FITC-anti-human $\beta_3$ integrin (BioLegend, San Diego, CA, USA) antibodies for 30 min in the dark. Labeled cells were washed with 1 ml of PBSA or IBB+1% BSA. A total of 5 rounds of affinity maturation sorting were performed; in each sort a diagonal shape was created in order to enrich the high protein binders. In each sort, 0.5% to 2% of the population was collected into a new tube containing SDCC media. The first sort was performed against 500 nM c-FMS (sort 0) and the subsequent sorts against 500 nM $\alpha_v\beta_3$ integrin (sort 1), 250 nM $\alpha_v\beta_3$ integrin (sort 2), 100 nM $\alpha_v\beta_3$ integrin (sort 3), 20 nM $\alpha_v\beta_3$ integrin (sort 4), and 50 nM of c-FMS (sort 5) The high affinity binders were enriched using a iCyt Synergy FACS apparatus (Sony Biotechnology, San Jose, CA, USA).

Choosing and Identifying High-Affinity $\alpha_v\beta_3$ Integrin and c-FMS Binders To identify the high αvβ3 integrin and c-FMS binders, 25 different clones from sort 4 and 25 different clones from sort 5 were tested for binding to 20 nM of $\alpha_v\beta_3$ integrin, as described in the flow cytometry sorting section. Then, 10 $\alpha_v\beta_3$ integrin binding clones from sort 4 and 10 $\alpha_v\beta_3$ integrin binding clones from sort 5 having the highest affinities to $\alpha_v\beta_3$ integrin were analyzed for binding to 50 nM of c-FMS.

The clones with the highest affinity for both $\alpha_v\beta_3$ integrin and c-FMS were selected, and DNA was extracted from these clones using Zymoprep™ Yeast Plasmid Miniprep I (Zymo Research, Irvine, CA, USA) according to the manufacturer's protocol. The extracted plasmids were incubated with *Escherichia-coli* competent cells for 30 min on ice and transferred into 0.2-cm gap cuvettes (Bio-Rad, USA). The cuvettes were inserted into a Micropulser electroporator (Bio-Rad, USA) and pulsed with 2.5 kV. Immediately, 1 ml of warm Luria Broth (LB) medium was added to each cuvette, and the suspensions were incubated at 37° C. for 1 h. The bacteria were seeded and grown overnight on LB agar plates containing 1:1000 ampicillin at 37° C. Colonies were moved to LB medium with ampicillin and grown overnight. The plasmids were extracted from the bacterial culture with HiYield plasmid mini kit (RBC, Bioscience, Taiwan) according to the manufacturer's protocol. The purified plasmids were sequenced to confirm that they contained the desired sequence and to prevent repetitions. To determine the binding specificity to other RGD binding integrins, namely $\alpha_4\beta_7$, $\alpha_2\beta_{2b}$, $\alpha_5\beta_1$ and $\alpha_v\beta_5$ (BioLegend, USA), the three chosen M-CSF$_{RGD}$ variants (4.22, 4.24 and 5.6) were analyzed for binding to 250 nM of each integrin. To detect integrin binding, M-CSF$_{RGD}$ variants were incubated with APC anti-human CD49d, APC anti-human CD41, FITC anti-human CD49e and FITC anti-human CD5, respectively (BioLegend, USA) and analyzed with Accuri C6 flow cytometry analyzer (BD Biosciences, San Jose, CA, USA).

Purification of Proteins

The three M-CSF$_{RGD}$ variants (4.22, 4.24 and 5.6), M-CSF$_M$ and M-CSF$_{\alpha v\beta 3}$ were digested with ECORI and AvrII (New England Biolabs, USA) and ligated with Quick Ligase (New England Biolabs, USA) to the pPICK9K expression plasmid containing a FLAG tag in the N-terminus and 6×His tag in the C-terminus of the cloning site. The plasmids were transformed into competent *E. coli* and sequenced with AOX1 forward and reverse primers as previously described. The plasmids with the desired sequence were linearized with SacI restriction enzyme (New England Biolabs, USA) and transformed into *Pichia pastoris* strain GS 115 using the multi-copy *Pichia* Expression Kit (Invitrogen, USA). After transformation, the cells were plated on RDB plates (18.6% sorbitol, 2% agar, 2% dextrose, 1.34% yeast nitrogen base, $4\times10^{-5}$% biotin and $5\times10^{-3}$% each of L-glutamic acid, L-methionine, L-leucine, L-lysine, and L-isoleucine) for 48 h at 30° C., collected, and plated again on Geneticin (G418 4 mg/ml) plates for an additional 48-72 h. Colonies were moved to 5 ml of BMGY medium (2% peptone, 1% yeast extract, 0.2% $K_2H(PO_4)$, 1.1812% $KH_2(PO_4)$, 1.34% yeast nitrogen base, $4\times10^{-5}$% biotin, 1% glycerol), incubated overnight at 30° C., and transformed into 5 ml of BMMY medium (2% peptone, 1% yeast extract, 0.23% $K_2H(PO_4)$, 1.1812% $KH_2(PO_4)$, 1.34% yeast nitrogen base, $4\times10^{-5}$% biotin, 0.5% methanol) for 3 days at 30° C. Each day, methanol was added to the BMMY medium to maintain the concentration at 0.5%. For small-scale protein expression, the GS 115 cells were centrifuged at 3 800 g for 10 min, and the supernatant was collected for western blot analysis using 1:1000 primary mouse anti-FLAG (Sigma-Aldrich, USA), followed by 1:5000 anti-mouse secondary antibody conjugated to alkaline phosphatase (Jackson ImmunoResearch, West Grove, PA, USA), and 2 ml of BCIP reagent for signal development (Sigma-Aldrich, USA). The highest expressing culture was grown in 50 ml of BMGY overnight at 30° C. and transferred to 500 ml of BMMY. Each day (for 3 days), methanol was added to the BMMY medium to maintain the concentration at 0.5%. Then, cells were concentrated at 3800 rpm for 10 minutes and the supernatant was filtered using 0.22-μm stericups (Millipore, Ecuador). NaCl was added to the filtrate to a final concentration of 150-300 mM, imidazole was added to a final concentration of 10 mM, and the pH was adjusted to 8.0. The protein solution was incubated for 1 h at 4° C., centrifuged at 3800 g for 10 min, and filtered again. The filtrate was loaded on a HisTrap Ni column (GE Healthcare Life Sciences, UK) using a peristaltic pump. The column was washed with binding buffer (20 mM $NaH_2PO_4 \cdot H_2O$, 500 mM NaCl, and 10 mM imidazole; pH 8) and eluted with elution buffer (20 mM $NaH_2PO_4 \cdot H_2O$, 500 mM NaCl, and 500 mM imidazole; pH 8). The elution buffer was removed by Vivaspin (GE Healthcare Life Sciences, UK) with a 3,000 Da cutoff, and the buffer was replaced with PBS. Protein N-glycosylations were removed by overnight treatment with the endoglycosidase Endo HF (New England Biolabs, USA) at room temperature. Proteins were further purified on an ÄKTA pure 150 FPLC with a Superdex 200 16/600 size exclusion column, and the elution times were compared to those for protein standards. Purified protein samples were subjected to mass spectrometry analysis (Ilse Katz Institute for Nanoscale Science and Technology, BGU) and to SDS-PAGE coomassie blue staining with Instant Blue (Expedeon, San Diego, CA, USA) to evaluate protein purity. Proteins concentrations were measured using an Evolution 260 bio spectrophotometer (Thermo Fisher Scientific, USA) based on protein absorption at 280 nm and extinction coefficient of 13,325 $M^{-1}$ $cm^{-1}$ for M-CSF$_M$ and M-CSF$_{RGD}$ variant 4.22. Extinction coefficient for M-CSF$_{\alpha v\beta 3}$ and M-CSF$_{RGD}$ variants 4.24 and 5.6 is 14,815 $M^{-1}$ $cm^{-1}$.

Circular Dichroism (CD) Analysis

Secondary structural analysis of the purified proteins was performed using a J-815 CD spectrometer (JASCO, Tokyo, Japan) with a 1-mm path length quartz cuvette. Spectra of 5 μM of purified protein in 400 μl of PBS were obtained at room temperature. The average of three spectra was normalized to obtain ellipticity (degree×$cm^2$/dmol) and the PBS background was subtracted. Data points with a diode voltage >1000 V were excluded. For determining M-CSF$_M$ melting temperature, 5 μM of M-CSF$_M$ was tested as described and the sample temperature was elevated from 10° C. to 95° C. in a stepwise manner and the spectra was obtained. For protein denaturation that is consisting mostly of α-helix secondary structures the wave length that was observed was 209 nm.

Chemical Cross Linking

Purified M-CSF$_M$, M-CSF$_{RGD}$ variants and M-CSF$_{\alpha v\beta 3}$ were incubated with different concentrations of $BS^3$ [bis (sulfosuccinimidyl)suberate, Thermo Fisher Scientific, Waltham, MA, USA] cross linker 0-2500 μM for 30 min at room temperature. Then, Tris was added to a final concentration of 30 mM and the mixture was incubated for 15 min at room temperature. Samples were denaturized and loaded on 15% SDS-PAGE. The gels were stained with coomassie blue (InstantBlue, Expedeon, CA, USA) and visualized with MiniBis pro (DNR Bio-Imaging Systems, Jerusalem, Israel).

Surface Plasmon Resonance (SPR)

Determination of binding of the soluble purified proteins (M-CSFM and M-CSF$_{RGD}$ variants) to c-FMS and $\alpha_v\beta_3$ integrin was performed on a ProteOn XPR36 (Bio-Rad, USA). The M-CSF$_{RGD}$, M-CSF$_M$ and M-CSF$_{\alpha v\beta 3}$ protein variants were immobilized on the surface of the chip by using the amine coupling reagents sulfo-NHS (0.1 M N-hydroxysuccinimide) and EDC (0.4 M 1-ethyl-3-(3 dimethylaminopropyl)-carbodiimide), Bio-Rad, USA). To attach the M-CSF$_{RGD}$, M-CSFM and M-CSF$_{\alpha v\beta 3}$ variants covalently to the chip, 1 μg of each protein and 3 μg of BSA in 10 mM sodium acetate buffer, pH 4.0, were used to give 474, 900 1329, 1272 and 1337 response units (RU) for M-CSF$_{M}$, M-CSF$_{\alpha v\beta 3}$ 4.22, 4.24 and 5.6 respectively. Unbound esters were deactivated with 1 M ethanolamine HCl at pH 8.5, and the temperature was set at 25° C. Then, the chip was rotated, and the human c-FMS soluble proteins (Sino Biological, China) were allowed to flow over the chip at 6 different concentrations (0, 12.5, 25, 50, 100 and 200 nM) at a flow rate of 50 μl/min for 490 s, followed by dissociation for 600 s in PBS+0.005% Tween (PBST). For determining $\alpha_v\beta_3$ integrin binding, the chip was regenerated using 50 mM NaOH at a flow rate of 100 μl/min and analyzed again for c-FMS binding to make sure that the chip had been regenerated. After making sure the chip is regenerated, and different concentrations of 43 integrin proteins (0, 12.5, 25, 50, 100 and 200 nM) were allowed to flow over the chip. The interactions obtained were normalized to the initial protein binding RUs to the chip surface. Then, for each concentration, the $K_D$ was obtained from the equilibrium binding phase of the sensorgram. To determine the $\alpha_v\beta_3$ integrin specificity for each M-CSF$_{RGD}$ variant, a new chip was loaded with different RGD binding integrins, as follows: 8.5 μg of $\alpha_3\beta_1$, 8.5 μg of $\alpha_4\beta_7$, 6 μg of $\alpha_5\beta_1$, 8.5 μg of $\alpha_v\beta_5$, and 8.5 μg of $\alpha_v\beta_3$ integrin and 3 μg of BSA as a negative control. The proteins were covalently bound to the chip with 10 mM sodium acetate buffer, pH 4.0 as described above. Then, 1 μM of the M-CSF$_{RGD}$ variant was allowed to flow over the chip at a rate of 50 μl/min for 409 s, followed by 600 s of dissociation with PBS+1% Tween. The interactions obtained were normalized to the initial protein binding RUs to the chip surface. To achieve statistical significance, we made sure that the $\chi^2$ values were at least 10% or lower than the $R_{max}$ values.

Direct Cell Binding Assays

M-CSF$_{M}$ and two variants of M-CSF$_{RGD}$ (4.22 and 5.6) were labeled with a molar ratio of 1:1 of DyLight™ 488 NHS Ester (Thermo Fisher Scientific, USA) and the purified protein. The solution was incubated for 1 h at room temperature and the residual unbound dye was washed three times with Vivaspin (GE Healthcare life sciences, UK) with a 3,000 Da cutoff. M-CSF$_{RGD}$ variant 4.24 and M-CSF$_{\alpha v\beta 3}$ were not tested for direct cell binding due to low protein purification yields. MDA-MB-231 breast cancer cells were used for direct cell binding of the purified proteins. Cells were plated at a density of $10^5$ per well in 96-well plates and were washed with 1 ml of PBSA 0.1%. The cells were centrifuged at 150 g for 5 min, and the supernatant was removed; this step was repeated twice. Then, the labeled M-CSF$_{RGD}$ protein variants and the M-CSF$_{M}$ monospecific control were added in IBB+1% BSA to the cells at different concentrations (1, 2.5 and 7.5 μM) in a total volume of 100 μl and incubated at 4° C. with gentle agitation for 2 h. For c-FMS expression, the cells were stained with PE-anti human CD115 (BioLegend, USA) at a dilution of 1:50 and for $\alpha_v\beta_3$ integrin expression with FITC-anti human $\beta_3$ integrin (BioLegend, USA) at a dilution of 1:25 for 30 min. Then, the cells were washed twice as described above and analyzed with Accuri C6 flow cytometry analyzer (BD Biosciences, USA). The mean fluorescence of the cells was subtracted from the other samples. The experiment was repeated three times at each concentration.

Murine bone marrow derived monocytes (BMMs) were obtained by flushing the bone marrow from the femur and tibia of WT C57BL6 mice. The cells were treated with ACK red lysis buffer (Thermo Fisher Scientific, USA) and plated on bacterial culture dishes in αMEM growth medium (Biological Industries, Israel) containing recombinant murine M-CSF (40 ng/ml) (R&D systems, USA). The cells were incubated for 3 days at 37° C. under 5% $CO_2$ to induce monocyte adhesion and proliferation. The plates were washed with PBS, the cells were detached using a cell scraper, and $10^5$ cells were transferred to each well in a 96-well plate. The cells were washed twice with 200 μl of 0.1% PBSA. Binding was determined as described for labeled M-CSF$_{M}$ and the M-CSF$_{RGD}$ proteins. For murine c-FMS expression, anti-mouse CD115 (CSF-1R) (BioLegend, USA) was used at 1:50 concentration and detected with goat anti-rat (PE) antibody (Abcam, USA). For $\alpha_v\beta_3$ integrin expression, the Alexa Fluor® 488 anti-mouse/rat CD61 (BioLegend, USA) antibody was used as previously described. Samples were analyzed with Accuri C6 flow cytometry analyzer (BD Biosciences, USA). The experiment was repeated three times at each concentration.

Primary cells differentiation assay—Murine primary cells were obtained as described in the murine primary cells section. Cells were washed with PBS and detached using a cell scraper, and 20,000 cells were plated in each well of a 96-well plate. Osteoclast differentiation was induced by culturing the cells in α-MEM containing 10% of fetal bovine serum (FBS), penicillin and streptomycin, 20 ng/μl M-CSF and 20 ng/ul RANKL (R&D Systems, USA). To determine the influence of the M-CSF$_{RGD}$ variants and the M-CSF$_{M}$ on the osteoclasts, the proteins were added to the differentiation medium (with M-CSF and RANKL) in three different concentrations (50 nM, 1 μM and 5 μM). After 72-96 h, once the cells had differentiated fully, they were fixated with 4% paraformaldehyde and stained using the tartrate-resistant acid phosphatase (TRAP) staining kit (Sigma-Aldrich, USA) according to manufacturer's protocol. As a positive control, PBS was used instead of the inhibitors, and negative controls comprised cells incubated in differentiation medium without RANKL and inhibitors. Osteoclast parameters were obtained by analysis of 20 images from random areas in each well; the osteoclasts were observed with an Olympus ×83 microscope with an automated stage. Cells in each image were counted in a double-blind manner and the number of nuclei in the osteoclasts and the total osteoclast surface area were determined using ImageJ software. Three repeats were performed for every condition, and each repeat was normalized to the positive control values.

Statistical analysis—The data from the primary cells differentiation assay was analyzed for column statistics with GraphPad Prism version 5.00 for Windows (La Jolla, CA, USA). Data is shown as mean±SEM. Statistical significance was determined by column statistics and t test analysis. P value<0.05 was considered statistically significant.

Crystallization and structure determination—M-CSF$_{C31S}$ was concentrated to 5.5 mg/ml. Initial crystallization-conditions screening was performed using an Index screening kit (Hampton Research) at 293 K. Each drop contained a mixture of 0.3 μl of crystallization solution and 0.3 μl of M-CSF$_{C31S}$ protein solution. Crystals grew for 9 days and were harvested from a drop containing the following optimized crystallization solution: 0.03 M bis-Tris, pH 6.5; 0.17 M Mg formate; 16.67% PEG 3350; 0.07 M bis-Tris, pH 5.5. The crystals were flash-cooled in liquid nitrogen prior to data collection. A diffraction dataset was collected on beamline BM14 at the European Synchrotron Radiation Facility (ESRF, Grenoble, France) to a maximum resolution of 2 Å. Data was measured at 0.979 Å for 250 images with an oscillation range of 1°, an exposure time of 3 s per image and a crystal-to-detector distance of 181.45 mm. Data processing was performed using the HKL2000 program suite (Otwinowski, Z. and Minor, W. (1997) 276, 307-326). Phase acquisitions and structure determination were performed using Phaser (McCoy, A. J., Grosse-Kunstleve, R. W., Adams, P. D., Winn, M. D., Storoni, L. C. and Read, R. J. (2007) Phaser crystallographic software. J. Appl. Crystallogr. 40, 658-674) of the CCP4 Program Suite (Winn, M. D., Ballard, C. C., Cowtan, K. D., Dodson, E. J., Emsley, P., Evans, P. R. et al. (2011) Overview of the CCP 4 suite and current developments. Acta Crystallogr. Sect. D 67, 235-242). The final model was built by Coot (Emsley, P. and Cowtan, K. (2004) Coot: model-building tools for molecular graphics. Acta Crystallogr. Sect. D Biol. Crystallogr. 60, 2126-2132) and refined using Phenix (Adams, P. D., Afonine, P. V., Bunkóczi, G., Chen, V. B., Davis, LW., Echols, N. et al. (2010) PHENIX: a comprehensive Python-based system for macromolecular structure solution. Acta Crystallogr. Sect. D Biol. Crystallogr. 66, 213-221).

Energy calculations to identify the M-$CSF_{C31S}$ residues that contribute significantly to dimer formation—The per-residue contributions of the M-$CSF_{C31S}$ residues to dimer formation was analyzed, as described in Kosloff, M., et. al. (2011; Nat. Struct. Mol. Biol. 18, 846-853). The finite difference Poisson-Boltzmann (FDPB) method was used to calculate the net electrostatic and polar contributions ($\Delta\Delta G_{elec}$) of each residue that is within 15 Å of the dimer interface. Non-polar energy contributions ($\Delta\Delta G_{np}$) were calculated as a surface-area proportional term, by multiplying the per-residue surface area buried upon complex formation [calculated using surfv (Sridharan, S., Nicholls, A., Honig, B., Nicholls, A. and Honig, B. (1992). FASEB J.] by a surface tension constant of 0.05 kcal/mol/Å (Sheinerman, F. B., Al-Lazikani, B. and Honig, B. (2003) Sequence, structure and energetic determinants of phosphopeptide selectivity of SH2 domains. J. Mol. Biol. 334, 823 841). Energetically significant residues were defined as those contributing $\Delta\Delta G_{elec}$ or $\Delta\Delta G_{np}$>1 kcal/mol to the interactions.

Protein expression and purification—The three computationally selected M-CSF variants, namely, M-$CSF_{C31S,Q26R}$, M-$CSF_{C31S,M27R}$ and M-$CSF_{C31S,Q26R,M27R}$, as well as M-$CSF_{C31S}$ and M-$CSF_{WT}$, were purified using GS 115 *Pichia pastoris* yeast strain as previously described (Rosenfeld, L., Shirian, J., Zur, Y., Levaot, N., Shifman, J. M. and Papo, N. (2015) Combinatorial and computational approaches to identify interactions of macrophage colony-stimulating factor (M-CSF) and its receptor c-FMS. J. Biol. Chem. 290, 26180-26193). M-$CSF_{C31S}$ and M-$CSF_{WT}$ were ultimately purified using a Superdex 200 16/600 column (GE Healthcare), while M-$CSF_{C31S,M27R}$, M-$CSF_{C31S,Q26R}$ and M-$CSF_{C31S,Q26R,M27R}$ were purified using a Superdex 75 10/300 column (GE Healthcare).

$BS^3$ crosslinking assay—Human (4 µg) and murine M-$CSF_{WT}$ (1 µg), M-$CSF_{C31S}$ (1 µg) and M-$CSF_{C31S,M27R}$ (2.5 µg) were incubated with different concentrations of $BS^3$ [bis(sulfosuccinimidyl)suberate] (ThermoFisher Scientific, MA, USA) cross linker (0, 25 µM, 100 µM, 250 µM, 500 µM, 1000 µM and 2500 µM) for 30 min at room temperature. Then, bis-Tris buffer was added to a final concentration of 30 mM, and the mixture was incubated for 15 min at room temperature. Samples were denaturized with sample buffer, boiled, and loaded on 15% SDS-PAGE for protein separation. The gels were stained with InstantBlue staining (Expedeon, CA, USA) for 40 min, followed by two washing steps with double distilled water. The gels were visualized with MiniBis pro (DNR Bio-Imaging Systems, Jerusalem, Israel).

Dynamic light scattering (DLS)—The hydrodynamic radii of M-$CSF_{WT}$, M-$CSF_{C31S}$ and M-$CSF_{C31S,M27R}$ were determined using DLS. The proteins, in a concentration of 0.5 mg/ml, were filtered to remove aggregates and contaminants. Light scattering was measured at an angle of 90° three times, in two different experiments, resulting in a total of six measurements. Another measurement was performed at an angle of 60° to verify that the radius did not change with the measurement angle. An analysis of the solution was conducted to verify that the most abundant specie was in the size range of 1-10 nm. The peak for this specie was compared for the three different proteins, and the hydrodynamic radius of each was determined as the maximum of the peak.

Small angle X-ray scattering (SAXS) analysis—SAXS data were collected on SAXLAB GANESHA 300 XL system, possessing a Genix 3D Cu-source with an integrated monochromator, three pinholes collimation and a two-dimensional Pilatus 300K detector. The scattering intensity was recorded in the interval 0.012<q<0.7 Å−1. The measurements were performed under vacuum at 25° C. All three M-CSF variants were measured at concentrations of 3, 5 and 7 mg/ml. The scattering of the buffer was also measured and subtracted from the scattering of the samples. The magnitude of the scattering vector is described by the following equation:

$$q = \frac{4\pi\sin\theta}{\lambda}$$

where 2θ is the scattering angle, and λ is the wavelength.

Values for the radius of gyration ($R_g$) were derived from the small angle part of the SAXS profile (Guinier region, $qR_g$<1.0), in PRIMUS [43]. In this region, Guinier approximation is applicable:

$$I(q) = I(0)e^{\frac{-R_g^2q^2}{3}}$$

$R_g$ values were also derived using in-house scripts [44] designed to perform an automatic search for the best fitting parameters using GNOM (Svergun, D. I. (1992). J. Appl. Crystallogr. 25, 495-503). CRYSOL (Barberato, C., Barberato, C. and Koch, M. H. J. (1995) J. Appl. Crystallogr. 28, 768-773) was used to compute the theoretical SAXS spectra based on the M-$CSF_{WT}$ crystal structure (PDB ID code: 3UF2). These spectra served as a reference for reconstruction of the experimental SAXS data. GASBOR (Svergun, D. I., Petoukhov, M. V. and Koch, M. H. J. (2001) Biophys. J. 80, 2946-2953) was used to reconstruct the molecular envelope based on the best GNOM fit obtained from the in-house script. Ten models were calculated for each sample and averaged using DAMAVER (Volkov, V. V. and Svergun, D. I. (2003) J. Appl. Crystallogr. 36, 860-864).

Surface plasmon resonance (SPR)—The ability of M-$CSF_{WT}$ and M-$CSF_{C31S,M27R}$ to bind the c-FMS receptor was determined by SPR spectroscopy on a ProteOn XPR36 (Bio-Rad, CA, USA). M-CSF variants were immobilized on the surface of the chip by using the amine coupling reagents, sulfo-NHS (0.1 M N-hydroxysuccinimide) and EDC (0.4 M 1-ethyl-3-(3-dimethylaminopropyl)-carbodiimide). For chip activation, followed by 1 µg of the proteins in 10 mM sodium acetate buffer, pH 4.0, to give 1063 and 551 response units (RU) for M-$CSF_{WT}$ and M-$CSF_{C31S,M27R}$, respectively. BSA (3 µg; 3762 RU) was immobilized on the chip as a negative control. Unbound esters were deactivated with 1 M ethanolamine HCl at pH 8.5. Before each binding assay, the temperature was set at 25° C. Soluble human c-FMS receptor (extracellular domains, residues Met1-Glu512) (Sino Biological, China) was then allowed to flow over the surface-bound M-CSF, at concentrations of 4.375, 8.75, 17.5, 35 and 70 nM and a flow rate of 25 μl/min for 16 min 21 s, and during this time the interactions between M-CSF and c-FMS were measured. The dissociation of the proteins was measured, while allowing PBST (phosphate buffered saline+ 0.005% Tween) to flow over the surface for 6 min and 50 s at a flow rate of 50 μl/min. This process was repeated three times, with a regeneration step between runs. The regeneration was conducted with 50 mM NaOH at a flow rate of 100 μl/min. For each protein complex, a sensorgram was generated from the RUs measured during the course of the protein-protein interaction minus the values of the BSA channel. The dissociation constant ($K_D$) was determined from the sensorgram of the equilibrium binding phase.

Phosphorylation assay—The experiment was performed on two cell types, BMMs and human peripheral blood $CD14^+$ monocytes, as follows: (i) BMMs from wild-type C57BL6 mice were purified by flushing the bone marrow from the femur and tibia as previously described (Levaot, N., Simoncic, P. D., Dimitriou, I.D., Scoffer, A., La Rose, J., Ng, A. H. M. et al. (2011) J. Clin. Invest. 121, 3244-3257). The cells were treated with ACK red cells lysis buffer (ThermoFisher Scientific, USA) and grown in complete α-MEM growth medium (Sigma-Aldrich, USA) containing 10% fetal bovine serum (FBS) (selected to not contain LPS to prevent macrophage differentiation), penicillin, streptomycin and L-glutamine. Recombinant murine M-CSF was added at a concentration of 40 ng/ml (Peprotech, Israel) for three days at 37° C. to induce adhesion and proliferation of monocytes. Then, $7\times10^5$ cells were transferred into a 6-well plate with complete α-MEM and 20 ng/ml murine M-CSF and RANKL (R&D Systems, USA) for 48 h. (ii) CD $14^+$ monocytes (Lonza, Switzerland) were grown in complete α-MEM medium for five days in the presence of human M-CSF (20 ng/mL). Then, $3.5\times10^5$ cells were transferred to a 24-well plate with complete α-MEM medium, 20 ng/μl human M-CSF (R&D Systems, USA) and 20 ng/ml murine RANKL for 72 h. At this point, the medium was replaced with a starvation medium (α-MEM without FBS) for 4 h. After starvation, the cells were washed with PBS and incubated in a starvation medium containing 0.5 nM murine (BMMs) or human (CD14+) M-CSF and 100 nM ($CD14^+$ cells) or 1 μM (BMMs) of either M-$CSF_{C31S}$ or M-$CSF_{C31S,M27R}$ for 1 min. To test the phosphorylation levels in the absence of murine M-$CSF_{WT}$, we incubated 0.5, 5, 10, 50, 1000 and 5000 nM of M-$CSF_{C31S}$ or M-$CSF_{C31S,M27R}$ and 0.5,5.10 nM of human M-$CSF_{WT}$ with the cells. The positive control contained 0.5 nM murine (BMMs) or human ($CD14^+$) M-CSF, and the negative control was incubated in starvation medium without any added protein. The cells were transferred to ice, and lysis buffer (deoxycholate 0.5%, 25 nM NaF, 10 mM $NaPO_4$, 1 mM sodium orthovanadate, 5 mM EDTA, pH 7.4, 5 mM EGTA, pH 7.4, 100 mM NaCl, 2% Triton X-100) was added. The cells were detached, collected, incubated on ice for 10 min, centrifuged at 14,000 g for 30 min and the supernatants were transferred to a fresh tube. Western blot was performed on all samples, with anti-c-FMS, anti-phosphorylated c-FMS, or anti-β-actin antibody produced in rabbit as a primary antibody (Cell Signaling Technologies, MA, USA). A secondary HRP-linked anti-rabbit antibody was then added, and the signal was developed using EZ-ECL kit (Biological Industries, Israel). The chemiluminescent signal was imaged with Fusion FX (Vilber Lourmat, Germany). The images were quantified using ImageJ. The quantified intensity values of the phosphorylated c-FMS for each sample were divided by the total c-FMS intensity, and then by the β-actin expression intensity. The value of the positive control was set as 1, and other samples were normalized according to it.

Differentiation assay—BMMs and CD14+ cells were obtained and grown as described above. The plates containing the monocytes were washed with PBS; the cells were detached using a cell scraper for BMMs or Accutase (Biological industries, Israel) for $CD14^+$; and $2\times10^4$ BMMs or $1\times10^4$ $CD14^+$ cells were transferred to each well in a 96-well plate. Osteoclast differentiation was induced as described in the 'phosphorylation assay' section. To determine the influence of M-$CSF_{C31S}$ and the M-$CSF_{C31S,M27R}$ on osteoclast differentiation, the proteins were added to the differentiation medium (with M-CSF and RANKL) in different concentrations (50 nM, 1 μM and 5 μM for BMMs and 50 nM, 250 nM and 1 μM for $CD14^+$). To determine the influence of human M-$CSF_{WT}$ on the differentiation, it was added to the cells in different concentrations (50 nM 1 μM and 5 μM) without adding murine M-$CSF_{WT}$. Once the cells were fully differentiated, they were fixed with 4% paraformaldehyde and stained using the tartrate-resistant acid phosphatase (TRAP) staining kit (Sigma-Aldrich, USA) according to the manufacturer's protocol. As the positive control, cells were incubated with M-CSF and RANKL without inhibitors, and the negative control was comprised of cells that were incubated in differentiation medium without RANKL. Osteoclast parameters were obtained by analysis of 20 images from random areas in each well; the osteoclasts were observed with an Olympus ×83 microscope with an automated stage. Cells in each image were counted in a double-blind manner, and the number of nuclei in the osteoclasts was determined using ImageJ software. For the positive control of BMMs, an average of 28.33 osteoclasts and 135 nuclei per well were counted. For $CD14^+$ positive control, the average numbers of osteoclasts and nuclei were 14.5 and 75, respectively, per well. The results for each parameter were normalized to the positive control values.

The data from the c-FMS phosphorylation assay and cell differentiation assays was analyzed for column statistics with GraphPad Prism version 5.00 for Windows (La Jolla, CA, USA). Data is shown as means±SEM or means±SD. Statistical significance was determined by column statistics and t-test analysis. A P value<0.05 was considered statistically significant.

Example 1

Engineering a Monomeric M-CSF that Binds c-FMS

As known in the art, M-CSF glycoprotein is secreted as a homodimer that, upon binding to two c-FMS receptors, induces c-FMS auto-phosphorylation, followed by activation of downstream signaling pathways. Further, it was previously disclosed that cysteine in position 31 of M-CSF plays a critical role in M-CSF dimerization and activation of c-FMS (see Deng, P., et al., Biochemical and biophysical research communications, 1996. 228(2): p. 557-566).

In order to generate an M-CSF which acts as antagonist of c-FMS, the ability of M-CSF to dimerize was impaired. A mutant M-CSF with diminished dimerization capability (designated M-CSFM) was generated by replacing the cysteine at position 31 of a 158 amino acid long M-CSF (see SEQ ID NO: 18, FIG. 1A) with a serine residue as set forth in SEQ ID NO: 2

(EEVSEYCSHMIGSGHLQSLQRLIDSQMETSSQITFEFVDQEQLKDPVCYL
KKAFLLVQDIMEDTMRFRDNTPNAIAIVQLQELSLRLKSCFTKDYEEHDKA
CVRTFYETPLQLLEKVKNVFNETKNLLDKDWNIFSKNCNNSFAECSSQGHE
RQSEGS).

The compatibility of the M-CSFM/c-FMS system with the yeast surface display (YSD) method was evaluated by transforming the M-$CSF_M$ gene into *Saccharomyces cerevisiae* and evaluating proteins expression and binding.

In order to evaluate the binding affinity of M-$CSF_M$ for c-FMS on the YSD system, apparent binding of M-$CSF_M$ to different concentrations of soluble c-FMS was examined. Cells expressing M-$CSF_M$ on the cell wall were incubated with 10 different concentrations of c-FMS-Fc (0.5 nM to 2000 nM) and were tested for binding with flow cytometry. The resulting curve has a good fit for a single site-binding curve and the apparent KD is 20 nM (FIG. 2). The resulting $K_D$ value ($k_D$=20 nM) resembled a $K_D$ value which was previously disclosed in the art ($K_D$=13.6 nM, see Elegheert, J., et al., Nat Struct Mol Biol, 2012. 19(9): p. 938-47).

Next, a binding specificity of the M-$CSF_M$ to c-FMS was evaluated. For this purpose, the ability of M-$CSF_M$ to bind a c-kit receptor, which is a c-FMS structural homolog, was utilized. Result demonstrated that M-$CSF_M$ did not bind c-kit receptor even at high concentrations of 200 nM (data not shown). These results demonstrated that M-$CSF_M$ exhibits high binding and high specificity to c-FMS.

Example 2

Engineering and Selection of Monomeric M-CSF and M-CSF Harboring RGD Motif Proteins with High Affinity for c-FMS and $\alpha_v\beta_3$ Integrin Previous studies disclosed that M-CSF signaling through its receptor c-FMS regulates bone resorption by a cross-talk with signaling activated by αvβ3 integrin. Therefore, experiments to rule out an ability of M-$CSF_M$ to bind αvβ3 integrin, were conducted. Results demonstrated that the M-CSFM did not bind αvβ3 integrin, even at high concentrations of 200 nM.

In order to construct a dual-specific M-CSF monomer that can bind both c-FMS and αvβ3 integrin, one of two loops on the M-$CSF_M$ (SEQ ID NO: 2) scaffold, were replaced with RGD, a motif crucial for αvβ3 integrin ligand binding, flanked by three random amino acids on each side, namely, by XXXRGDXXX, where X represents any random amino acid (designated M-$CSF_{RGD}$). Library 1 is a library of constructs in which residues 25-32 were replaced with the RGD motif (SEQ ID NO: 19, FIG. 1B). Library 2 represents a library of constructs in which residues 64-71, were replaced with RGD motif. The different constructs and their properties are illustrated in FIGS. 3A-D.

Figure 4:
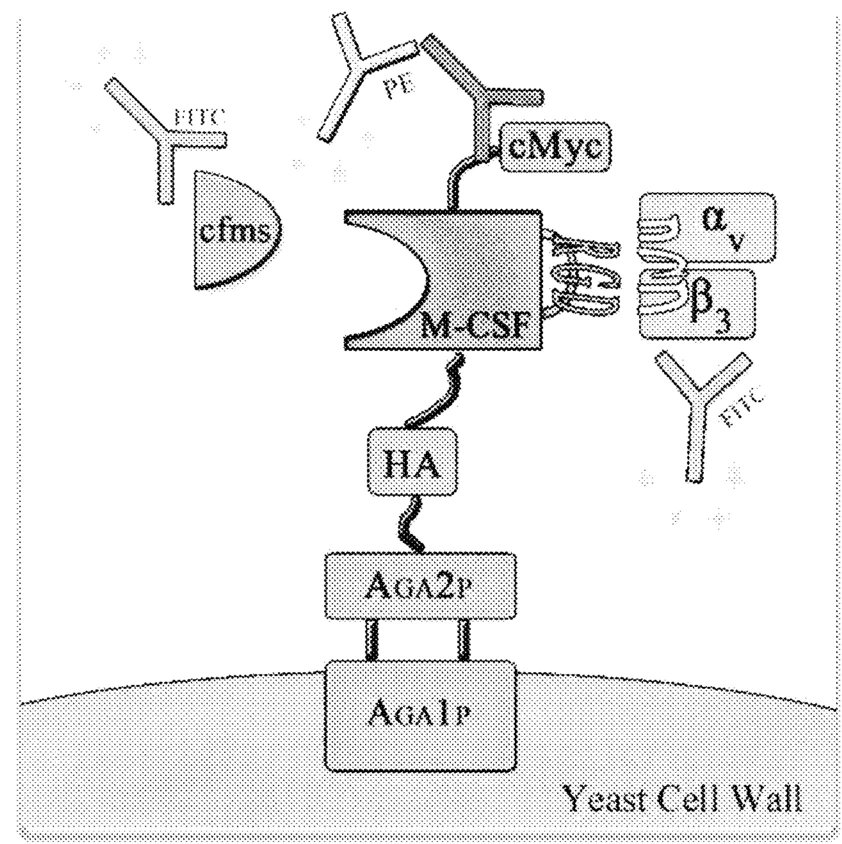
FIG. 4 is a schematic illustration of yeast surface display (YSD) construct.
Figure 5A:
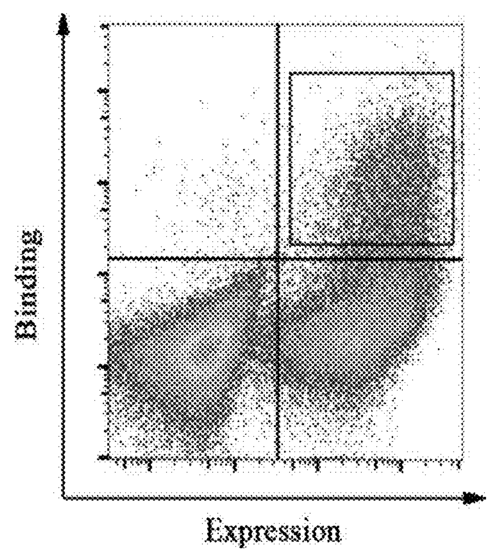
FIGS. 5A-5F show FACS dot plots of M-CSF$_{RGD}$ affinity maturation process in which yeast displayed mutant pools were tested for binding to (5A) 200 nM c-FMS, (5B) 500 nM αvβ3 integrin, (5C) 250 nM $\alpha_v\beta_3$ integrin, (5D) 100 nM $\alpha_v\beta_3$ integrin, (5E) 20 nM $\alpha_v\beta_3$ integrin, and (5F) 50 nM c-FMS, high target binders were collected as demonstrated in each figure with black polygon shape gates.
Figure 5B:
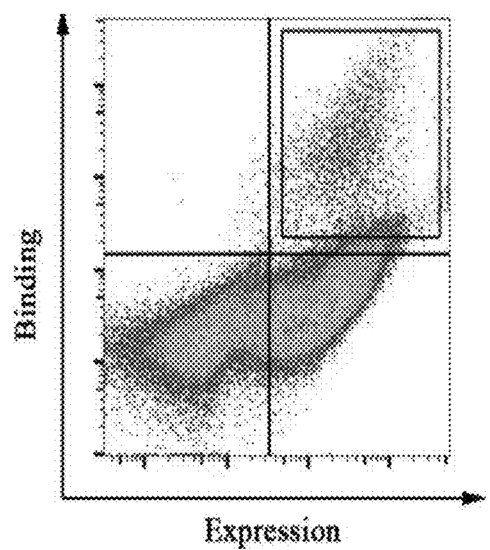
Figure 5C:
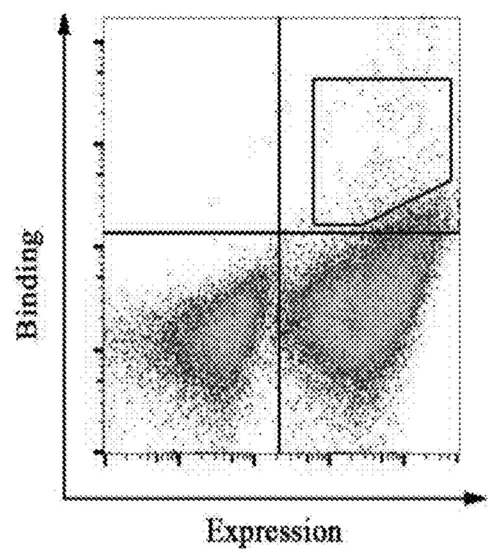
Figure 5D:
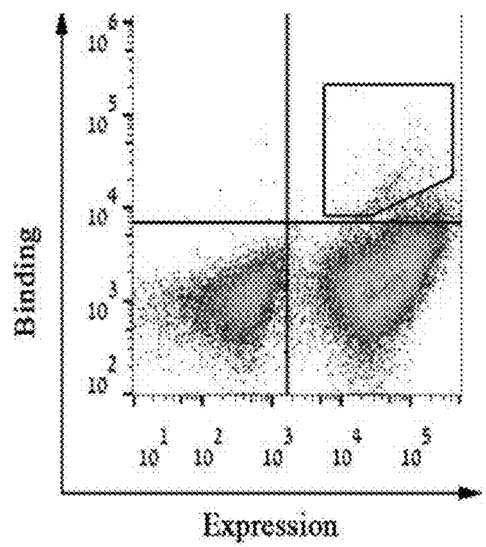
Figure 5E:
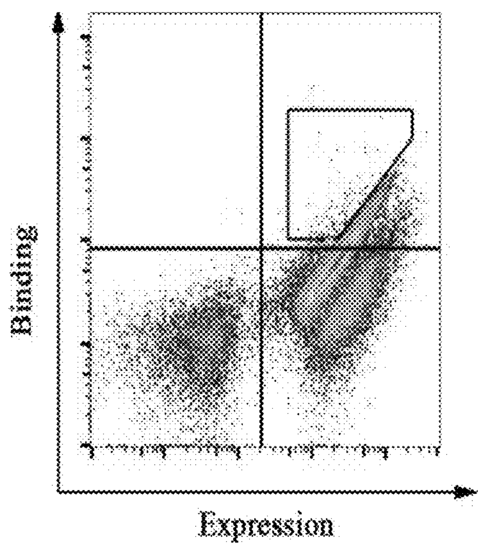
Figure 5F:
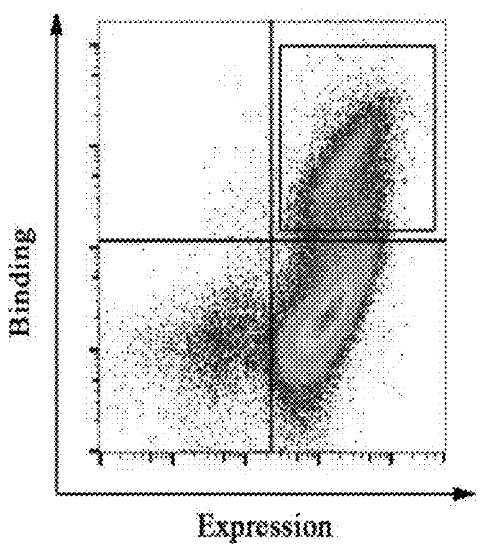
Figure 6A:
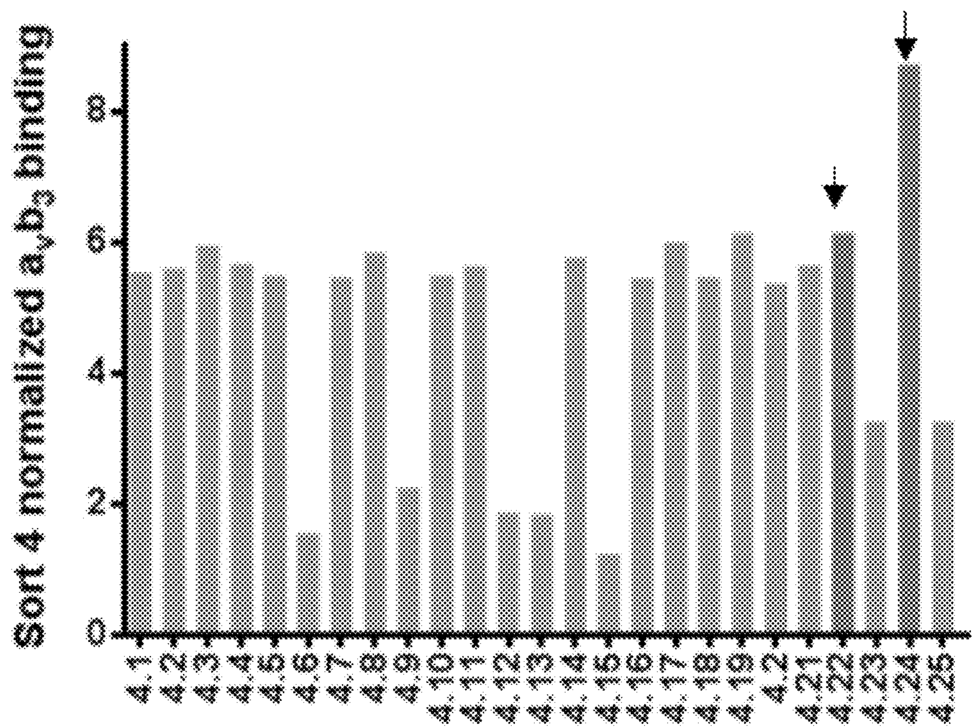
FIGS. 6A-6D are bar graphs showing normalized binding values of individual YSD M-CSF$_{RGD}$ clones to $\alpha_v\beta_3$ integrin and c-FMS: twenty-five different clones from each of sorts four (6A) and five (6C) were tested for binding to 20 nM of $\alpha_v\beta_3$ integrin, results are normalized to the lowest binder, Next, the best 15 $\alpha_v\beta_3$ integrin M-CSF$_{RGD}$ binders from sort four (6B) and the best ten $\alpha_v\beta_3$ integrin M-CSF$_{RGD}$ binders from sort five (6D), were tested for binding to 50 nM of c-FMS, these results are normalized to M-CSF$_{M}$, the chosen clones (4.22, 4.24 and 5.6) are marked by arrows.
Figure 6B:
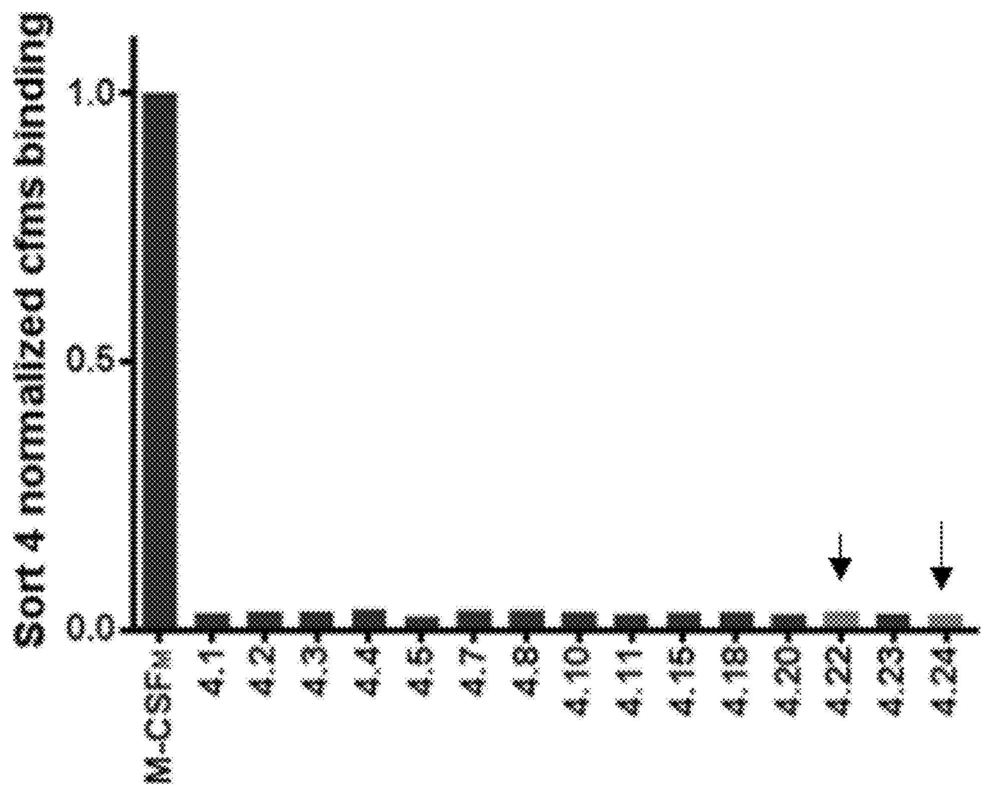
Figure 6C:
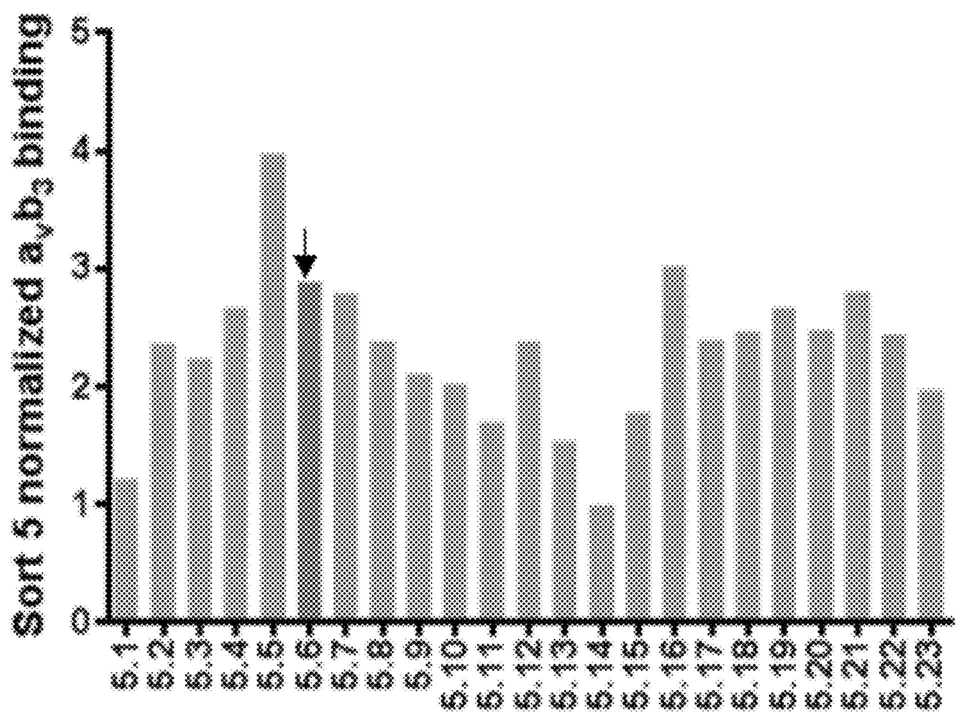
Figure 6D:
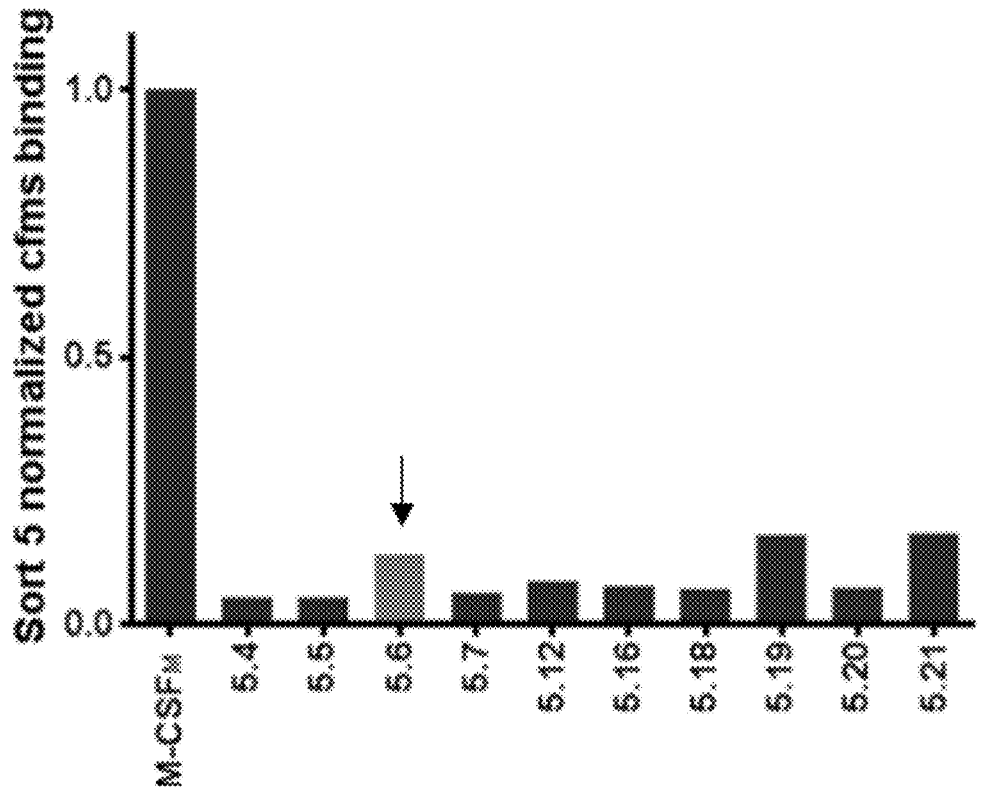

In order to identify and isolate M-CSF variants with a high affinity for both c-FMS and $\alpha_v\beta_3$ integrin, a YSD complex, that enables separation high-affinity clones from low-affinity clones by using flow cytometry, was constructed. The M-$CSF_{RGD}$ library was covalently linked to Aga1p and the yeast cell wall. Binding for c-FMS was determined with c-FMS-Fc recombinant protein and goat anti human Fc FITC conjugated secondary antibody and the expression levels were measured with a mouse anti c-myc primary antibody and PE anti mouse secondary antibody. For $\alpha_v\beta_3$ integrin binding, yeasts were incubated with recombinant 43 integrin and mouse anti human CD49d FITC secondary antibody and the expression levels were measured with chicken anti c-myc primary antibody and PE goat anti chicken secondary antibody (FIG. 4).

Following verification that M-$CSF_{RGD}$ was well expressed on the surface of the yeast cell wall and that the libraries did indeed bind 500 nM soluble c-FMS and 500 nM $\alpha_v\beta_3$ integrin, the two libraries were merged (in 1:1 ratio in terms of expression) and considered as a single library that consisted of $1.1\times10^7$ variants. In order to enrich a population of high affinity $\alpha_v\beta_3$ integrin binders, the YSD library was incubated with different concentrations of $\alpha_v\beta_3$ integrin and specific antibody (anti c-myc) to detect expression. Next, fluorescent labeled secondary antibodies (fluorescein isothiocyanate (FITC) anti human $\beta_3$) were added to detect integrin binding and protein complex expression (phycoerythrin (PE)). Subsequently, the high affinity binders were isolated into a fresh tube by FACS using a diagonal shape to normalize protein binding to their copy number expression on the yeast cell wall. The library was enriched and the process was repeated a total of five times. In order to enrich for $\alpha_v\beta_3$ integrin and c-FMS binding, the first sort was done with 500 nM c-FMS to make sure that library binding to c-FMS is not lost, and the four subsequent sorts with 500 nM, 250 nM, 100 nM and 20 nM $\alpha_v\beta_3$ integrin to isolate the best integrin binders. Following the fourth sort, an improvement in $\alpha_v\beta_3$ integrin binding and reduction in c-FMS binding was observed. Subsequently, in order to restore c-FMS binding, last sort was performed against 50 nM of c-FMS (FIGS. 5A-F).

In order to identify specific variants that would bind both c-FMS and $\alpha_v\beta_3$ integrin, $\alpha_v\beta_3$ integrin binding of 50 different variants from sorts four and five was first determined. The resulting best 25 $\alpha_v\beta_3$ integrin binders were next tested for c-FMS binding (FIGS. 6A-D). Three unique binders that showed both high c-FMS binding and high $\alpha_v\beta_3$ integrin binding. These M-$CSF_{RGD}$ variants were designated 4.22, 4.24 (both from sort four), and 5.6 (from sort five) (FIG. 1D). The sequences of the three selected variants (4.22, 4.24, and 5.6) did not have any mutation other than the RGD binding loop.

To test whether these variants selectively bind only $\alpha_v\beta_3$ integrin, binding of the three M-$CSF_{RGD}$ variants to $\alpha_v\beta_3$, $\alpha_4\beta_7$, $\alpha_{2\beta}2_b$ and $\alpha_5\beta_1$ integrins (250 nM) was tested. All three variants showed high specificity for $\alpha_v\beta_3$ integrin and were therefore regarded as good candidates for osteoclast-specific drug development, since osteoclasts express high levels of $\alpha_v\beta_3$ integrin as early as 48 hours of differentiation.

Results further demonstrated that variant 5.6 had a higher affinity for c-FMS than for $\alpha_v\beta_3$ integrin; variant 4.24 had a higher affinity for $\alpha_v\beta_3$ integrin than for c-FMS; and variant 4.22 had intermediate binding affinities for both c-FMS and $\alpha_v\beta_3$ integrin. In addition, 4.22 and 5.6 were representatives from a loop 1 libraries and 4.24 was a representative from a loop 2 library. Using the YSD system, it was further demonstrated that the three M-$CSF_{RGD}$ variants (4.22, 4.24 and 5.6) could simultaneously bind c-FMS and $\alpha_v\beta_3$ integrin by showing that their binding intensities to c-FMS and $\alpha_v\beta_3$ integrin each alone was equal to the intensity of binding to the two receptors simultaneously (data not shown). The fact that the binding intensity of the M-$CSF_{RGD}$ variants to c-FMS and $\alpha_v\beta_3$ integrin does not decrease when binding both compared to binding of one of them suggests that one receptor does not interfere sterically with the binding of the other and thus the binding of the developed inhibitor to one target will not inhibit its binding to the other target.

Example 3

Production, Purification and Evaluation of M-CSF$_M$ and M-CSF$_{RGD}$ Variants

Figure 7A:
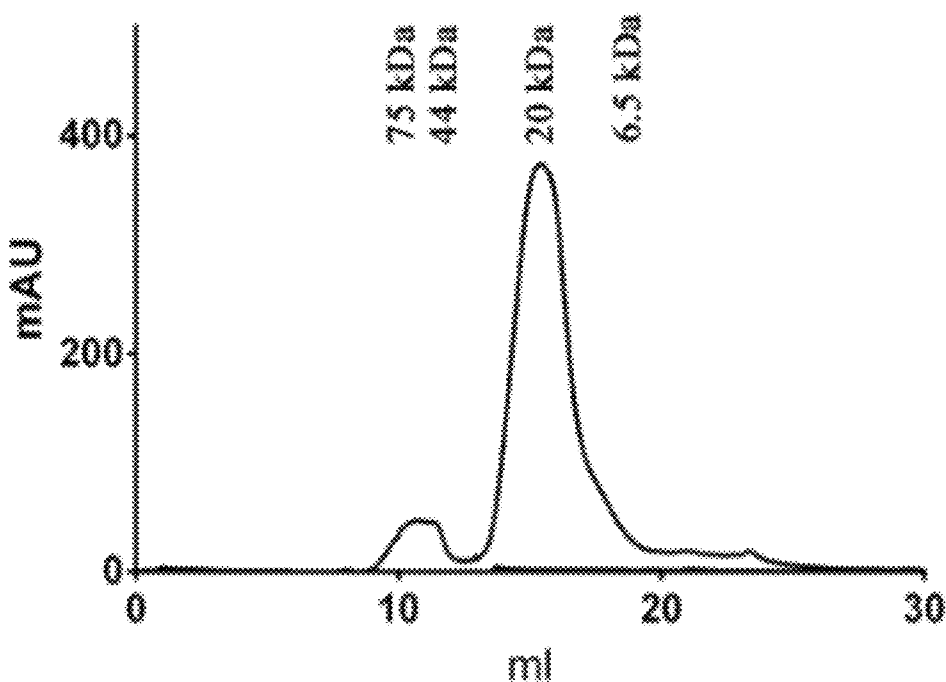
FIGS. 7A-7D depict the protein purification process of M-CSF$_{M}$ and M-CSF$_{RGD}$ variants: (7A) is a graph representing results of size exclusion chromatography of non-glycosylated M-CSF$_{RGD}$ clone 4.22 eluted at the size of 21 kDa with high molecular weight standards, (7B) is a graph showing CD spectra of non-glycosylated M-CSF$_{M}$, non-glycosylated 4.22, non-glycosylated 4.24 and non-glycosylated 5.6. (7C) is a graph representing results of mass spectrometry spectrum for non-glycosylated 5.6. (7D) is a photograph of SDS PAGE for all purified proteins: glycosylated M-CSF$_{M}$ (lane 1), non-glycosylated M-CSF$_{M}$ (lane 2), non-glycosylated 4.22 (lane 3), non-glycosylated 4.24 (lane 4) and non-glycosylated 5.6 (lane 5)
Figure 7B:
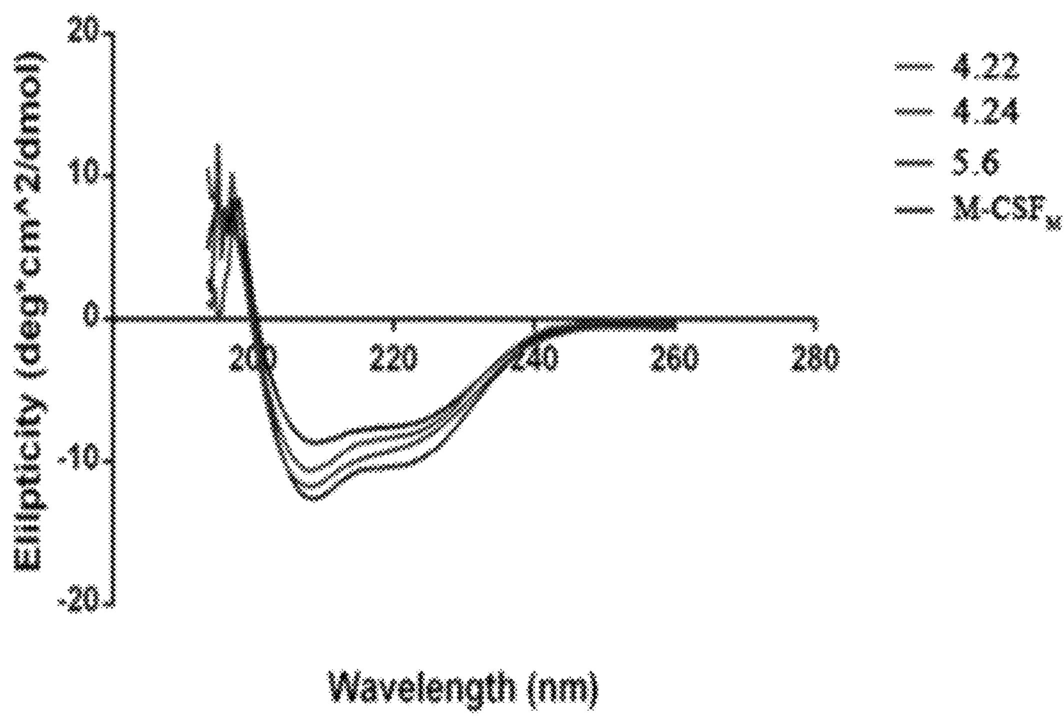
Figure 7C:
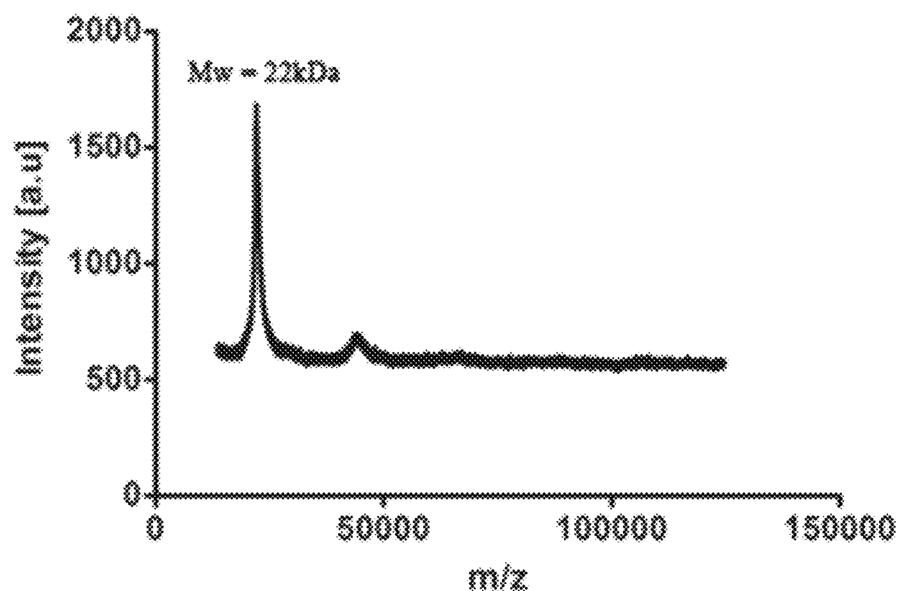
Figure 7D:
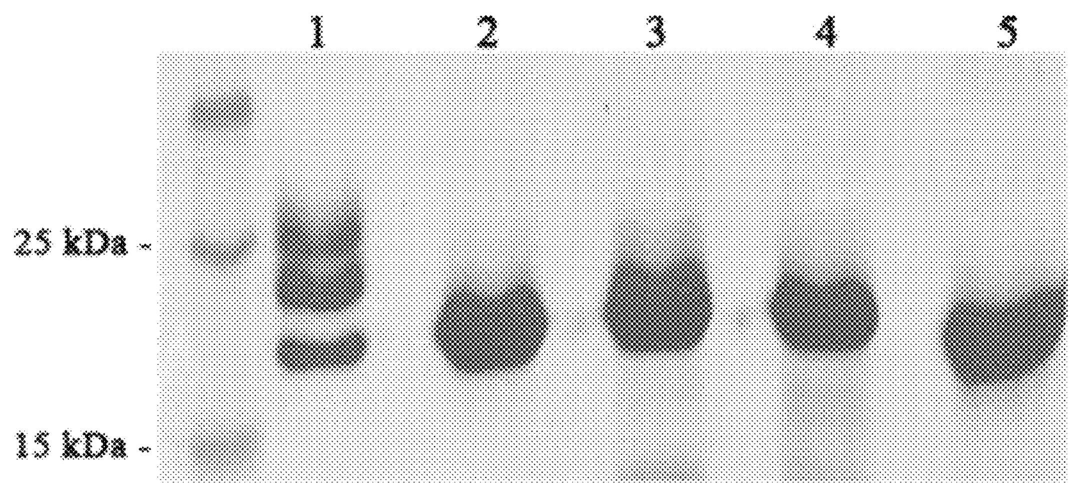
Figure 9A:
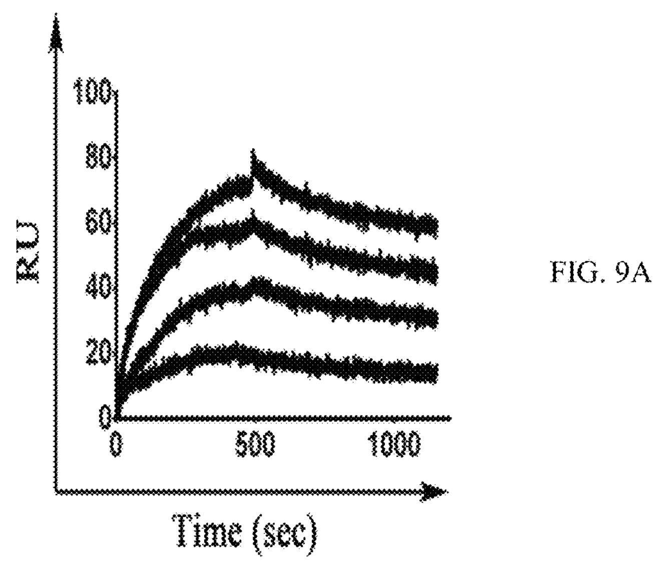
FIGS. 9A-9J show SPR sensorgrams of the different M-CSF purified proteins: binding of M-CSF$_{M}$ (9A and 9E), M-CSF$_{\alpha v\beta 3}$ (9B and 9G) 4.22 (9C and 9H), 4.24 (9D and 9I) and 5.6 (9E and 9J) to c-FMS (9A-9E) and 43 integrin (9F-9J) at concentrations of 12.5 nM, 25 nM, 50 nM, 100 nM and 200 nM.
Figure 9B:
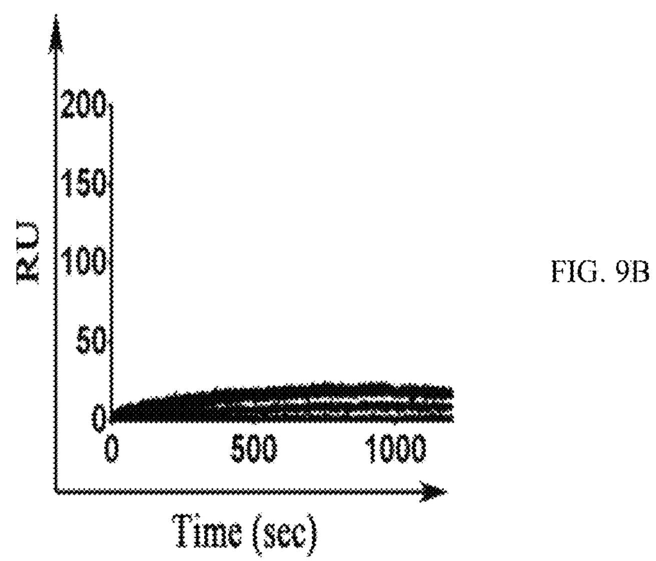
Figure 9C:
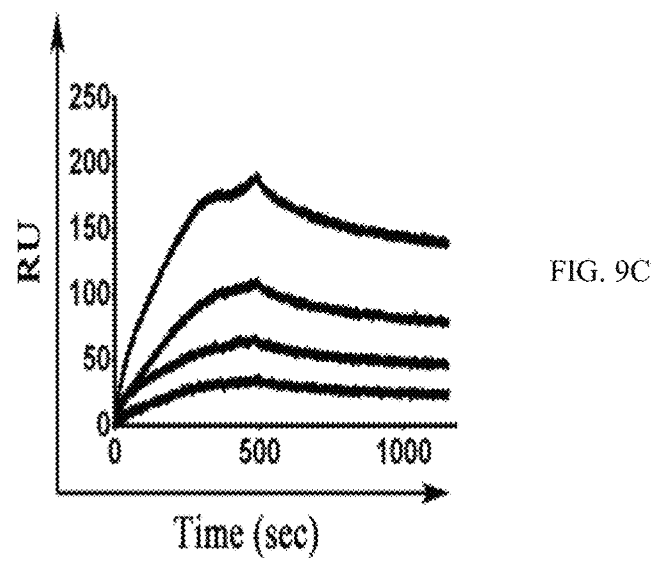
Figure 9D:
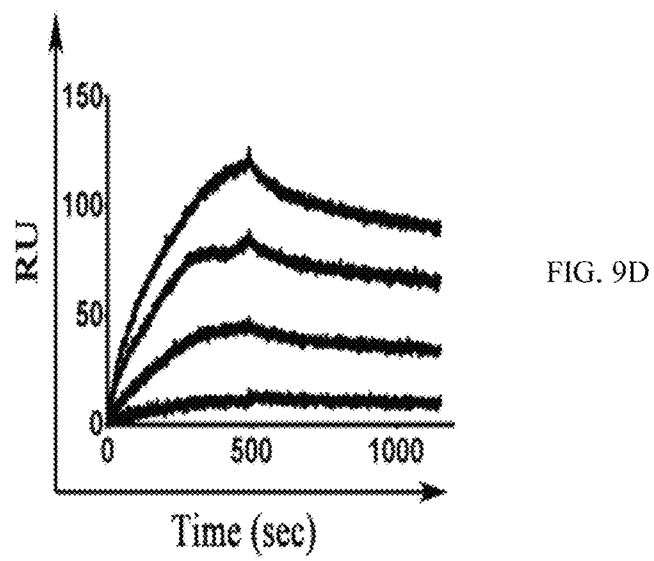
Figure 9E:
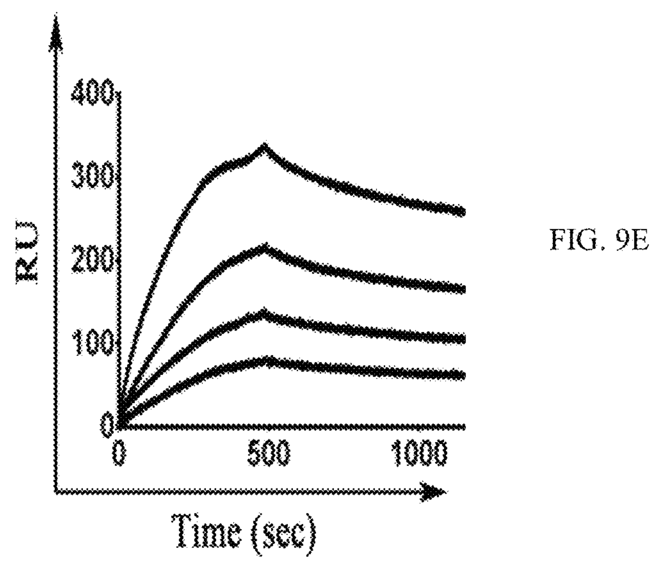
Figure 9F:
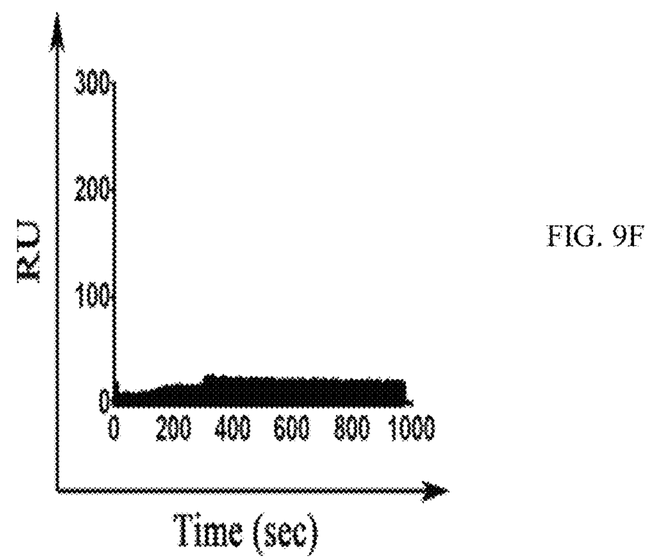
Figure 9G:
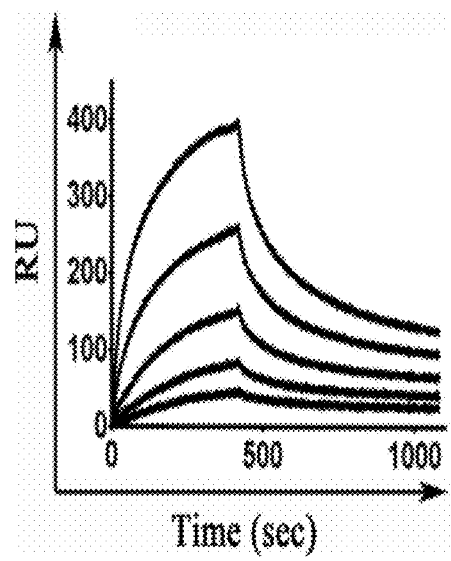
Figure 9H:
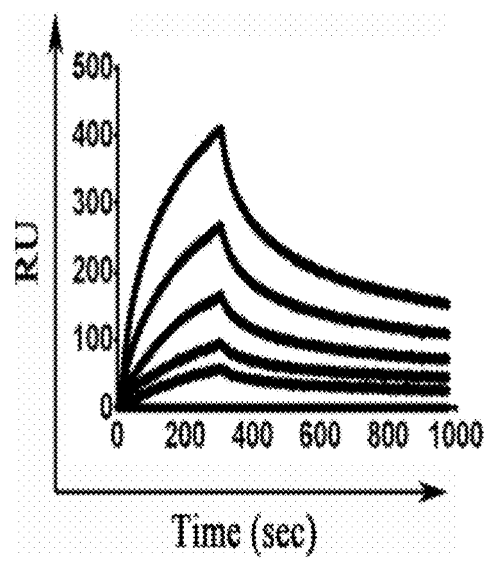
Figure 9I:
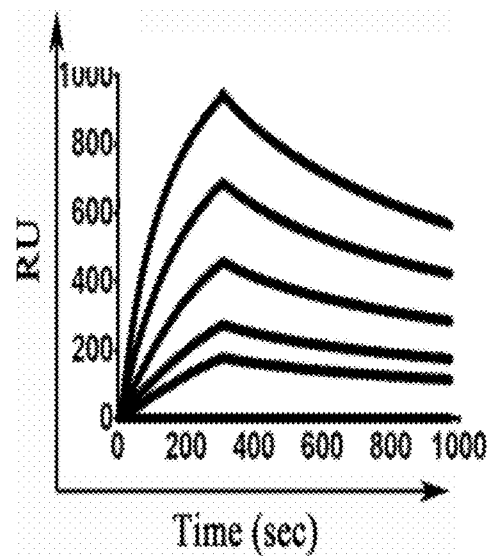
Figure 9J:
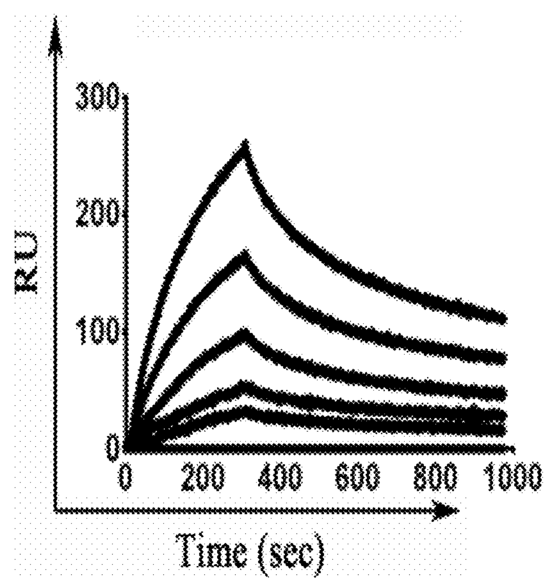

M-CSF$_M$ and the M-CSF$_{RGD}$ variants were purified and characterized in their soluble forms. Experiments were conducted to confirm that M-CSF glycosylation do not affect protein binding and signaling. Glycosylated variants of M-CSF$_M$ and the M-CSF$_{RGD}$ (i.e., having two glycosylation sites in positions 122 and 140) and non-glycosylated variants of M-CSF$_M$ and the M-CSF$_{RGD}$ (obtained from an endoglycosidase reaction) were expressed in a *Pichia pastoris* and purified by using affinity chromatography as a first step. Next, the glycosylated and non-glycosylated M-CSF$_M$ and M-CSF$_{RGD}$ variants were loaded on a size exclusion chromatography column, and eluted in the expected size of approximately 21 kDa (FIG. 7A). SDS-PAGE analysis of the purified proteins showed that the non-glycosylated M-CSF$_M$ migrated with the expected size of ~21 kDa. Three bands were obtained for the glycosylated M-CSF$_M$, one of 21 kDa and two higher ones for the two glycosylation sites. Circular dichroism (CD) spectra of the purified proteins showed similar curves corresponding to a protein that is consists of mostly α-helix motifs, meaning that the glycosylation and the RGD loops did not change the protein secondary structure. Moreover, the mutation C31 S in M-CSF$_M$ did not change the protein secondary structure. To reduce immunogenicity that might interfere in the in vitro and in vivo studies, the M-CSF$_{RGD}$ proteins were therefore purified in the non-glycosylated form. The exact mass of the purified proteins was determined used mass spectrometry (MS): the expected molecular weight of 21.6 kDa was obtained for M-CSF$_M$; the molecular weights for the M-CSF$_{RGD}$ variants were: 21.7 kDa for 4.22, 21.7 kDa for 4.24 and 22 kDa for 5.6.

Example 4

Purified M-CSF$_M$ Maintains Partial Dimerization and the M-CSF$_{RGD}$ and M-CSF$_{\alpha v\beta 3}$ Variants Dimerization is Abolished Experiments were conducted in order to verify that the purified variants are incapable of dimerizing. The purified variants were incubated with a cross linker reagent ($BS^3$ [bis(sulfosuccinimidyl)suberate]) to enhance and visualize non-covalent intermolecular interactions. Following incubation, the reactions were stopped and the samples were loaded in denaturized conditions on a protein gel. As expected, the three M-CSF$_{RGD}$ variants (4.22, 4.24, and 5.6) and the M-CSF$_{\alpha v\beta 3}$ did not show any dimerization even at a very high $BS^3$ concentration of 2500 μM. In contrast, M-CSF$_M$ did still exhibit some dimerization interactions at all $BS^3$ concentrations (FIG. 8). This finding suggests that M-CSF$_M$ maintained some dimerization capabilities and therefore is not suitable for development as a c-FMS inhibitor. The other purified proteins, M-CSF$_{RGD}$ and M-CSF$_{\alpha v\beta 3}$, did not show any dimerization and therefore have potential for development as good antagonists to c-FMS signaling.

Example 5

Purified Proteins Bind c-FMS and $\alpha_v\beta_3$ Integrin with Different Affinities Typically, a good competitor for native protein receptors should exhibit a higher binding affinity ($K_D$) than the binding affinities of their natural ligands. The $K_D$ of M-CSF to c-FMS receptor lies in the low nano molar range (13.6 nM). The binding affinities of $\alpha_v\beta_3$ integrin are 40.7 nM and 157.8 nM to vitronectin (one of its ligands) and to the inhibitor, cRGDfV, respectively. In order to demonstrate that the purified proteins bind their targets and to determine the binding affinities to their targets, $\alpha_v\beta_3$ integrin and c-FMS, surface plasmon resonance (SPR) was used. First, to determine c-FMS binding, the purified proteins (4.22, 4.24, 5.6, M-CSF$_M$ and M-CSF$_{\alpha v\beta 3}$) were immobilized on the surface of the chip and different concentrations of c-FMS were tested for binding at different concentrations (0, 12.5, 25, 50, 100, and 200 nM) (FIG. 9A-J). The $K_D$ values for glycosylated and non-glycosylated M-CSF$_M$ were similar, namely, 42.6 nM and 31.6 nM, respectively. As expected, the binding affinities of the M-CSF$_{RGD}$ proteins to c-FMS were decreased because of the RGD loop substitution, resulting in $K_D$ values of 152 nM for 4.22, 219 nM for 4.24 and 96 nM for 5.6. As expected, M-CSF$_{\alpha v\beta 3}$ didn't show any binding to c-FMS. To determine the dissociation constants for $\alpha_v\beta_3$ integrin binding, the purified M-CSF$_{RGD}$, M-CSF$_M$ and M-CSF$_{\alpha v\beta 3}$ were immobilized on the surface of the chip and different concentrations of 43 integrin (200, 100, 50, 25, 21.5 and 0 nM) were allowed to flow over the chip surface. As expected, M-CSF$_M$ did not bind $\alpha_v\beta_3$ integrin. The binding affinities for the M-CSF$_{RGD}$ proteins were 199 nM for 4.22, 108 nM for 4.24 and 245 nM for 5.6 and the $K_D$ of M-CSF$_{\alpha v\beta 3}$ was measured at 231 nM. Thus, similar to the results obsered on the YSD, the three M-CSF$_{RGD}$ proteins demonstrated different affinities for $\alpha_v\beta_3$ integrin and c-FMS: 4.24 had a high $K_D$ for $\alpha_v\beta_3$ integrin and a lower $K_D$ for c-FMS, 5.6 was a high c-FMS binder and a lower $\alpha_v\beta_3$ integrin binder, and 4.22 had intermediate values for the two receptors. This heterogeneity in binding affinities enabled reaching the most sensitive balance and optimal effect on the osteoclast activity and differentiation.

Example 6

Figure 10A:
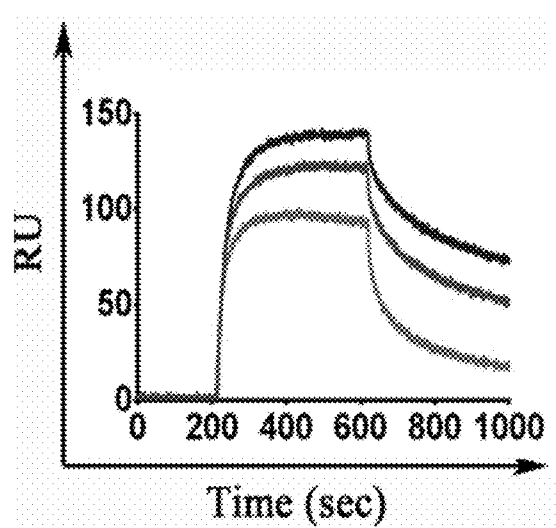
FIGS. 10A-10E show graphs demonstrating binding specificity of M-CSF$_{RGD}$ variants for RGD-binding integrins. αvβ3 (10A), αvβ5 (10B), α3β1 (10C), α4β7 (10D) and α5β1 (10E) integrins were immobilized on the surface of the chip, and the three M-CSF$_{RGD}$ variants 4.22, 4.24 and 5.6 were allowed to flow over the surface of the chip at a concentration of 1 μM.
Figure 10B:
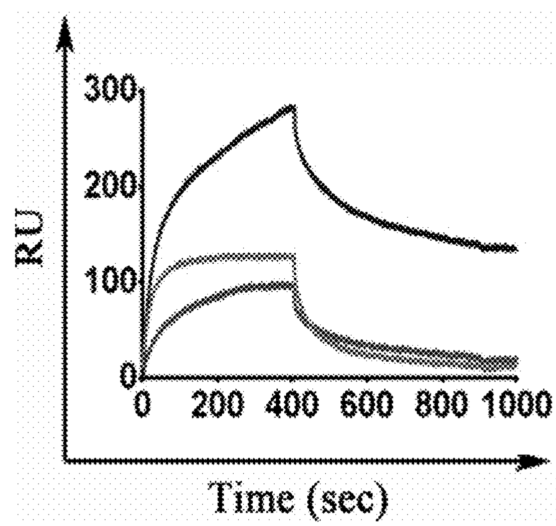
Figure 10C:
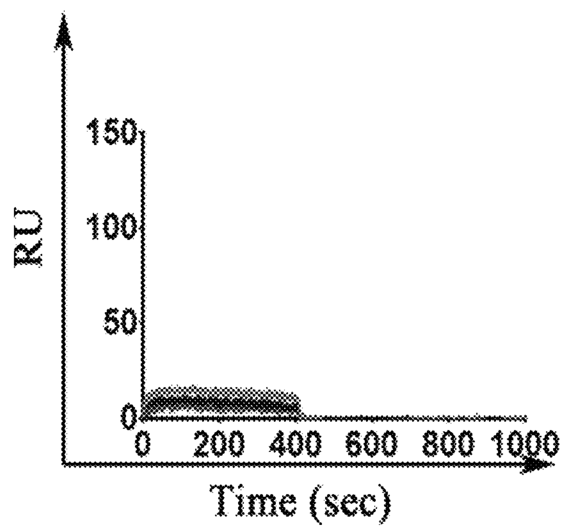
Figure 10D:
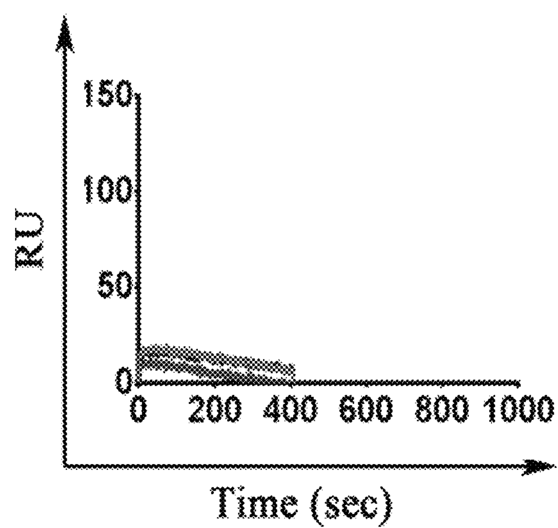
Figure 10E:
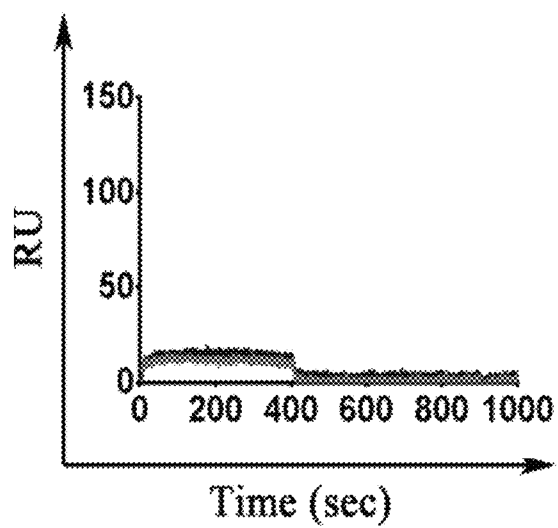

M-CSF$_{RGD}$ Variants Bind Soluble $\alpha v\beta_5$ Integrin and αvβ3 Integrin but No Other RGD-Binding Integrins To determine the specificity of the three M-CSF$_{RGD}$ variants for integrin $\alpha_v\beta_3$ vis-à-vis the other integrins produced in the human body, five different RGD-binding integrin ($\alpha_3\beta_1$, $\alpha_4\beta_7$, $\alpha_5\beta_1$, $\alpha_v\beta_5$ and $\alpha_v\beta_3$) were immobilized on the surface of the chip, and the M-CSF$_{RGD}$ variants were tested for integrin binding at a concentration of 1 μM. Integrin $\alpha_3\beta_1$, $\alpha_4\beta_7$ and $\alpha_5\beta_1$ did not bind the three M-CSF$_{RGD}$ proteins (FIGS. 10C-E). As previously described, integrin $\alpha_v\beta_3$ binds the soluble M-CSF$_{RGD}$ proteins with high affinity (FIG. 10A). Moreover, the integrin $\alpha_v\beta_5$ binds the M-CSF$_{RGD}$ proteins as well (FIG. 10B). Although $\alpha_v\beta_5$ integrin is not expressed solemnly on osteoclasts, it is regulated by c-FMS signaling as $\alpha_v\beta_3$ integrin as well. During osteoclast differentiation and c-FMS signaling, the expression levels of $\alpha_v\beta_3$ integrin increases and $\alpha_v\beta_5$ integrin reduces. Corresponding with the SPR $\alpha_v\beta_3$ integrin binding experiment, the binding affinity of M-CSF$_{RGD}$ proteins to $\alpha_v\beta_3$ integrin is in the same order of $\alpha_v\beta_5$ integrin binding, 4.24 is the best $\alpha_v\beta_5$ integrin followed by 4.22 and 5.6.

Example 7

Direct Cell Binding of M-CSF$_M$ and M-CSF$_{RGD}$ Variants

Figure 11A:
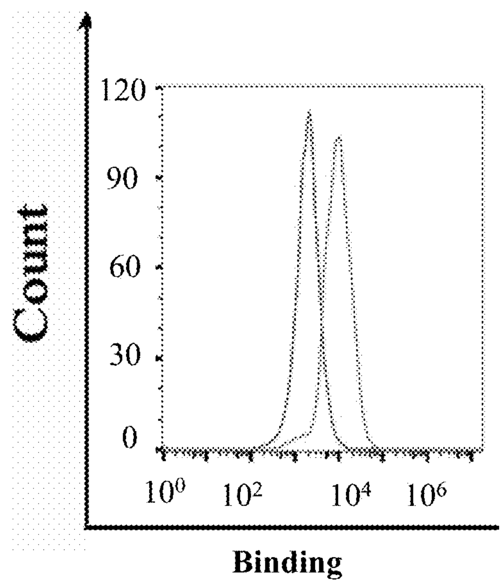
FIGS. 11A-11F show graphs demonstrating results of direct cell binding assay with flow cytometry. Purified M-CSF$_{RGD}$ variants and M-CSF$_{M}$ proteins were tested for binding to murine primary cells (FIGS. 11A, 11B and 11C) and MDA-231 breast cancer cell line (FIGS. 11C, 11D and 11F). The black histograms represent the negative control and the gray histograms represent protein binding or receptor expression. The cells express c-FMS (FIGS. 11A, 11C) and $\alpha_v\beta_3$ integrin (FIGS. 11B, 11D). The mouse primary cells (FIG. 11E) and MDA-231 cells (FIG. 11F) showed binding in a dose dependent manner to 1 μM, 2.5 μM and 7.5 μM, each, of M-CSF$_{M}$, 4.22 and 5.6.
Figure 11B:
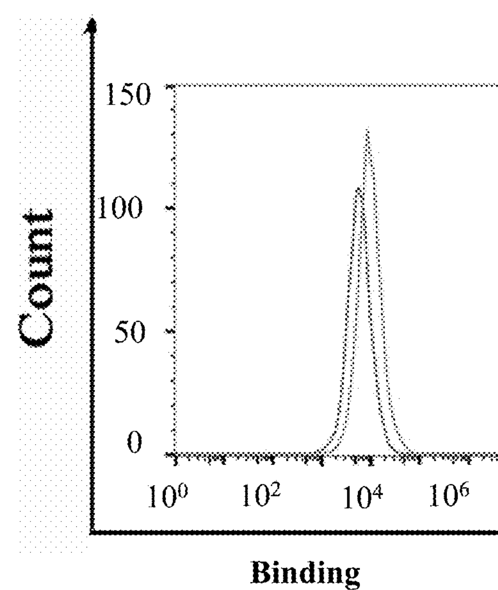
Figure 11C:
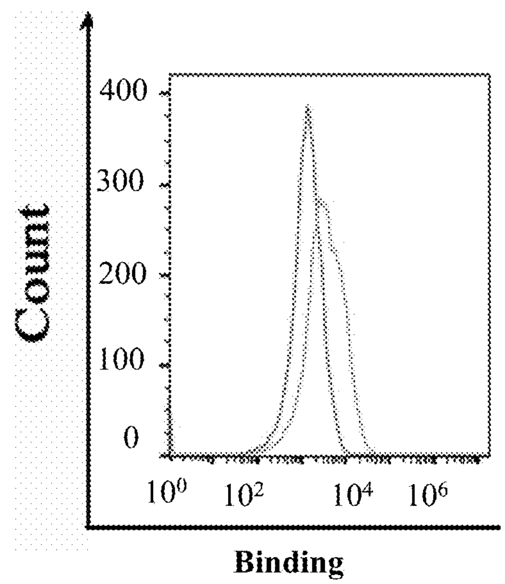
Figure 11D:
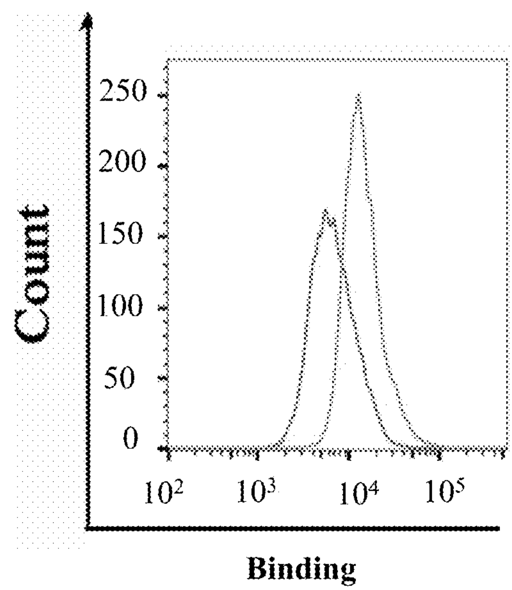
Figure 11E:
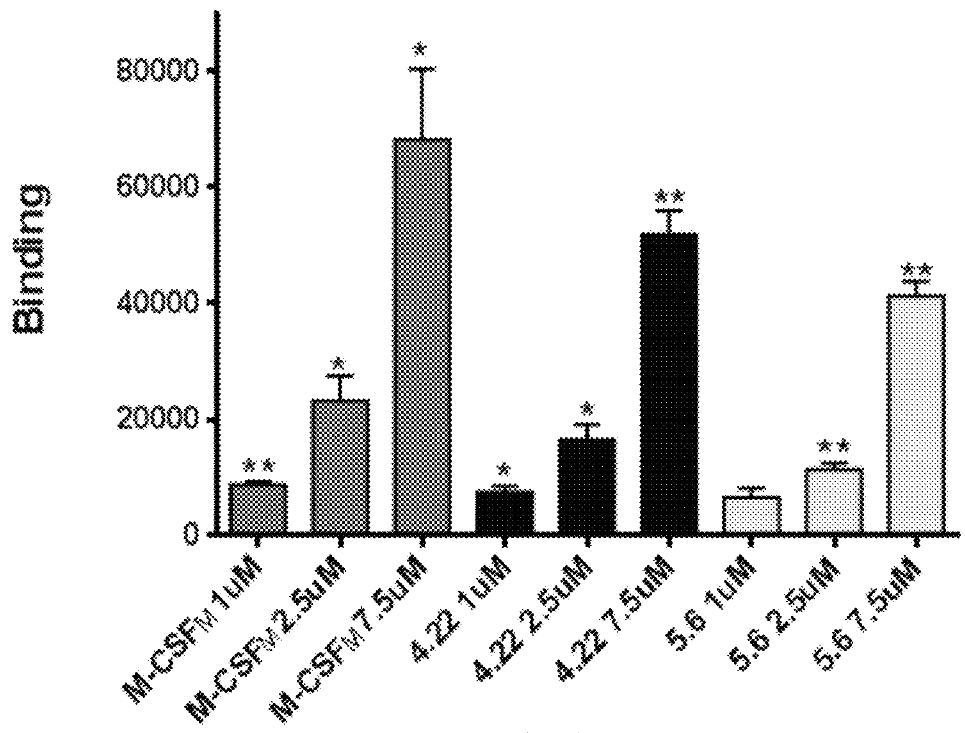
Figure 11F:
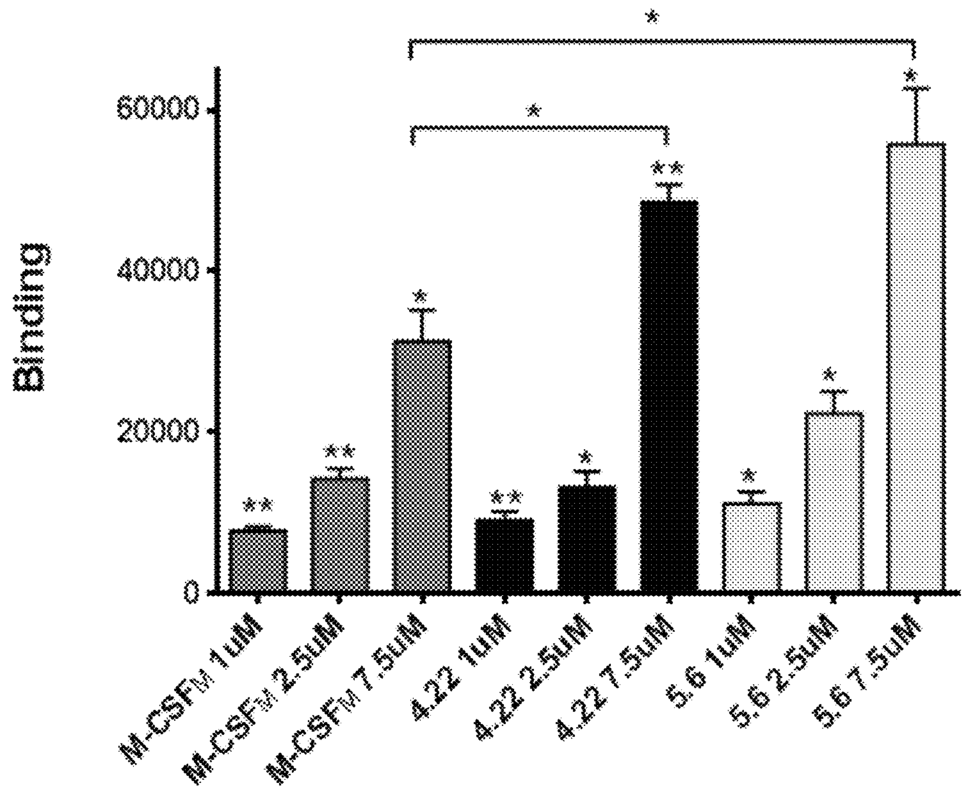
Figure 12A:
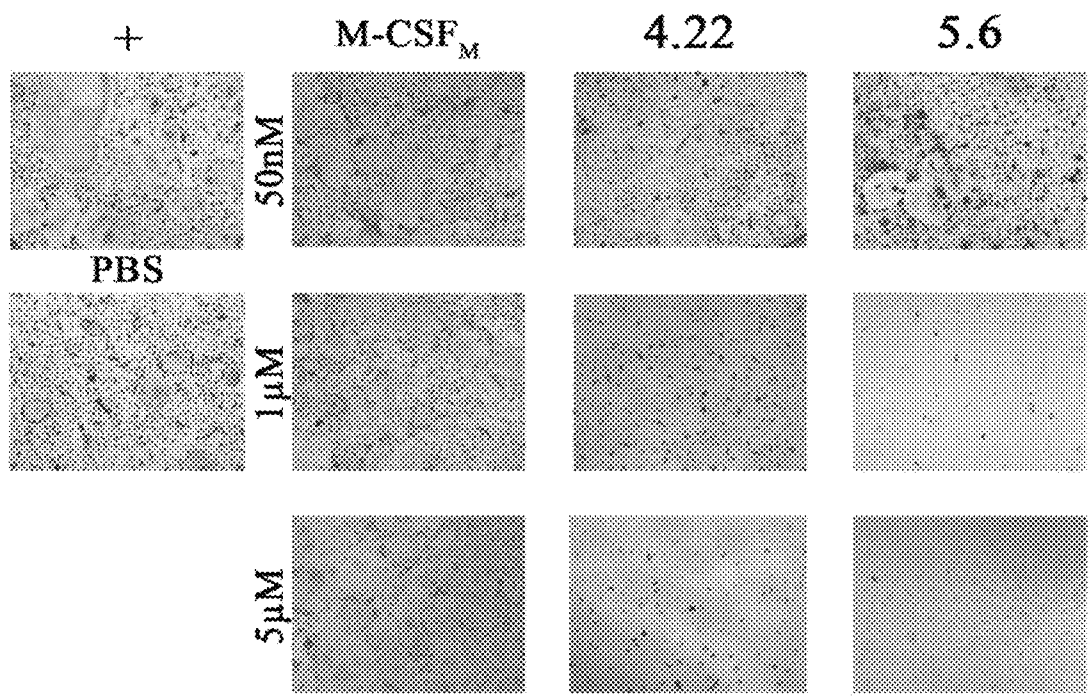
FIGS. 12A-12D show photographs (FIG. 12) and bar graphs (FIG. 12B-D) demonstrating the effects of different M-CSF$_{RGD}$ variants and M-CSF$_{M}$ on osteoclast differentiation. Primary mouse bone marrow monocytes were cultured for 96 h in α-MEM growth medium containing recombinant mouse M-CSF (20 ng/ml), RANKL (20 ng/ml) and different concentrations of inhibitors. Positive control contained α-MEM growth medium, recombinant M-CSF and RANKL but not inhibitors. Negative control contains α-MEM growth medium and recombinant M-CSF and PBS control has 10% PBS with recombinant M-CSF and RANKL.
Figure 12B:
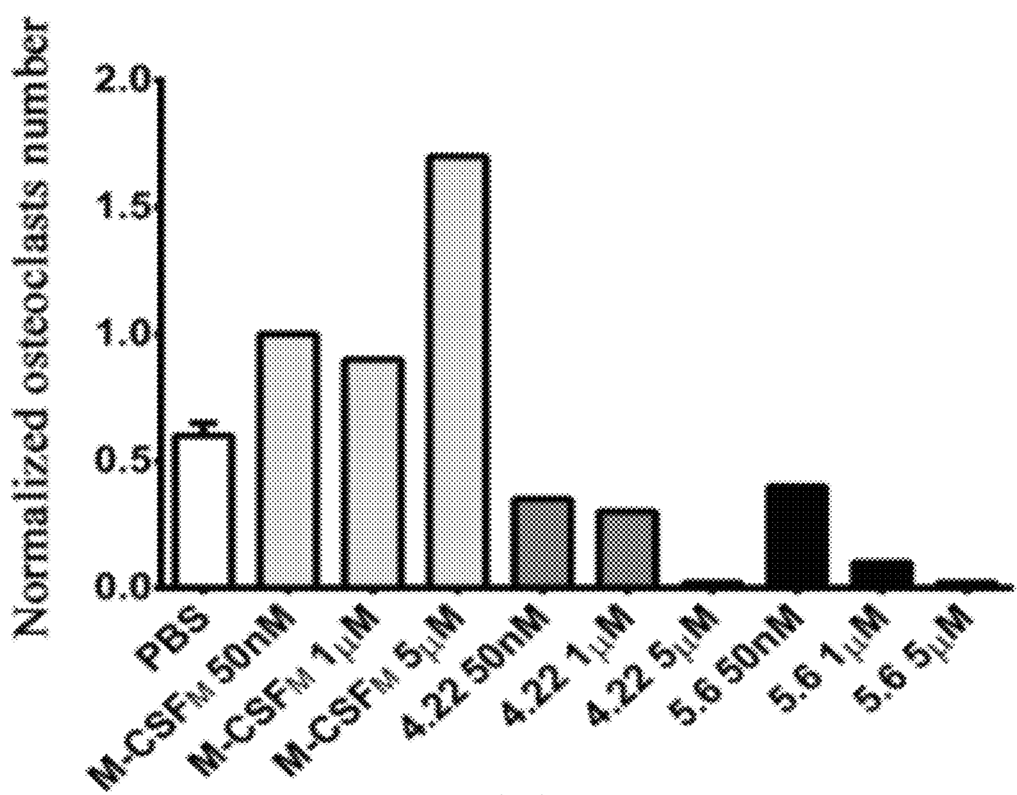
Figure 12C:
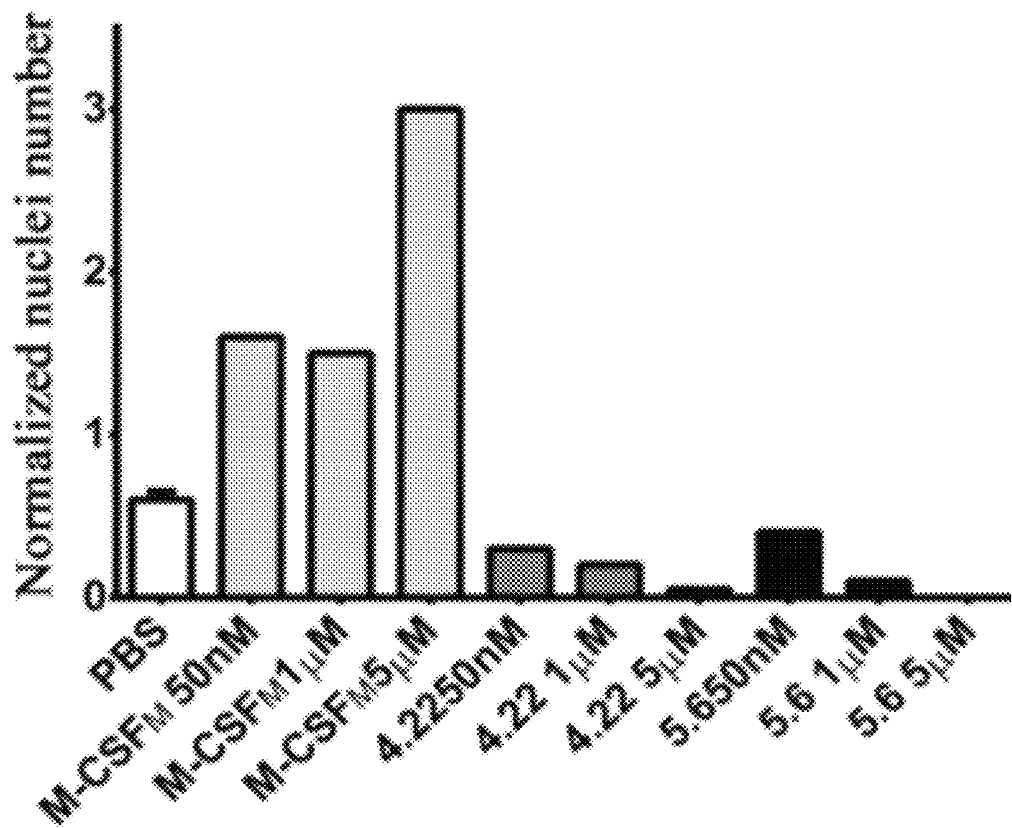
Figure 12D:
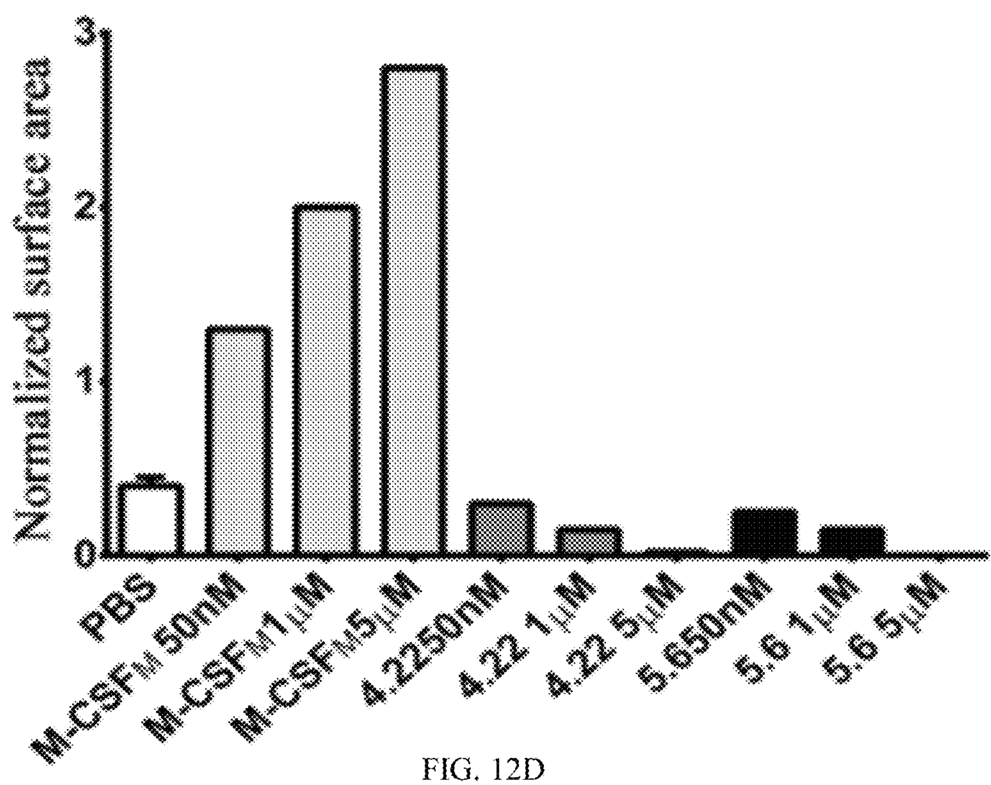

Assays for direct cell binding were conducted on breast cancer cell line MDA-MB-231 and murine primary cells with flow cytometer. MDA-MB-231 was used because the cells express $\alpha_v\beta_3$ integrin and c-FMS on the cell membrane, a protein expression pattern that imitates the osteoclast state just before reaching full differentiation and maturation. This cell line showed binding to 1 μM, 2.5 μM and 7.5 μM of M-CSF$_M$ and to the 4.22 and 5.6 M-CSF$_{RGD}$ variants (FIG. 11F). M-CSF$_{RGD}$ variant 5.6 showed the best binding ability and M-CSF$_M$ is the weakest binder. Murine primary cells that were obtained from bone marrow were tested for binding without any induction of differentiation (t=0). Such cells express high levels of c-FMS and low levels of $\alpha_v\beta_3$ integrin (FIGS. 11A and 11B), a state that imitates an early osteoclast differentiation stage. For these cells, M-CSF$_M$ showed stronger cell binding than 5.6 and 4.22 (FIG. 6E), probably due to its higher affinity to c-FMS, which is the dominant target on the cell membrane.

Example 8

M-CSF$_M$ and M-CSF$_{RGD}$ Variants Inhibit In Vitro Osteoclast Differentiation Murine bone marrow monocytes were purified from the bone marrow of eight- to twelve-week-old mice and were seeded for osteoclast differentiation in the presence of recombinant M-CSF and RANKL for 72-96 h. To assess the ability of the M-CSF$_{RGD}$ variants, M-CSF$_M$ and M-CSF$_{\alpha v\beta 3}$ to inhibit osteoclast differentiation three different concentrations of the inhibitors were added to the differentiation medium: 50 nM, 1 μM and 5 μM. At the end of the differentiation period, osteoclasts were fixed and stained for Tartrate resistant acid phosphatase activity (TRAP). Osteoclast differentiation and spreading were evaluated in terms of three parameters: number of osteoclasts, number of nuclei in osteoclasts and osteoclast surface area. Surprisingly, all the tested M-CSF$_{RGD}$ variants inhibited osteoclast differentiation in a dose dependent manner, showing significant inhibition at concentration as low as 50 nM and completely abolishing the appearance of multinucleated cells at concentrations higher than 1 μM. Osteoclast surface area, a good indicator of $\alpha_v\beta_3$ integrin activity, was also markedly decreased compared to the positive control, indicating $\alpha_v\beta_3$ integrin inhibition (FIGS. 12A-D). M-CSF$_M$ markedly enhanced osteoclast differentiation, this may indicate that some M-CSF$_M$ dimerization took place at high concentrations. These results show that all the M-CSF$_{RGD}$ variants inhibited osteoclast differentiation and spreading even at low concentrations and they therefore hold good promise for further development, including testing in in vivo experiments.

Example 9

Osteoclast Formation Inhibition Using a M-CSF Double Mutant (M-CSFM, M27R)

The C31 S mutation prevents M-CSF from forming the disulfide bond between two M-CSF monomers, while still allowing it to dimerize non-covalently. When M-CSF dimerizes, each methionine in position 27 binds to a hydrophobic pocket in the opposite monomer. The addition of M27R mutation inhibits the non-covalent dimerization as well, since arginine is too large and positive to fit in this pocket.

When M-CSF binds to c-FMS in its monomeric form, it prevents the two c-FMS monomers from dimerizing, thus inhibiting the downstream signaling pathways followed by c-FMS phosphorylation, including proliferation and differentiation of mononuclear macrophages to osteoclasts.

Figure 13:
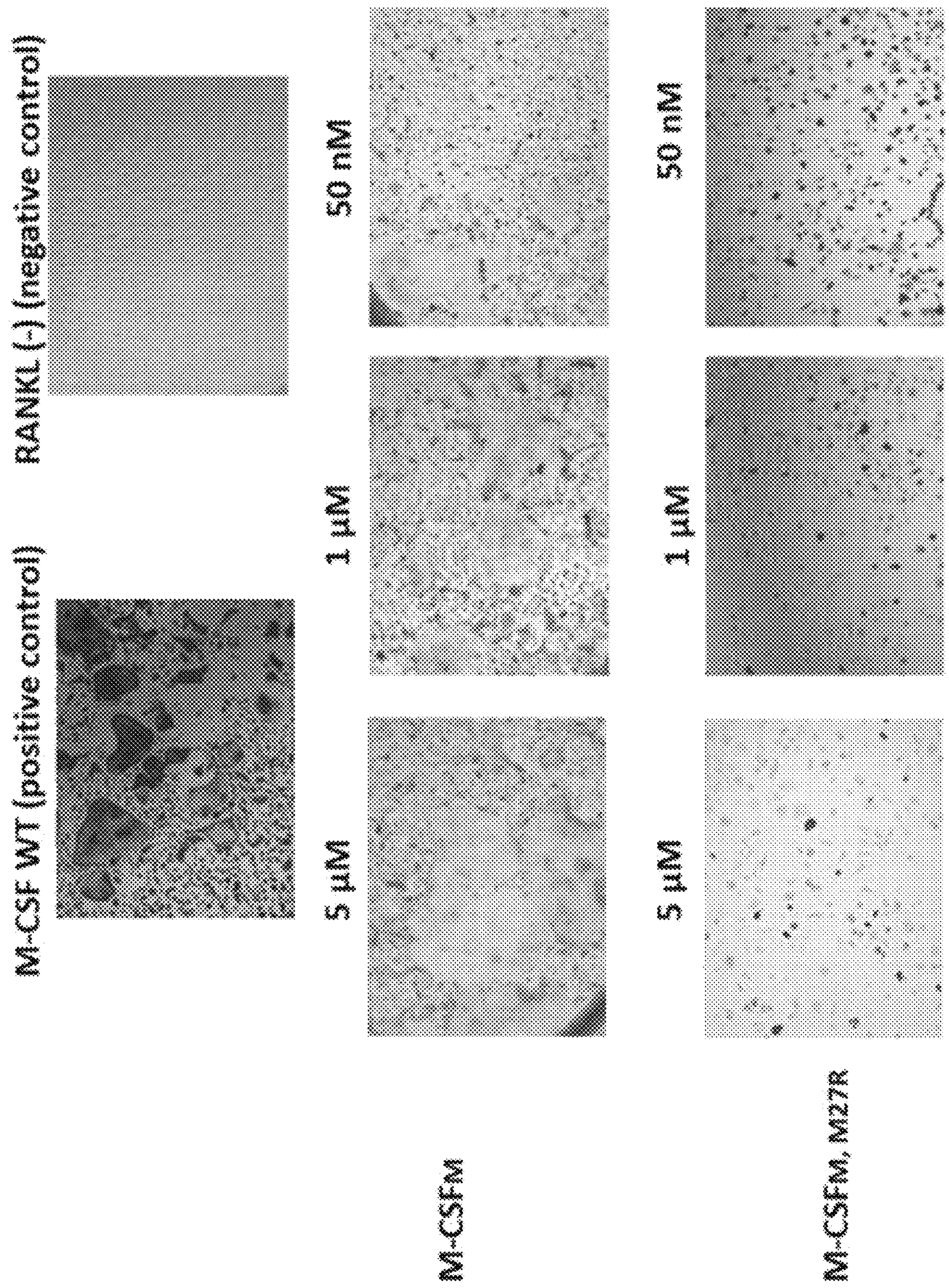
FIG. 13 shows the effect of M-CSFM (containing only C31S mutation) and M-CSFM, M27R (containing both C31 S and M27R) on the differentiation of primary murine cells to osteoclasts.

FIG. 13 shows the effect of M-CSFM (containing only C31 S mutation) and M-CSFM,M27R (containing both C31 S and M27R) on the differentiation of primary murine cells to osteoclasts. The positive control contains a differentiation medium with both M-CSF WT and RANKL. The negative control contains only RANKL, which keeps the cells alive though not differentiated. Varying concentrations of M-CSFM and M-CSFM,M27R were added to the cells, that were grown for five days. Then the cells were fixated and stained using TRAP staining for differentiated osteoclasts.

M-CSFM acts as an inducer for osteoclast differentiation, generating more osteoclasts than the positive control, probably due to its ability to dimerize, while M-CSFM, M27R inhibits osteoclast formation in a dose dependent manner, leading to small and poorly differentiated cells.

Example 10

Crystallization of M-CSF$_{C31S}$ and Computational Analysis of Residues Contributing to Dimer Formation The M-CSF$_{C31S,\ M27R}$, variant, albeit monospecific (targeting only c-FMS and not integrins), is highly potent both in vitro and in cell based assays against osteoclasts. This mutation makes the protein a monomer (vs the M-CSF-wt which is a dimer) and thus a very potent antagonist in-vitro.

The C31 S mutation prevents M-CSF from forming the disulfide bond between two M-CSF monomers, while still allowing it to dimerize non-covalently. When M-CSF dimerizes, each methionine in position 27 binds to a hydrophobic pocket in the opposite monomer. The addition of M27R mutation inhibits the non-covalent dimerization as well since arginine is too large and positive to fit in this pocket. When M-CSF binds to c-FMS in its monomeric form, it prevents the two c-FMS monomers from dimerizing, thus inhibiting the downstream signaling pathways followed by c-FMS phosphorylation, including proliferation and differentiation of mononuclear macrophages to osteoclasts.

Figure 14A:
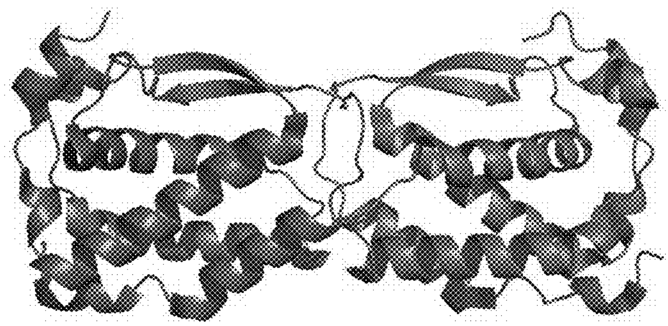
FIGS. 14A-14D show the structure of the M-CSF$_{C31S}$ mutant, compared to the M-CSF wild-type structure.
Figure 14B:
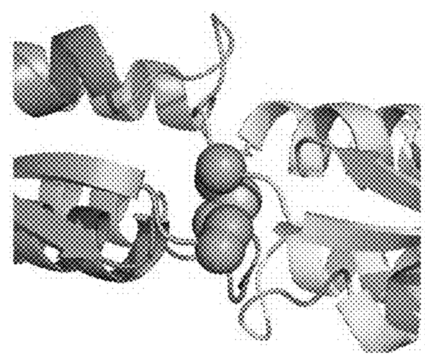

To generate a monomeric M-CSF variant, the M-CSF$_{C31S}$ variant, which cannot form an intramolecular disulfide bond at position 31, was first crystallized. Purified M-CSF$_{C31S}$ was subjected to several crystallization trials using the sitting drop vapor diffusion method, and crystals formed after nine days. The data set used for structure determination was collected at BM14 beamline at the European Synchrotron Radiation Facility (ESRF; Grenoble, France). The crystal structure was solved to a maximum resolution of 2.0 Å (FIG. 14A, PDB ID: 5LXF) by molecular replacement, using as a search model PDB ID: 3UF2.

Figure 14C:
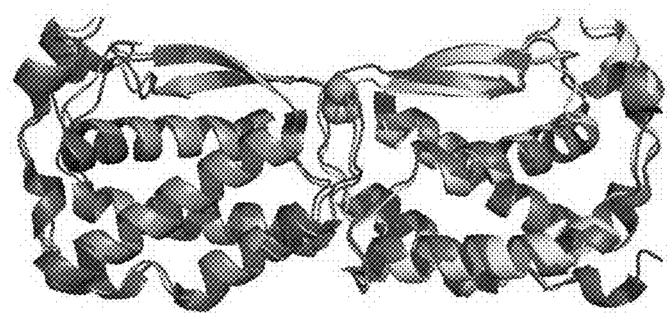
Figure 14D:
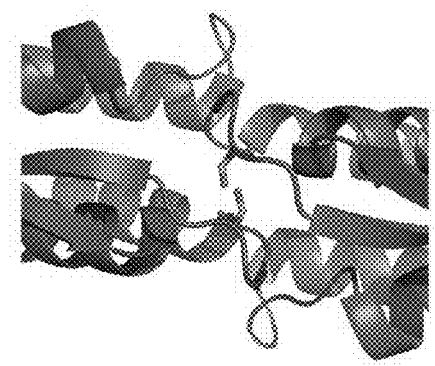

Surprisingly, M-CSF$_{C31S}$ showed only minor tertiary structural differences relative to wild-type M-CSF (M-CSF$_{WT}$) and essentially no differences in the quaternary dimeric structure (FIGS. 14A-D). In the same location of the C31-C31 disulfide bond in the M-CSF wildtype (FIG. 14B) a S31-S31 hydrogen bond was observed between the serine side chains (FIG. 14D). The M-CSF$_{WT}$ and M-CSF$_{C31S}$ mutant structures superimposed with an RMSD of ~1 Å over the full length of the structures, and were very similar across the entire chain (FIG. 14C). The dimer interface of the mutant was highly similar to that of the wild type, suggesting that the M-CSF$_{C31S}$ mutation is not sufficient to prevent the formation of an M-CSF dimer and that further mutagenesis is required to abolish dimerization.

Energy-based approach was applied to identify critical positions as candidates for mutagenesis to perturb the dimer interface. Using the M-CSF$_{C31S}$ dimeric structure as input, energy calculations were applied to identify the residues that contribute significantly to the M-CSF$_{C31S}$-M-CSF$_{C31S}$ dimer interface. Finite difference Poisson-Boltzmann (FDPB) method was used to calculate the net electrostatic and polar contributions ($\Delta\Delta G_{elec}$) of each M-CSF$_{C31S}$ residue that is within 15 Å of the dimer interface. Non-polar energetic contributions ($\Delta\Delta G_{np}$) were calculated as a surface-area proportional term by multiplying the per-residue surface area buried upon complex formation by a surface tension constant of 0.05 kcal/mol/Λ. Energetically significant residues were defined as those contributing $\Delta\Delta G_{elec}$ or $\Delta\Delta G_{np} \geq 1$ kcal/mol to the interactions.

Figure 15A:
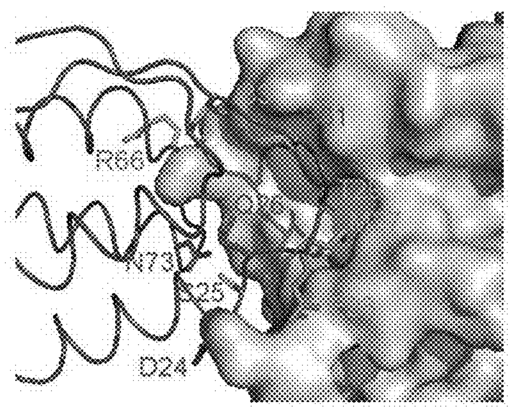
FIGS. 15A-15C show the significant contribution of the M-CSF$_{C31S}$ residues to the interaction across the M-CSF$_{C31S}$ dimer interface.
Figure 15B:
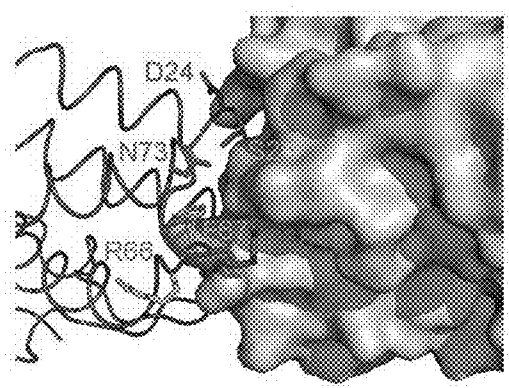

This approach identified twelve interfacial M-CSF$_{C31S}$ residues that made significant contributions to the intermolecular interactions between the two M-CSF molecules (Table 1, FIGS. 15A,B). These residues reside in two segments of M-CSF. The main segment includes most of the residues between D24-I33 (FIG. 15A). The second shorter segment includes a hydrophobic residue (F67) and three charged/polar residues—R66, R68, and N73 (FIG. 15B).

TABLE 1

Per-residue energy contributions to interaction across the M-CSF dimer interface

| M-CSF residue | Energy contribution to M-CSF dimer formation | Residue adjacent to c-FMS |
|---|---|---|
| D24 | sc + mc + np | |
| S25 | Np | |
| Q26 | sc + np (symmetry contact with corresponding Q26 across the dimer interface) | |
| M27 | np (~150 Å$^2$ buried in adjacent monomer, no intramolecular interactions) | |
| E28 | np | |
| T29 | np | |
| S31 | np + sc | |
| I33 | np | |
| R66 | mc + np | + |
| F67 | np | + |
| R68 | sc + mc + np | + |
| N73 | mc + np | + |

Calculations as described in Methods. np = non-polar, sc = side-chain electrostatic contribution, mc = main-chain electrostatic contribution.

Figure 15C:
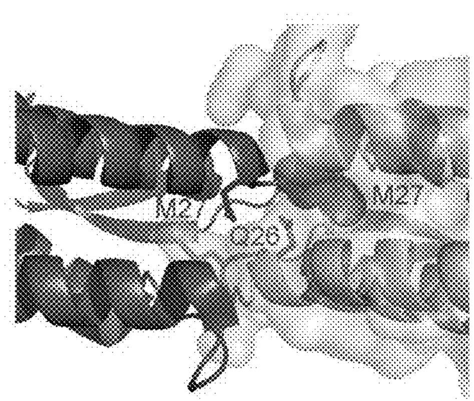

As opposed to the other identified residues, residue M27 fulfilled the following four conditions: 1) Especially strong contributions to dimer formation, 2) Lack of involvement in receptor binding, 3) Minimal intramolecular interactions that could affect monomer stability, and 4) A predicted introduction of strong steric interference between the two M-CSF monomers upon mutation. The M27 residue extends deep into the opposing M-CSF$_{C31S}$ monomer (FIG. 15C). As a result, about 150 Å$^2$ of surface area is buried within the opposing monomer due to each M27, more than any other M-CSF$_{C31S}$ residue. This residue was mutated to arginine, with the aim to introduce both a steric hindrance and a positive charge into a hydrophobic environment.

Example 11

Figure 16A:
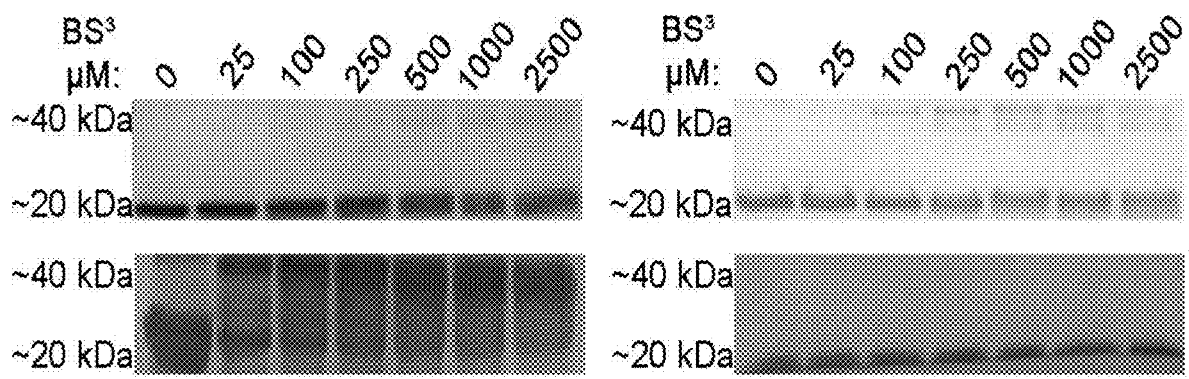
FIGS. 16A-16C show biophysical assays to evaluate the oligomeric state of the M-CSF variants.

Analysis of the Dimerization of M-CSF$_{WT}$, M-CSF$_{C31S}$, and M-CSF$_{C31S,M27R}$ To validate the structural and computational analysis and to verify that M-CSF$_{C31S,M27R}$ is indeed a monomer, several biophysical assays were conducted. First, purified murine and human M-CSF$_{WT}$, M-CSF$_{C31S}$ and M-CSF$_{C31S,M27R}$ were crosslinked via lysine residues using different amounts of BS$^3$ reagent [bis(sulfosuccinimidyl)suberate], and the proteins sizes were evaluated using SDS-PAGE (FIG. 16A). Murine M-CSF$_{WT}$ served as positive control, since it has a lysine in the dimerization site ($K_{68}$), which facilitates the intermolecular cross-linking of the two monomers in the dimer. Indeed, murine M-CSF$_{WT}$ was observed almost entirely in a band with a molecular weight that fits the dimer size (~40 kDa) upon addition of the crosslinker. In contrast, human M-CSF$_{WT}$, which has an arginine in the same position, produced only a faint band in a size that corresponds to a dimer, even at high concentrations of BS$^3$. M-CSF$_{C31S}$ gave a mixture of monomer and dimer bands (~20 and ~40 kDa). The dimer band became more prominent at higher BS$^3$ concentrations. It is likely that the non-covalent dimerization allows other lysines in M-CSF$_{C31S}$ to come into close proximity and crosslink. Importantly, M-CSF$_{C31S,M27R}$ did not produce any band corresponding to a dimer, even at high BS$^3$ concentrations. These results are in agreement with the structure-based computational redesign.

Figure 16B:
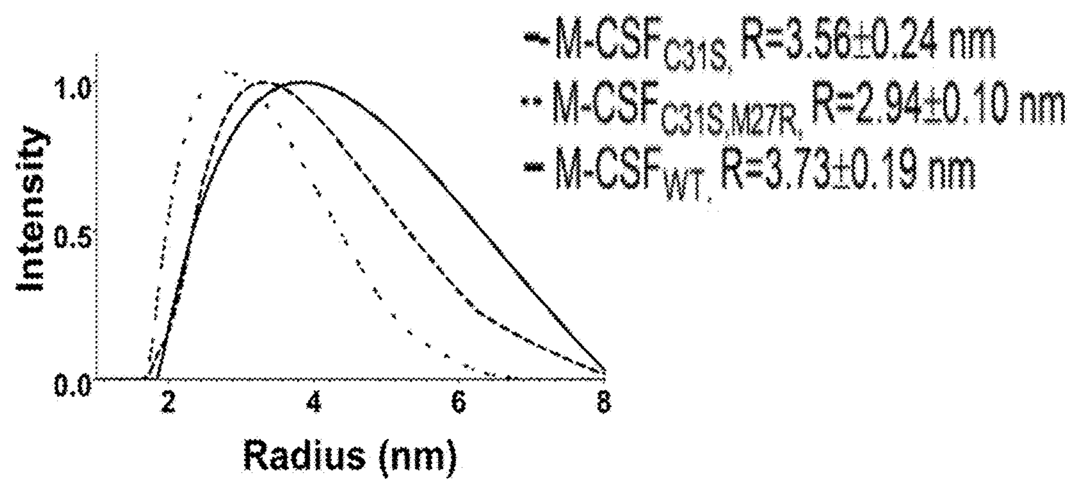
Figure 16C:
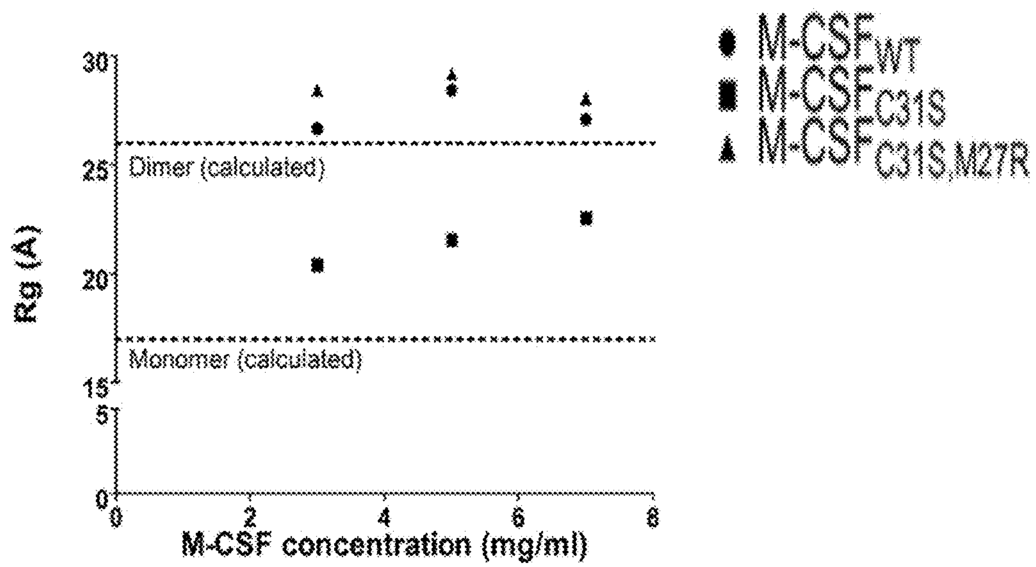

Next, the size of the M-CSF variants was evaluated in solution. M-CSF$_{WT}$, M-CSF$_{C31S}$ and M-CSF$_{C31S,M27R}$ at concentrations of 0.5 mg/ml were subjected to dynamic light scattering (DLS) analysis at an angle of 90°. The peaks for the most abundant species in each sample were compared (FIG. 16B), and an estimated hydrodynamic radius was calculated from each peak. The hydrodynamic radii were found to be 3.73±0.19, 3.56±0.24 and 2.94±0.10 nm for M-CSF$_{WT}$, M-CSF$_{C31S}$, and M-CSF$_{C31S,M27R}$, respectively. Since the proteins are not completely globular, the calculated radii do not represent the actual size of the molecules, but they do enable comparing the sizes of the proteins. M-CSF$_{C31S,M27R}$ was indeed found to be significantly smaller than the other two variants, supporting the hypothesis that the former is a monomer. To confirm that the oligomeric state of M-CSF$_{C31S,M27R}$ is not concentration dependent, all M-CSF variants were subjected to SAXS measurements at concentrations of 3, 5 and 7 mg/ml. The radii of gyration ($R_g$) determined from SAXS data are presented in FIG. 16C. Of note is that the $R_g$ values remained within a similar range for M-CSF$_{WT}$ and M-CSF$_{C31S}$. There was a slight increase in the $R_g$ value of M-CSF$_{C31S,M27R}$ at higher concentrations, presumably due to an increase in interparticle interactions. Still, the $R_g$ value at the lowest M-CSF$_{C31S,M27R}$ concentration was significantly lower than the corresponding values of M-CSF$_{WT}$ and M-CSF$_{C31S}$, and close to the theoretical $R_g$ for the M-CSF monomer (FIG. 16B, dashed line, $R_g$=17 Å). To illustrate the oligomeric states of these three proteins in solution, low-resolution structures were reconstructed from the SAXS data. Ab initio models were reconstructed from SAXS data using the computer program GASBOR and were averaged by the computer program DAMAVER. The crystal structure of the M-CSF dimer and the structure of the monomer were aligned with the obtained SAXS models (yellow, M-CSF-.sub.WT; green, M-CSF.sub.C31S; cyan, M-CSF.sub.C31S, M27R) using PyMOL (http://www.pymol.org). The $R_g$ values extracted from the SAXS profiles and the corresponding SAXS reconstructed structures support the premise that M-CSF$_{WT}$ and M-CSF$_{C31S}$ exist as dimers in solution, whereas M-CSF$_{C31S,M27R}$ is a monomer.

Example 12

M-CSF$_{C31S,M27R}$ Retains Binding to the c-FMS Receptor In Vitro

Figure 17A:
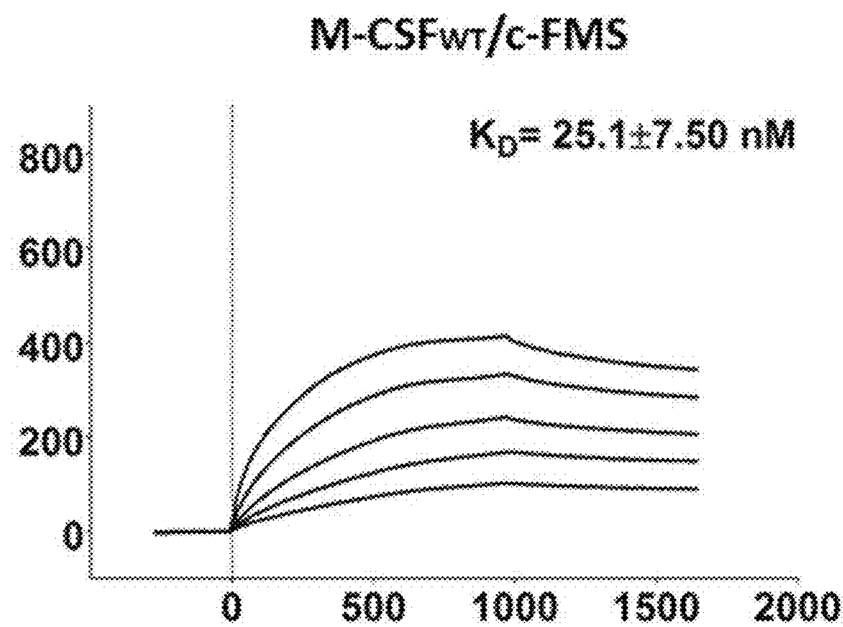
FIGS. 17A-17B depict the affinity of M-$CSF_{WT}$ and M-$CSF_{C31S,M27R}$ to the c-FMS receptor, as detected by SPR. Sensogram of M-$CSF_{WT}$ binding to c-FMS in concentrations up to 70 nM (17A) and M-$CSF_{C31S,M27R}$ binding to c-FMS in concentrations up to 20 nM. N=3 (17B). Values are means±SD.
Figure 17B:
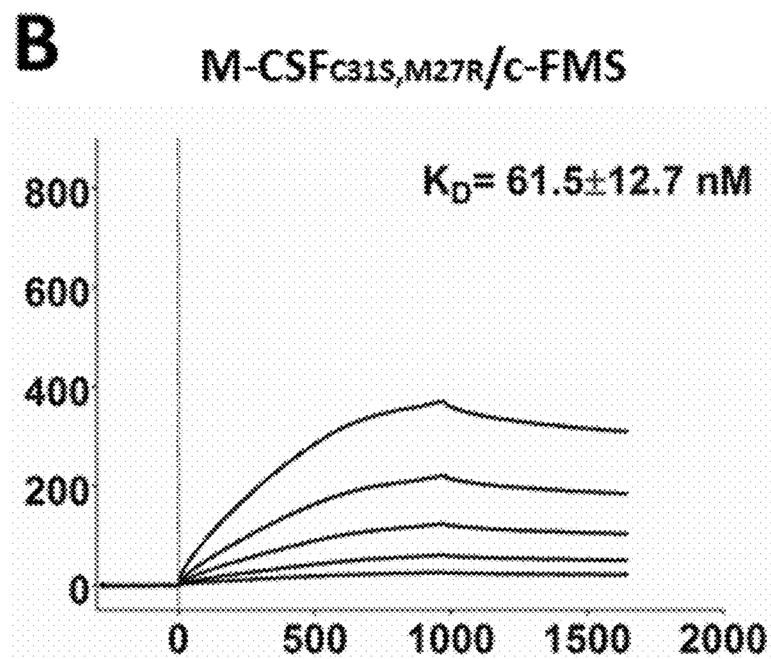

In order to test whether M-CSF$_{C31S,M27R}$ could still bind the extracellular domains of c-FMS receptor (residues Met1-Glu512) the $K_D$ of M-CSF$_{WT}$ and M-CSF$_{C31S,M27R}$ to the receptor was measured by using SPR spectroscopy. The different M-CSF proteins were attached to the chip, and binding to different concentrations of c-FMS in solution was measured (FIG. 17A-B). The $K_D$ binding constants between c-FMS and M-CSF$_{WT}$, M-CSF$_{C31S}$ and M-CSF$_{C31S,M27R}$ were: 25.1±7.50, 3 1.6±1.11 and 61.5±12.7 nM, respectively. The observed decrease in c-FMS affinity for M-CSF$_{C31S,M27R}$ is indicative of the biological activity.

Example 13

M-CSF$_{C31S,M27R}$ Inhibits c-FMS Phosphorylation

Figure 18A:
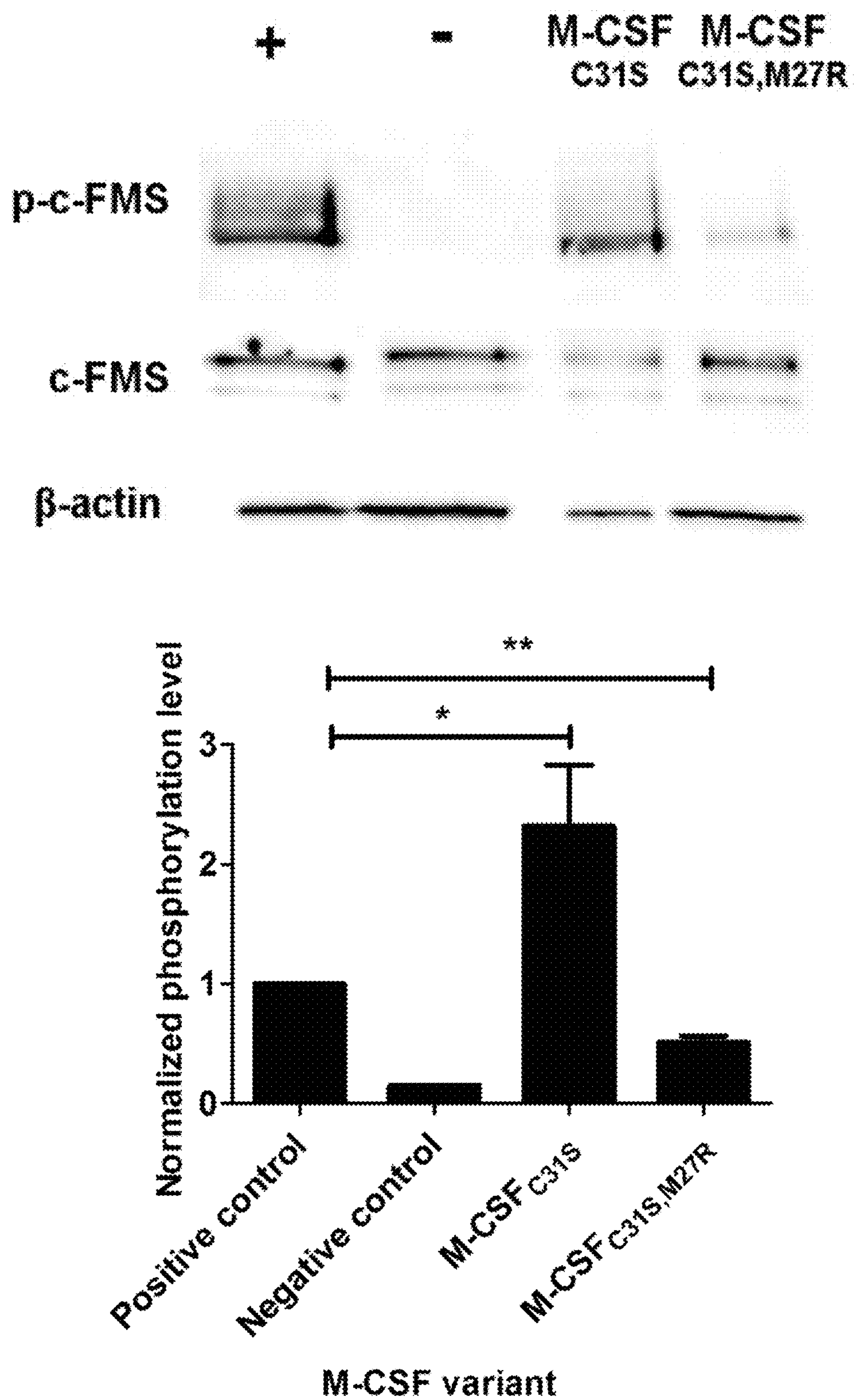
FIGS. 18A-18B show the evaluation of c-FMS phosphorylation in response to M-CSF variants. (18A) Phosphorylation of murine c-FMS on BMMs after incubation with 0.5 nM murine M-CSF (positive control, +), no M-CSF (negative control, −) or 0.5 nM murine M-CSF+1 μM of M-$CSF_{C31S}$ or M-$CSF_{C31S,M27R}$. (18B) Phosphorylation of human c-FMS on $CD14^+$ cells after incubation with 0.5 nM human M-CSF (positive control, +), no M-CSF (negative control, −) or 0.5 nM murine M-CSF+100 nM of M-$CSF_{C31S}$ or M-$CSF_{C31S,M27R}$. All signals were normalized to those of β-actin, c-FMS expression and the positive control in each experiment. Statistical analysis was calculated using a t-test, each sample was compared to the positive control. N=3. Values are means±SEM. *, $p<0.05$; * *, $p<0.01$; * * *, $p<0.005$.

To determine whether M-CSF$_{C31S,M27R}$ binds and also antagonizes c-FMS, the phosphorylation of the receptor following incubation with different M-CSF variants was evaluated. First, murine bone marrow derived monocytes (BMMs) were used, as murine c-FMS were previously shown to bind human M-CSF due to the high sequence identity between the two ligands. BMMs were grown for 48 h in differentiation medium containing murine M-CSF$_{WT}$ (20 ng/ml) and RANKL (20 ng/ml). Then, the cells were starved and exposed to both murine M-CSF$_{WT}$ (0.5 nM) and either M-CSF$_{C31S}$ or M-CSF$_{C31S,M27R}$ (1 μM). The cells were lysed, and the expression and phosphorylation levels of c-FMS were evaluated using western blot. C-FMS phosphorylation level was quantified and normalized. Cells that were exposed to M-CSF$_{C31S}$ exhibited increased levels of phosphorylation compared to those that were exposed to M-CSF$_{WT}$, which served as the control. This finding indicates that the M-CSF$_{C31S}$ variant remains an agonist to the receptor (FIG. 18A). In contrast, cells that were incubated with M-CSF$_{C31S,M27R}$ were found to have lower levels of phosphorylated c-FMS, i.e., M-CSF$_{C31S,M27R}$ acts as an antagonist to the receptor (FIG. 18A).

Figure 18B:
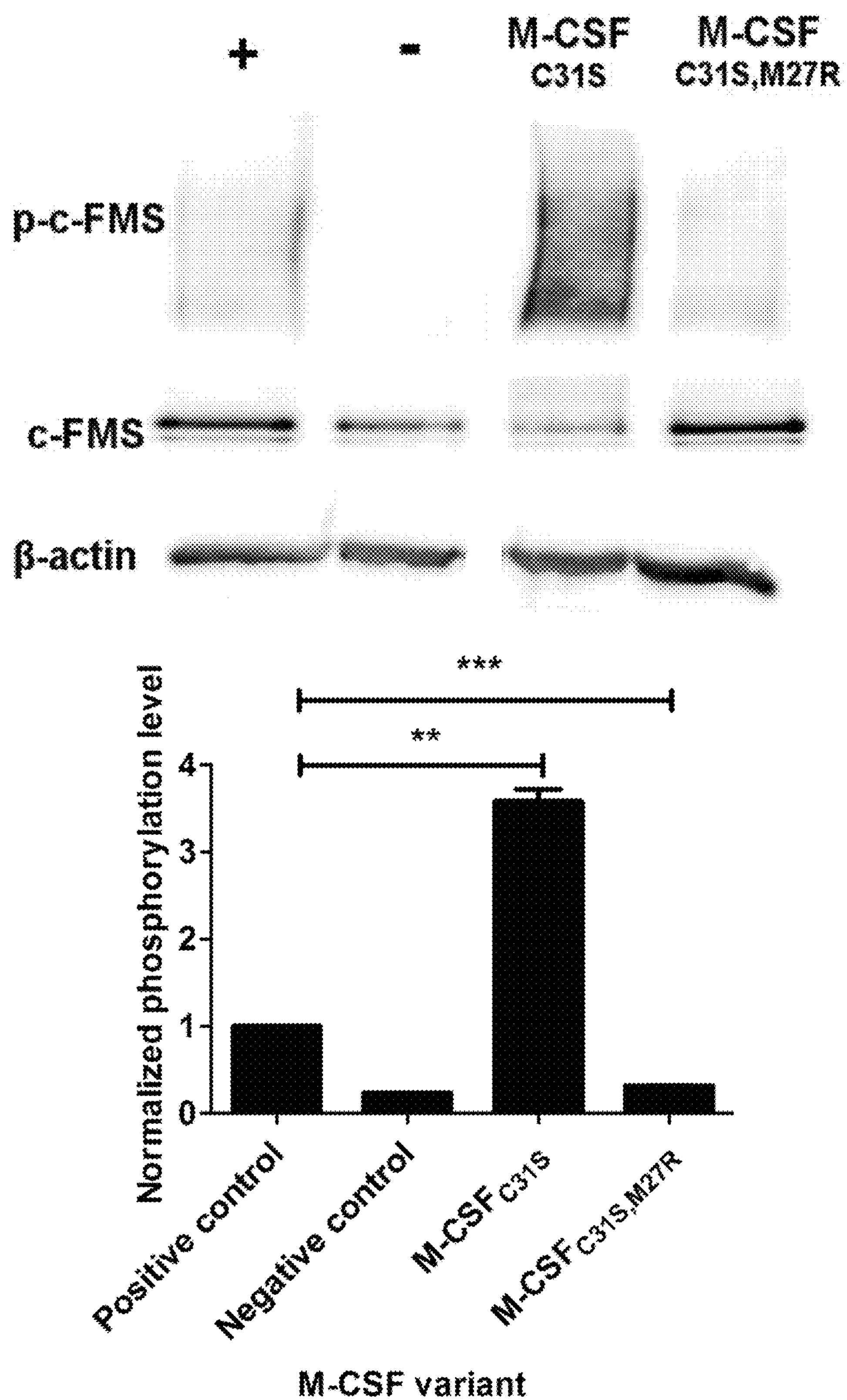

Another experiment was conducted with human peripheral blood CD 14$^{+}$ monocytes to determine whether M-CSF$_{C31S,M27R}$ has the same effect on human c-FMS. CD 14$^{+}$ cells were grown in differentiation medium containing human M-CSF$_{WT}$ and murine RANKL for 72 h, and after starvation were exposed to human M-CSF$_{WT}$ (0.5 nM) in combination with either M-CSF$_{C31S,M27R}$ or M-CSF$_{C31S}$ (100 nM). Again, the presence of M-CSF$_{C31S,M27R}$ resulted in decreased phosphorylation of c-FMS (FIG. 18B), while M-CSF$_{C31S}$ acted as an agonist, inducing phosphorylation (FIG. 18B). The effects of the different M-CSF variants on the phosphorylation of c-FMS may result from their dimerization tendency. While M-CSF$_{C31S}$ is a dimer and allows c-FMS dimerization and phosphorylation, the monomeric M-CSF$_{C31S,M27R}$ would probably not promote c-FMS dimerization, and therefore its subsequent phosphorylation is reduced.

Example 14

M-CSF$_{C31S,M27R}$ impairs differentiation of monocytes to osteoclasts

Figure 19A:
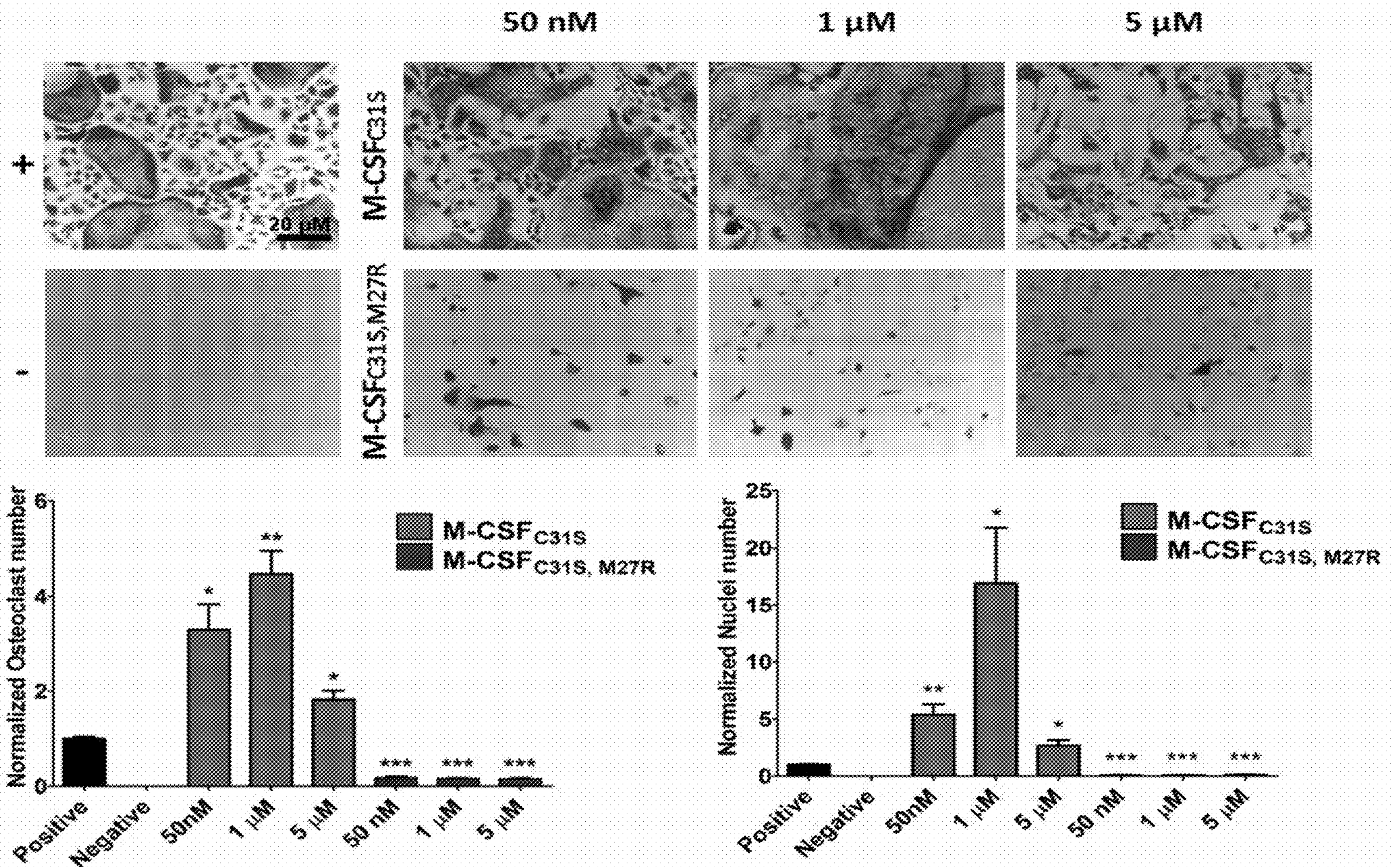

In light of the above-described decrease in phosphorylation, it was hypothesized that incubation of M-CSF$_{C31S,M27R}$ with differentiating monocytes would result in decreased formation of osteoclasts. To test this premise, either BMMs or CD14$^{+}$ cells were incubated with murine or human M-CSF$_{WT}$ (20 ng/ml), respectively, and murine RANKL (20 ng/ml) together with M-CSF$_{C31S}$ and M-CSF$_{C31S,M27R}$ at concentrations of 50 and 1000 and 5000 nM for BMMs and 50, 250, 1000 nM for CD 14$^{+}$ cells. The cells were allowed to differentiate for 96 h or until they reached full differentiation. In BMMs incubated with M-CSF$_{C31S}$, osteoclasts formed rapidly, and therefore they differentiated only for 72 h. Then, the cells were stained with a tartrate-resistant acid phosphatase (TRAP) staining kit (FIGS. 19A, B). It was observed that in the presence of M-CSF$_{C31S}$, osteoclast formation was highly accelerated in the two lower concentrations and was significantly inhibited, in a dose-dependent manner, in the presence of M-CSF$_{C31S,M27R}$. The number of osteoclasts and the number of nuclei for each sample were quantified—exposure to M-CSF$_{C31S,M27R}$ led to a decrease in both parameters, in a dose-dependent manner, while M-CSF$_{C31S}$ produced the opposite result for 50 and 1000 nM concentrations (FIGS. 19A, B). Surprisingly, M-CSF$_{C31S}$ at a concentration of 5000 nM showed a reduction in both osteoclasts and nuclei number, suggesting that its agonistic activity occurs only at a certain concentration range. This inhibition of differentiation behavior was observed also for M-CSF$_{WT}$. These results are in agreement with the phosphorylation assay, i.e., the binding of M-CSF$_{C31S,M27R}$ to c-FMS prevented c-FMS dimerization and phosphorylation, which, in turn, prevented the differentiation of monocytes into osteoclasts.

In order to examine whether M-CSF$_{C31S}$ agonizes c-FMS in the same manner as human M-CSF$_{WT}$, another BMMs differentiation assay was performed in the presence of 50, 1000 and 5000 nM human M-CSF$_{WT}$ without the presence of murine M-CSF$_{WT}$. Human M-CSF$_{WT}$, in this concentration range, inhibits both the numbers of osteoclasts and their nuclei, in a dose dependent manner. Interestingly, in all the concentrations tested, human M-CSF$_{WT}$ was more active than M-CSF$_{C31S}$ in inhibiting cell differentiation suggesting that the latter is a better c-FMS agonist.

Example 15

Figure 20A:
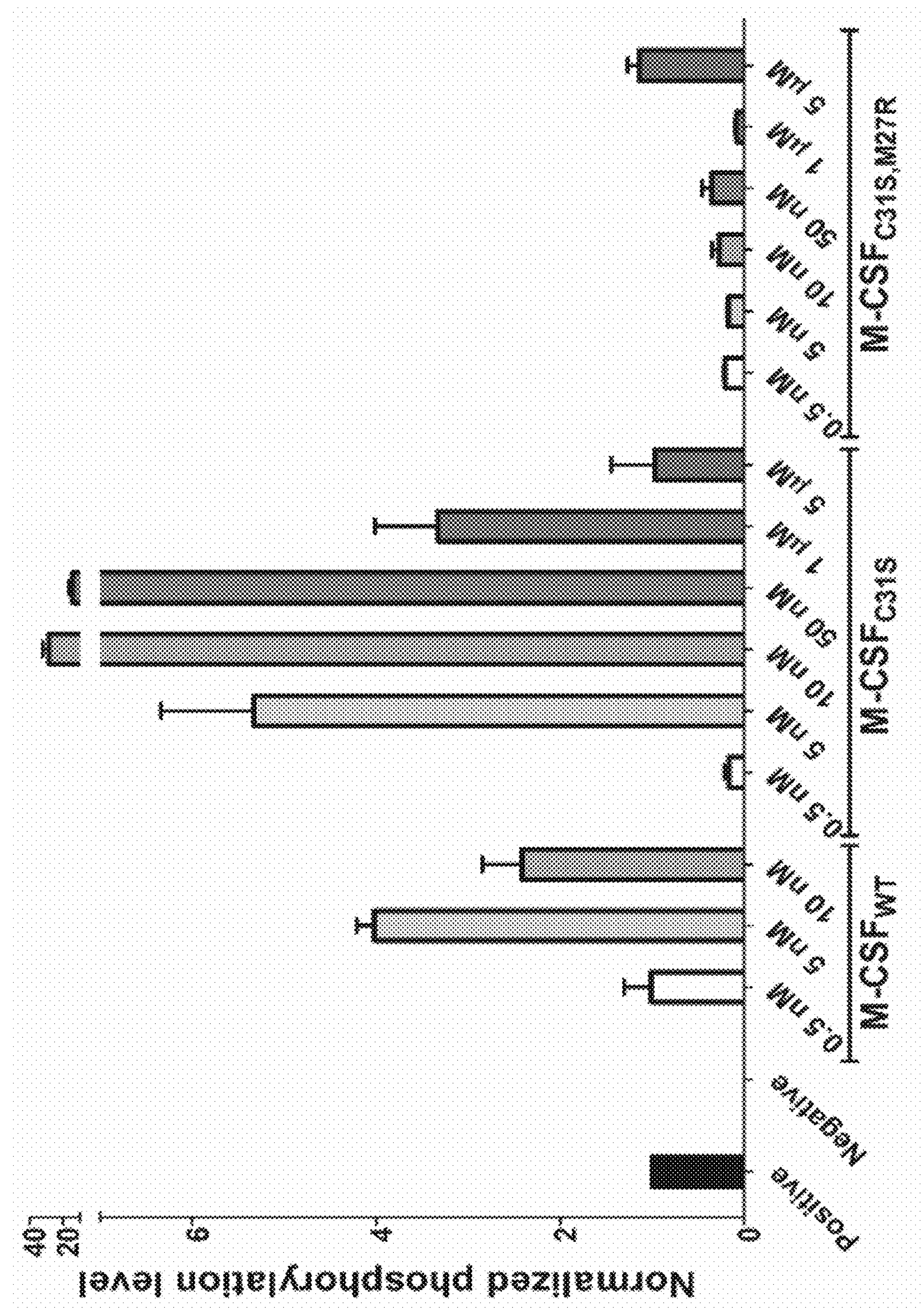
Figure 20B:
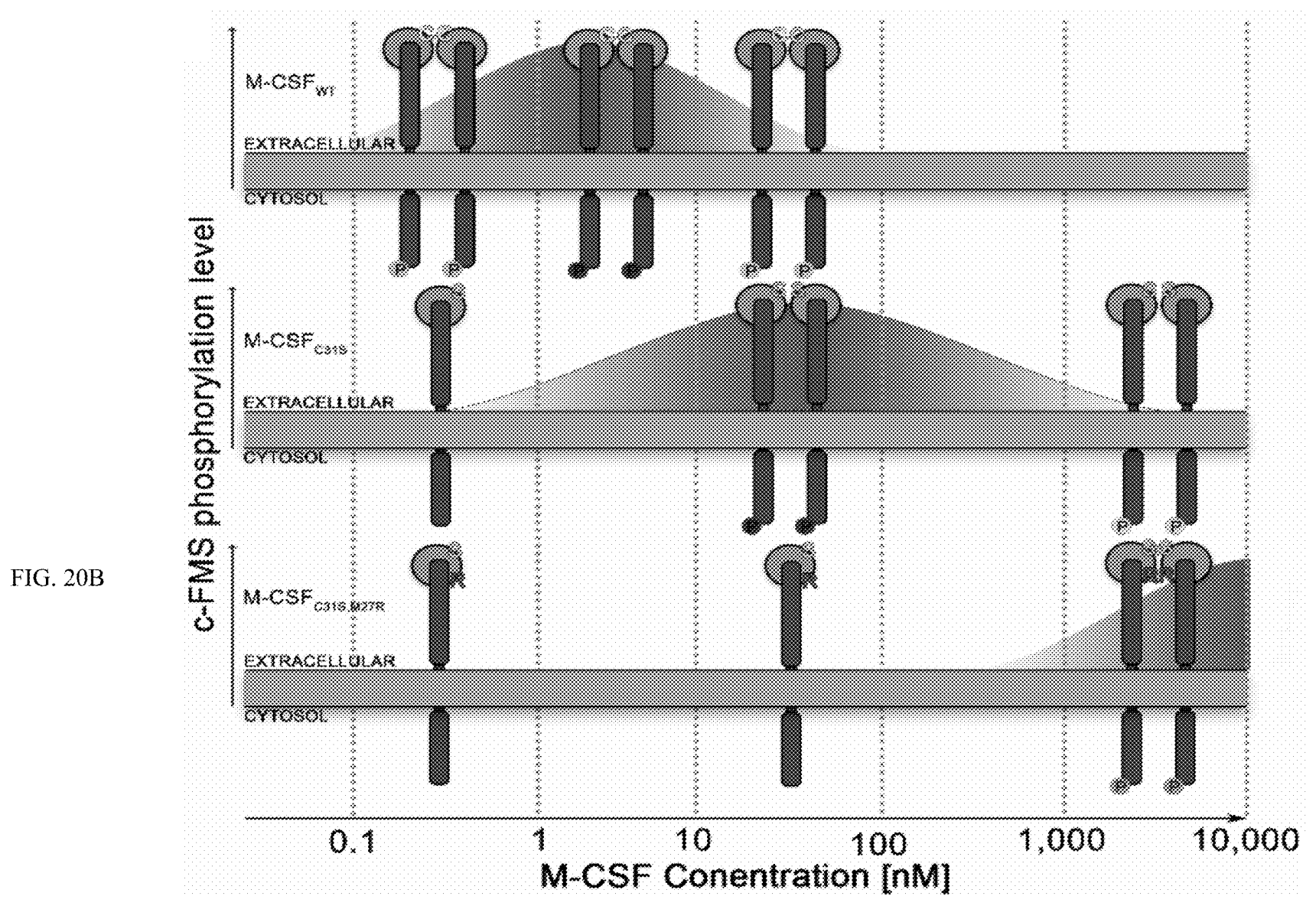

M-CSF$_{WT}$. M-CSF$_{C31S}$ and M-CSF$_{C31S,M27R}$ Show Different c-FMS Activation/Inhibition Potencies In order to elucidate the underlying mechanisms and dose-response nature of each M-CSF variant, a phosphorylation assay was performed using different concentrations of the M-CSF proteins. M-CSF$_{WT}$. M-CSF$_{C31S}$ and M-CSF$_{C31S,M27R}$ were incubated with BMMs for 1 minute without murine M-CSF. The concentrations of M-CSF$_{WT}$ and M-CSF$_{C31S}$ (0.5-10 nM and 0.5-5000 nM, respectively) were chosen to allow bell-shaped curve activation, as seen for the differentiation assay. As expected, the bell-shaped curve occurred for M-CSF$_{WT}$ at lower concentrations than M-CSF$_{C31S}$ peaking at 5 nM and 10 nM, respectively. Interestingly, at the peak concentration, M-CSF$_{C31S}$ led to 10-fold increased phosphorylation compared to M-CSF$_{WT}$ and 40-fold compared to the positive control. In contrast, M-CSF$_{C31S,M27R}$ showed very limited c-FMS phosphorylation at any concentration other than 5 μM. At this concentration it is likely that M-CSF$_{C31S,M27R}$ starts to dimerize, allowing c-FMS activation (FIG. 20A).

In order to shed light on the agonistic/antagonistic properties of each of the M-CSF variants we have conducted a phosphorylation experiment using a broad range of concentrations of these proteins. The range of concentrations we used was selected to allow the formation of a bell-shaped curve typical for M-CSF/c-FMS activation and inhibition. As expected, M-CSF$_{WT}$ and M-CSF$_{C31S}$ showed a similar curve in different protein concentrations with M-CSF$_{WT}$ phosphorylating c-FMS at lower concentrations. Unexpectedly, M-CSF$_{C31S}$ prompted much higher phosphorylation levels than M-CSF$_{WT}$, with a 10-fold increase in phosphorylated c-FMS at 10 nM. M-CSF$_{C31S,M27R}$ did not exhibit phosphorylation capabilities in concentrations lower than 5 μM (FIGS. 20A, B).

Figure 20C:
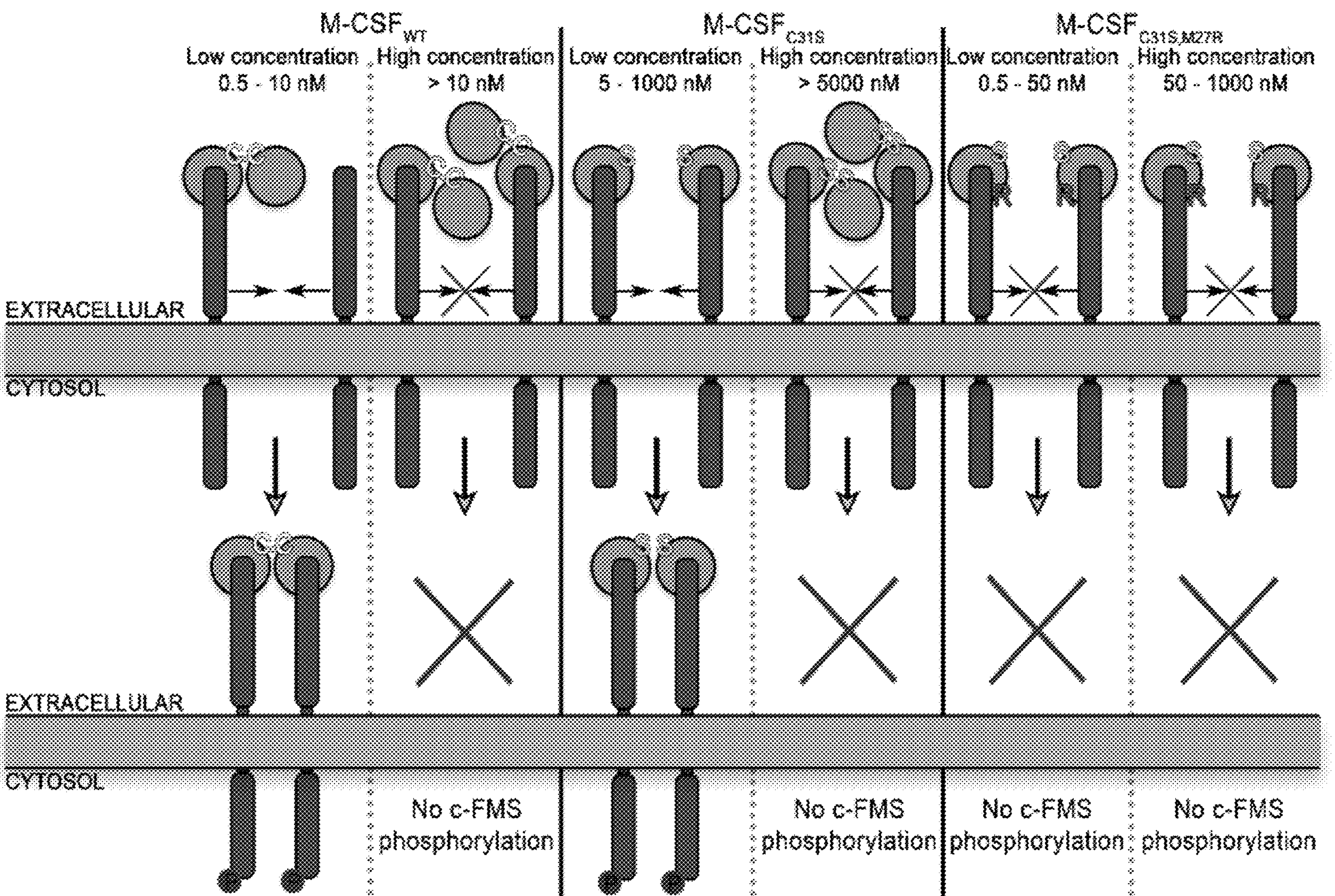

With this in mind it was hypothesized that the mechanism causing this c-FMS activation curve is based on the combination of M-CSF ligand dimerization tendencies and c-FMS molecules that are occupied by the ligand. Therefore, a model for c-FMS activation by these different variants (FIG. 20C) was proposed. For example, it is assumed that in the case of M-CSF$_{WT}$ at concentrations higher than 5 nM, many c-FMS molecules are bound to a covalently dimeric ligand preventing two c-FMS receptor from coming in close proximity, therefore abolishing dimerization and phosphorylation of the receptor. On the other hand, in the case of M-CSF$_{C31S}$ in the same concentration, c-FMS molecules are bound to a monomeric M-CSF$_{C31S}$, thus increasing the local concentration and the driving force for M-CSF dimerization and c-FMS phosphorylation. In the presence of high M-CSF$_{C31S}$ concentrations it becomes a non-covalent dimer, thus leading to the same effect as high M-CSF$_{WT}$ concentrations.

The present study allows better understanding of M-CSF-M-CSF interactions and their influence on M-CSF/c-FMS function. The application of these insights led to the rational engineering of an M-CSF mutant that exhibits promise for further development as a therapeutic. We thus have at our disposal new tools for studying the molecular mechanisms and cell signaling pathways that are related to M-CSF/c-FMS ligand/receptor interactions and, perhaps more importantly, similar biological processes as well.

Example 16

Assessment of the Effect M-CSF5.6 Variant on Bone Resorption

In order to assess the effect of M-CSF variant on bone resorption, 10 weeks old C57 Rcc mice were ovariectomized resulting in a decrease in estrogen secretion similar to what occurs in osteoporosis. Two weeks post-surgery the mice were treated with M-CSF5.6 variant in three concentrations-0.1 mg/kg, 0.5 mg/kg and 15 mg/kg, in order to test the effect on bone resorption and to find the optimal dosage. For a period of 4 days, 0.1 and 0.5 mg/kg M-CSF5.6 treated mice received subcutaneous injections twice a day, while 15 mg/kg M-CSF5.6 treated mice received a daily subcutaneous injection. Mice were sacrificed 18-24 hours after the final injection. The amounts of type I collagen fragments in the blood were measured using CTX-I (carboxy-terminal collagen crosslinks) ELISA.

Figure 21:
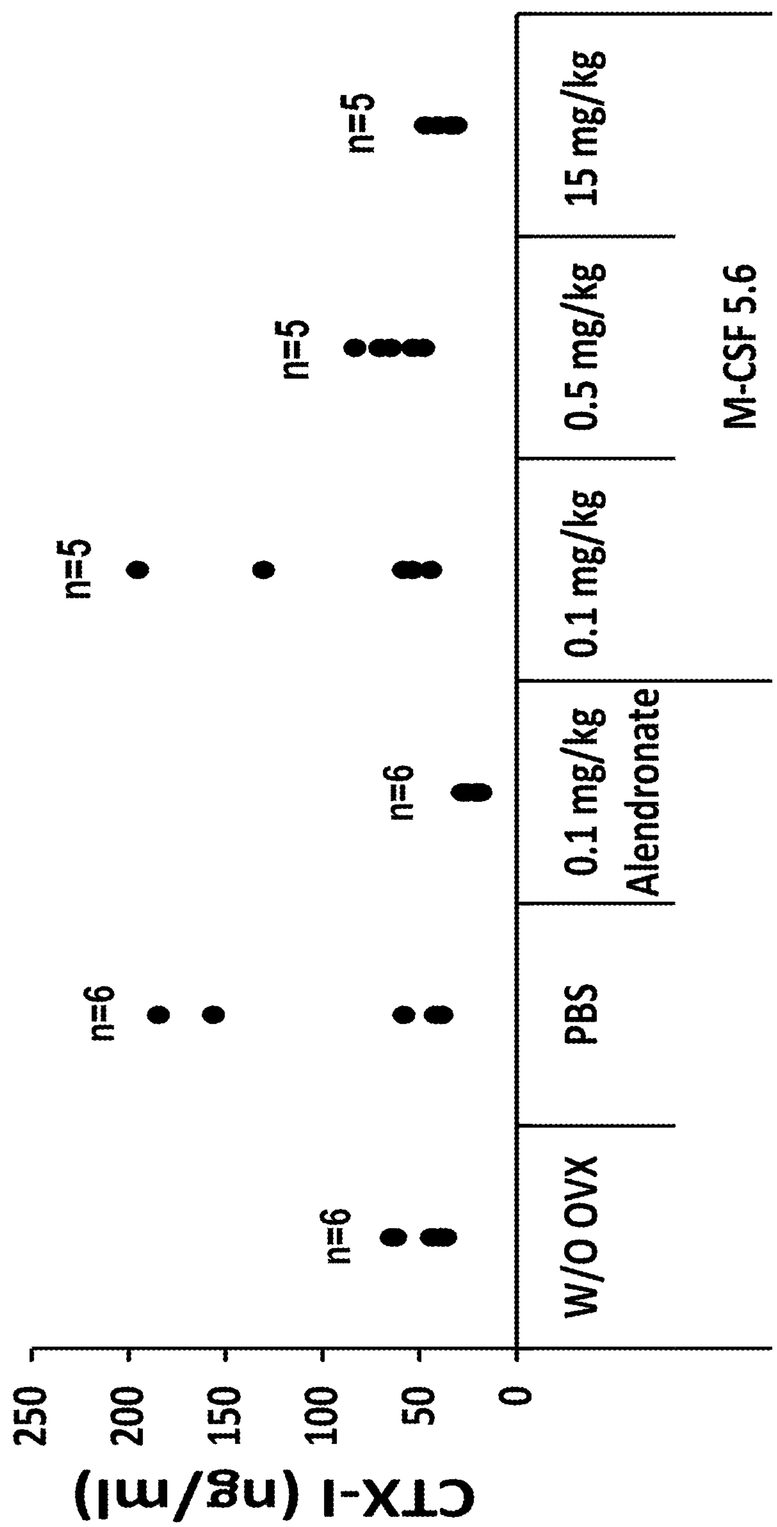
FIG. 21 is a dot plot showing CTX-I serum-concentrations of M-CSF5.6 treated ovariectomized mice. Each black solid dot represents the CTX-I serum-concentration of one animal.

The results are shown in table 2 below and in FIG. 21.

TABLE 2

CTX-I serum-concentration of M-CSF5.6 treated ovariectomized mice.

| | | | 0.1 mg/kg | M-CSF 5.6 | | |
|---|---|---|---|---|---|---|
| n | SHAM | PBS | Alendronate | 0.1 mg/kg | 0.5 mg/kg | 15 mg/kg |
| 1 | 64.45* | 58.02 | 27.86* | 195.2* | 64.67 | 46.82 |
| 2 | 62.20 | 38.40 | 19.1 | 53.32 | 70.37* | 30.85 |
| 3 | 39.02 | 38.39 | 20.9 | 46.69 | 83.09* | 40.68 |
| 4 | 43.17 | 184.4* | 25.4 | 58.19 | 53.33 | 33.94 |
| 5 | 43.61 | 156.10 | 20.03* | 44.06 | 209.7+ | 33.49 |
| 6 | 36.41 | 41.64 | 18.21* | 130.4* | 47.65*^ | 214.7^+ |

Animals were randomly divided into 2 control groups (SHAM, PBS) and 4 treatment groups (0.1, 0.5 and 15 mg/kg M-CSF5.6 and 0.1 mg/kg Alendronate as positive control). Except for the SHAM group, all animals were ovariectomized. *, ^, + represent a Haemolytic-serum sample, an unsuccessful ovariectomy procedure (as determined post mortem) and an outlier, respectively. CTX-I serum-concentration values of mice with unsuccessful ovariectomy were excluded from the analysis.

Figure 22A:
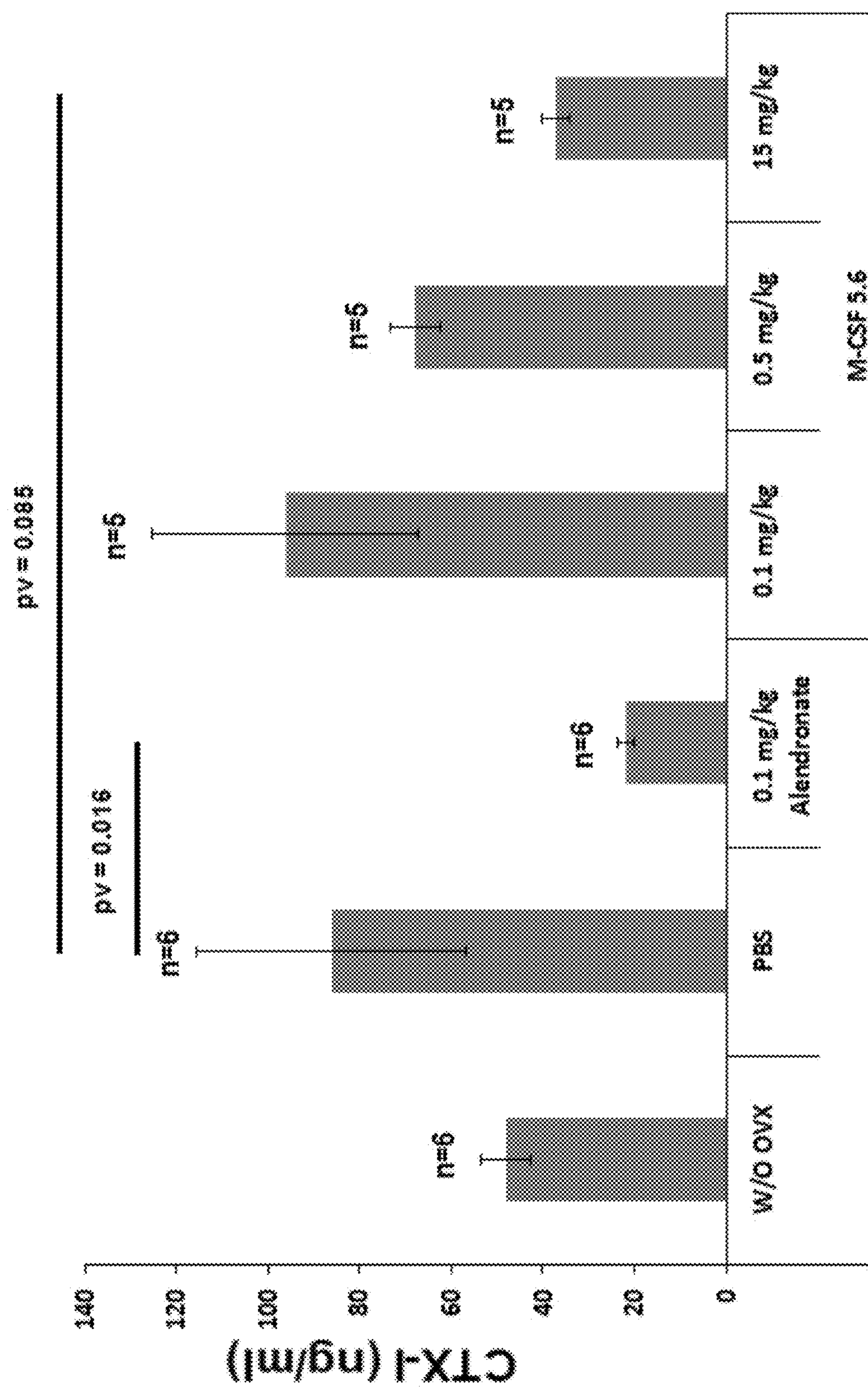
FIGS. 22A-22B are bar graphs showing Mean CTX-I serum-concentrations of M-CSF5.6 treated ovariectomized mice (22A) and (22B) show the mean CTX-I serum concentrations with or without haemolytic samples, respectively. The error bars represent the standard error of the sample mean.
Figure 22B:
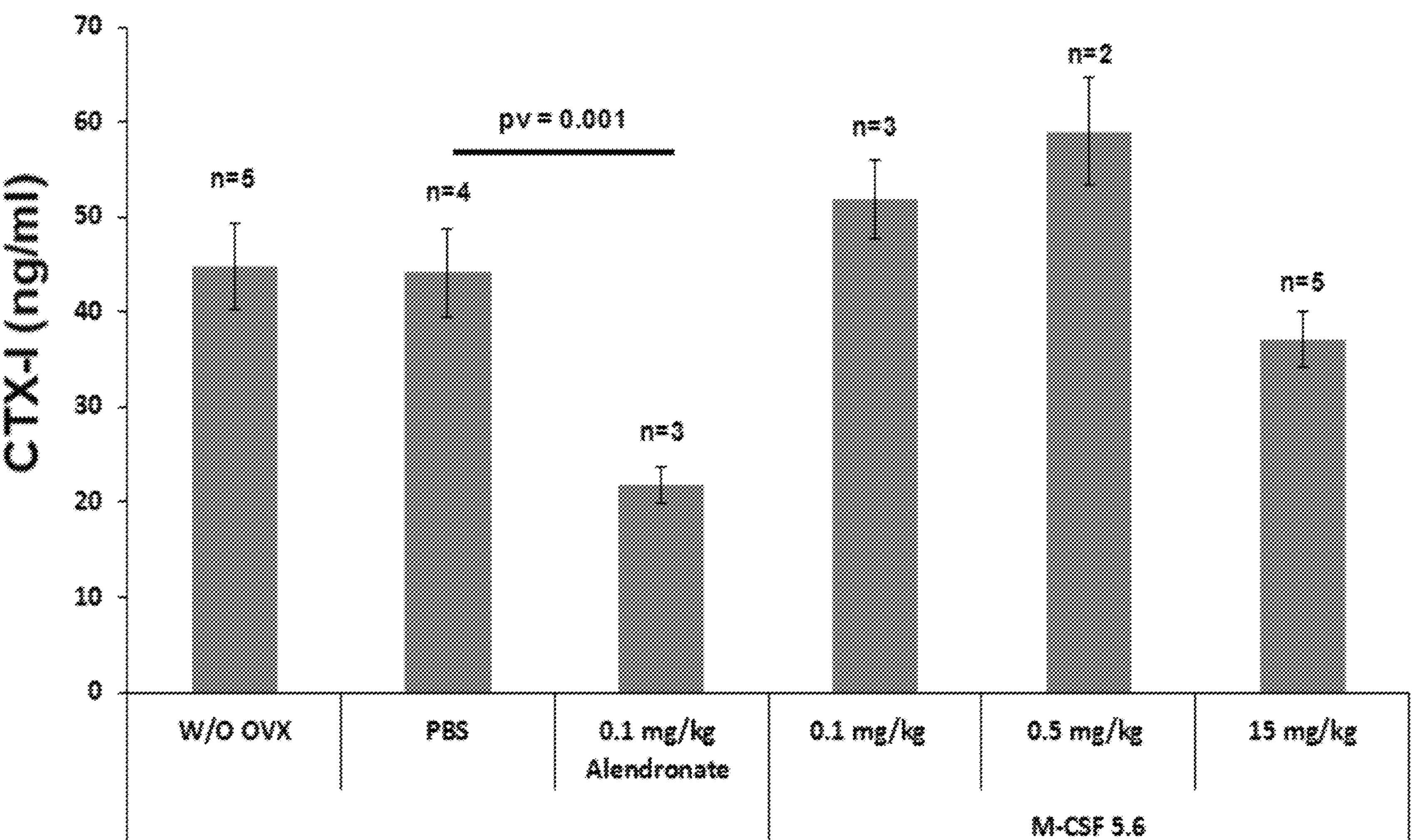

The results support the notion that M-CSF 5.6 is able to reduce CTX-I in vivo. Mice treated with 15 mg/kg M-CSF 5.6 showed ~2-fold decrease in CTX-I levels, compared to the PBS treated animals (FIG. 22A). The effect was even more prominent in the hemolyzed samples (FIG. 15B). Since the ovariectomy did not cause a significant change in CTX-I levels (FIG. 22A, B) it is expected that in a true pathological state, the effect of M-CSF 5.6 will be more prominent and significant.

Importantly, independently of the hemolytic status of the sample, a significant decrease in CTX-I levels in animals that received 0.1 mg/kg Alendronate, compared to the PBS treated animals was observed (FIG. 22A, B). This result is expected since Alendronate treatment is known to reduce CTX-I levels. In addition, when the hemolytic samples are included in the analysis (FIG. 22A), there is a clear dose-response effect which shows that lower doses of M-CSF 5.6 (0.1 and 0.5 mg/kg) are ineffective. Taking into account that CTX-I levels were not affected by the ovariectomy operation (FIG. 22A, B).

Example 17

M-CSF$_{RGD}$ Inhibits Actin Ring Formation in Mature Osteoclasts

Figure 23:
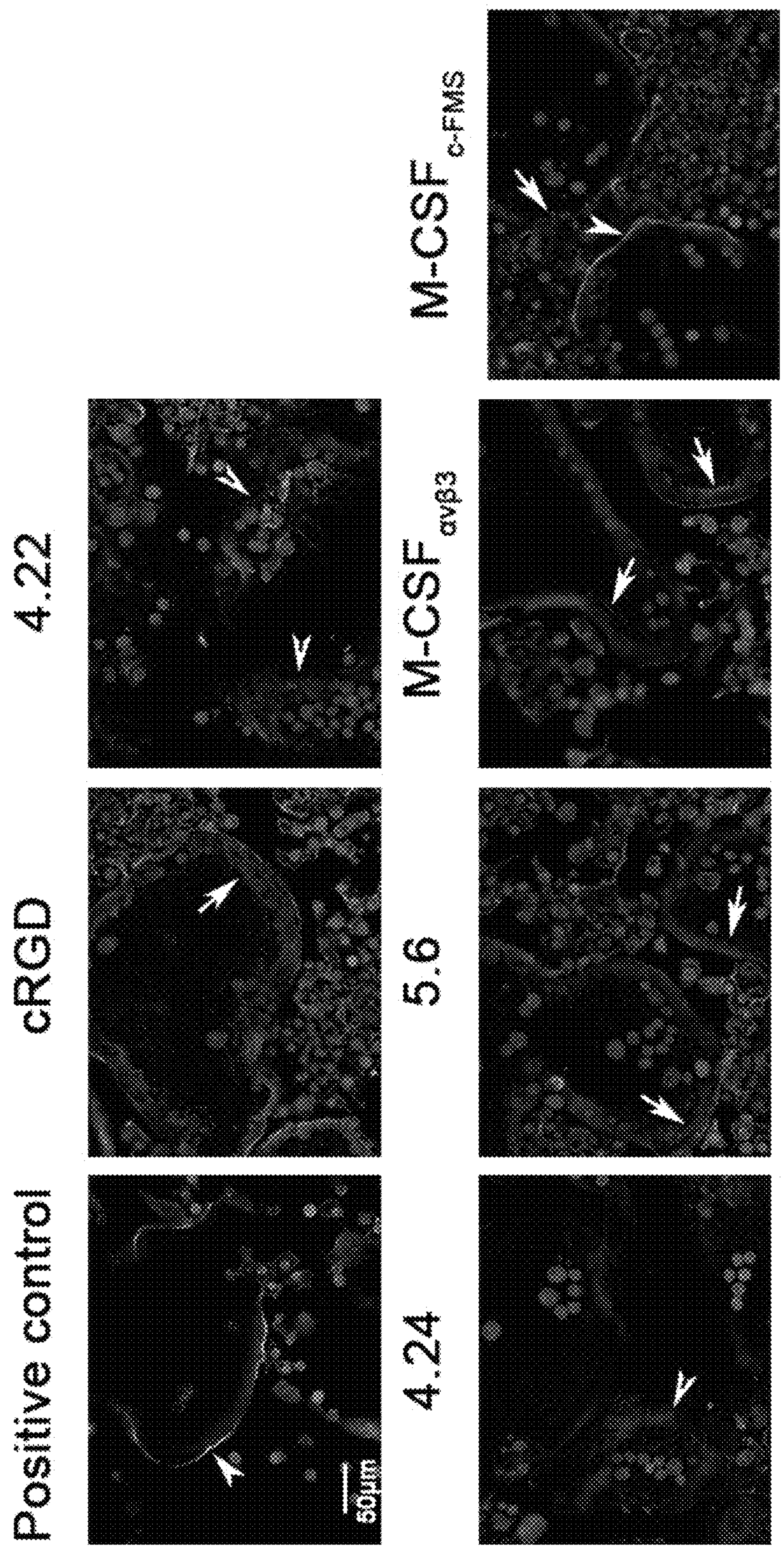
FIG. 23 are example pictures showing Actin ring formation in mature osteoclasts incubated with M-$CSF_{RGD}$ variants. Murine BMMs were allowed to differentiate into osteoclasts in the presence of M-CSF and RANKL for 72 h. Then, the cells were incubated for additional 24 h without (positive control) or with inhibitors (5 μM) followed by fixation and staining for F-actin and nuclei. Cells were able to form a solid actin ring (white arrowheads), scattered actin ring (white arrows) or amorphous actin distribution (barbed arrowheads). Pictures are representatives of 35 images acquired from five different wells per sample.

For a mature osteoclast to resorb bone properly, it must form unique structure termed "sealing zone"; this structure consists of an actin ring made from a dense actin mesh connected by adhesion complexes called podosomes. The formation of the actin ring involves several stages: at the beginning, podosomes are formed throughout the cell in a scattered manner, then groups of podosomes form small actin structures named belts and upon osteoclast maturation, the belts are moving to the cell periphery, cluster, and form the actin ring. Podosomes contain high levels of $\alpha_v\beta_3$ integrin which is essential for the formation of a proper actin ring with condensed podosome network. To test whether inhibition of $\alpha_v\beta_3$ integrin by bispecific M-CSF$_{RGD}$ variants effect the formation of actin rings, mouse BMMs were allowed to differentiate into mature osteoclasts to the point that multinucleated cells were formed and exhibited an actin ring structure. At this point, the inhibitors were added, and the cells were incubated for an additional 24 h before they were fixed and stained. Cells incubated only with M-CSF and RANKL without any inhibitor (i.e., positive control) formed a dense continuous actin ring structure. Addition of the monospecific M-CSF$_{c\text{-}FMS}$ did not drastically inhibit actin ring formation, and osteoclasts presenting dense continuous actin rings were observed; nevertheless, scattered podosomes presenting immature rings were more abundant as compared to the positive controls. Addition of either cyclic RGD peptide, a well-established $\alpha_v\beta_3$ integrin inhibitor, or the monospecific M-CSF$_{\alpha v\beta 3}$ decreased the condensation and density of podosomes, and actin rings appeared less pronounced, wider and diffusible with high distribution of scattered podosomes. The bispecific M-CSF$_{RGD}$ variant 5.6, which exhibited the lowest affinity to $\alpha_v\beta_3$ integrin, showed the same phenotype as cRGD and M-CSF$_{\alpha v\beta 3}$. Strikingly, when the bispecific M-CSF$_{RGD}$ variants 4.22 and 4.24 were added, osteoclasts did not form any actin rings or even scattered podosomes, and instead, the actin formed diffusible structures which spread randomly all around the cell surface (FIG. 23).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A polypeptide comprising an amino acid sequence selected from the group consisting of SEQ ID NO: 12, SEQ ID NO: 13, SEQ ID NO: 16, and SEQ ID NO: 19, wherein said polypeptide is characterized by antagonizing c-FMS and/or impairing osteoclast differentiation, and wherein said polypeptide may be further characterized by having diminished non-covalent dimerization.

2. The polypeptide of claim 1, wherein said polypeptide comprises an amino acid sequence selected from the group consisting of SEQ ID NO: 16 and SEQ ID NO: 19, and wherein residues 25-32 of said SEQ ID NO: 16 or SEQ ID NO: 19 is an RGD motif selected from the group consisting of: SEQ ID NO: 8 (QTRGDSPS), SEQ ID NO: 9 (TYPRGDMCS), and SEQ ID NO: 10 (EPVRGDNIN).

3. An isolated nucleic acid molecule encoding the polypeptide of claim 1.

4. An expression vector comprising the nucleic acid of claim 3.

5. A cell transformed or transfected with the expression vector of claim 4.

6. A pharmaceutical composition comprising the polypeptide of claim 1 and a pharmaceutical acceptable carrier.

7. A method for treating a disease characterized by excessive osteoclast differentiation or increased bone resorption in a subject in need thereof, the method comprising the step of administering to said subject a therapeutically effective amount of a pharmaceutical composition comprising the polypeptide of claim 1 and a pharmaceutical acceptable carrier, thereby treating a disease characterized by excessive osteoclast differentiation or increased bone resorption in a subject in need thereof.

8. The method of claim 7, wherein said disease associated with increased bone resorption is osteoporosis.

* * * * *

SEQUENCE LISTING

<160> NUMBER OF SEQ ID NOS: 19

<210> SEQ ID NO 1
<211> LENGTH: 157
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (31)..(31)
<223> OTHER INFORMATION: X is any amino acid other than cysteine
<220> FEATURE:
<221> NAME/KEY: MISC_FEATURE
<222> LOCATION: (31)..(31)
<223> OTHER INFORMATION: X is any amino acid other than Cysteine

<400> SEQUENCE: 1

Glu Glu Val Ser Glu Tyr Cys Ser His Met Ile Gly Ser Gly His Leu
1 5 10 15

Gln Ser Leu Gln Arg Leu Ile Asp Ser Gln Met Glu Thr Ser Xaa Gln
20 25 30

Ile Thr Phe Glu Phe Val Asp Gln Glu Gln Leu Lys Asp Pro Val Cys
35 40 45

Tyr Leu Lys Lys Ala Phe Leu Leu Val Gln Asp Ile Met Glu Asp Thr
50 55 60

Met Arg Phe Arg Asp Asn Thr Glu Pro Val Arg Gly Asp Asn Ile Asn
65 70 75 80

Pro Asn Ala Ile Ala Ile Val Gln Leu Gln Glu Leu Ser Leu Arg Leu
85 90 95

Lys Ser Cys Phe Thr Lys Asp Tyr Glu Glu His Asp Lys Ala Cys Val
100 105 110

Arg Thr Phe Tyr Glu Thr Pro Leu Gln Leu Leu Glu Lys Val Lys Asn
115 120 125

Val Phe Asn Glu Thr Lys Asn Leu Leu Asp Lys Asp Trp Asn Ile Phe
130 135 140

Ser Lys Asn Cys Asn Asn Ser Phe Ala Glu Cys Ser Ser
145 150 155

<210> SEQ ID NO 2
<211> LENGTH: 158
<212> TYPE: PRT
<213> ORGANISM: Artificial Sequence
<220> FEATURE:
<223> OTHER INFORMATION: Synthetic peptide

<400> SEQUENCE: 2

Glu Glu Val Ser Glu Tyr Cys Ser His Met Ile Gly Ser Gly His Leu
1 5 10 15

```
Gln Ser Leu Gln Arg Leu Ile Asp Ser Gln Met Glu Thr Ser Ser Gln
            20                  25                  30

Ile Thr Phe Glu Phe Val Asp Gln Glu Gln Leu Lys Asp Pro Val Cys
        35                  40                  45

Tyr Leu Lys Lys Ala Phe Leu Leu Val Gln Asp Ile Met Glu Asp Thr
    50                  55                  60

Met Arg Phe Arg Asp Asn Thr Pro Asn Ala Ile Ala Ile Val Gln Leu
65                  70                  75                  80

Gln Glu Leu Ser Leu Arg Leu Lys Ser Cys Phe Thr Lys Asp Tyr Glu
                85                  90                  95

Glu His Asp Lys Ala Cys Val Arg Thr Phe Tyr Glu Thr Pro Leu Gln
            100                 105                 110

Leu Leu Glu Lys Val Lys Asn Val Phe Asn Glu Thr Lys Asn Leu Leu
        115                 120                 125

Asp Lys Asp Trp Asn Ile Phe Ser Lys Asn Cys Asn Asn Ser Phe Ala
    130                 135                 140

Glu Cys Ser Ser Gln Gly His Glu Arg Gln Ser Glu Gly Ser
145                 150                 155


<210> SEQ ID NO 3
<211> LENGTH: 24
<212> TYPE: PRT
<213> ORGANISM: Artificial Sequence
<220> FEATURE:
<223> OTHER INFORMATION: Synthetic peptide

<400> SEQUENCE: 3

Glu Glu Val Ser Glu Tyr Cys Ser His Met Ile Gly Ser Gly His Leu
1               5                   10                  15

Gln Ser Leu Gln Arg Leu Ile Asp
            20


<210> SEQ ID NO 4
<211> LENGTH: 31
<212> TYPE: PRT
<213> ORGANISM: Artificial Sequence
<220> FEATURE:
<223> OTHER INFORMATION: Synthetic peptide

<400> SEQUENCE: 4

Ile Thr Phe Glu Phe Val Asp Gln Glu Gln Leu Lys Asp Pro Val Cys
1               5                   10                  15

Tyr Leu Lys Lys Ala Phe Leu Leu Val Gln Asp Ile Met Glu Asp
            20                  25                  30


<210> SEQ ID NO 5
<211> LENGTH: 77
<212> TYPE: PRT
<213> ORGANISM: Artificial Sequence
<220> FEATURE:
<223> OTHER INFORMATION: Synthetic peptide

<400> SEQUENCE: 5

Pro Asn Ala Ile Ala Ile Val Gln Leu Gln Glu Leu Ser Leu Arg Leu
1               5                   10                  15

Lys Ser Cys Phe Thr Lys Asp Tyr Glu Glu His Asp Lys Ala Cys Val
            20                  25                  30

Arg Thr Phe Tyr Glu Thr Pro Leu Gln Leu Leu Glu Lys Val Lys Asn
        35                  40                  45

Val Phe Asn Glu Thr Lys Asn Leu Leu Asp Lys Asp Trp Asn Ile Phe
```

```
    50                  55                  60

Ser Lys Asn Cys Asn Asn Ser Phe Ala Glu Cys Ser Ser
65                  70                  75


<210> SEQ ID NO 6
<211> LENGTH: 3
<212> TYPE: PRT
<213> ORGANISM: Artificial Sequence
<220> FEATURE:
<223> OTHER INFORMATION: Synthetic peptide

<400> SEQUENCE: 6

Arg Gly Asp
1


<210> SEQ ID NO 7
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(3)
<223> OTHER INFORMATION: X is any amino acid
<220> FEATURE:
<221> NAME/KEY: MISC_FEATURE
<222> LOCATION: (7)..(9)
<223> OTHER INFORMATION: X is any amino acid

<400> SEQUENCE: 7

Xaa Xaa Xaa Arg Gly Asp Xaa Xaa Xaa
1               5


<210> SEQ ID NO 8
<211> LENGTH: 9
<212> TYPE: PRT
<213> ORGANISM: Artificial Sequence
<220> FEATURE:
<223> OTHER INFORMATION: Synthetic peptide

<400> SEQUENCE: 8

Gln Thr Ser Arg Gly Asp Ser Pro Ser
1               5


<210> SEQ ID NO 9
<211> LENGTH: 9
<212> TYPE: PRT
<213> ORGANISM: Artificial Sequence
<220> FEATURE:
<223> OTHER INFORMATION: Synthetic peptide

<400> SEQUENCE: 9

Thr Tyr Pro Arg Gly Asp Met Cys Ser
1               5


<210> SEQ ID NO 10
<211> LENGTH: 9
<212> TYPE: PRT
<213> ORGANISM: Artificial Sequence
<220> FEATURE:
<223> OTHER INFORMATION: Synthetic peptide

<400> SEQUENCE: 10

Glu Pro Val Arg Gly Asp Asn Ile Asn
1               5
```

<210> SEQ ID NO 11
<211> LENGTH: 157
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (27)..(27)
<223> OTHER INFORMATION: X is Arg, His or Lys
<220> FEATURE:
<221> NAME/KEY: MISC_FEATURE
<222> LOCATION: (31)..(31)
<223> OTHER INFORMATION: X is any amino acid other than Cysteine

<400> SEQUENCE: 11

```
Glu Glu Val Ser Glu Tyr Cys Ser His Met Ile Gly Ser Gly His Leu
1               5                   10                  15

Gln Ser Leu Gln Arg Leu Ile Asp Ser Gln Met Glu Thr Ser Xaa Gln
            20                  25                  30

Ile Thr Phe Glu Phe Val Asp Gln Glu Gln Leu Lys Asp Pro Val Cys
        35                  40                  45

Tyr Leu Lys Lys Ala Phe Leu Leu Val Gln Asp Ile Met Glu Asp Thr
    50                  55                  60

Met Arg Phe Arg Asp Asn Thr Glu Pro Val Arg Gly Asp Asn Ile Asn
65                  70                  75                  80

Pro Asn Ala Ile Ala Ile Val Gln Leu Gln Glu Leu Ser Leu Arg Leu
                85                  90                  95

Lys Ser Cys Phe Thr Lys Asp Tyr Glu Glu His Asp Lys Ala Cys Val
            100                 105                 110

Arg Thr Phe Tyr Glu Thr Pro Leu Gln Leu Leu Glu Lys Val Lys Asn
        115                 120                 125

Val Phe Asn Glu Thr Lys Asn Leu Leu Asp Lys Asp Trp Asn Ile Phe
    130                 135                 140

Ser Lys Asn Cys Asn Asn Ser Phe Ala Glu Cys Ser Ser
145                 150                 155
```

<210> SEQ ID NO 12
<211> LENGTH: 149
<212> TYPE: PRT
<213> ORGANISM: Artificial Sequence
<220> FEATURE:
<223> OTHER INFORMATION: Synthetic peptide

<400> SEQUENCE: 12

```
Glu Glu Val Ser Glu Tyr Cys Ser His Met Ile Gly Ser Gly His Leu
1               5                   10                  15

Gln Ser Leu Gln Arg Leu Ile Asp Gln Thr Ser Arg Gly Asp Ser Pro
            20                  25                  30

Ser Ile Thr Phe Glu Phe Val Asp Gln Glu Gln Leu Lys Asp Pro Val
        35                  40                  45

Cys Tyr Leu Lys Lys Ala Phe Leu Leu Val Gln Asp Ile Met Glu Asp
    50                  55                  60

Thr Met Arg Phe Arg Asp Asn Thr Pro Asn Ala Ile Ala Ile Val Gln
65                  70                  75                  80

Leu Gln Glu Leu Ser Leu Arg Leu Lys Ser Cys Phe Thr Lys Asp Tyr
                85                  90                  95

Glu Glu His Asp Lys Ala Cys Val Arg Thr Phe Tyr Glu Thr Pro Leu
            100                 105                 110

Gln Leu Leu Glu Lys Val Lys Asn Val Phe Asn Glu Thr Lys Asn Leu
```

```
        115                 120                 125

Leu Asp Lys Asp Trp Asn Ile Phe Ser Lys Asn Cys Asn Asn Ser Phe
    130                 135                 140

Ala Glu Cys Ser Ser
145


<210> SEQ ID NO 13
<211> LENGTH: 149
<212> TYPE: PRT
<213> ORGANISM: Artificial Sequence
<220> FEATURE:
<223> OTHER INFORMATION: Synthetic peptide

<400> SEQUENCE: 13

Glu Glu Val Ser Glu Tyr Cys Ser His Met Ile Gly Ser Gly His Leu
1               5                   10                  15

Gln Ser Leu Gln Arg Leu Ile Asp Thr Tyr Pro Arg Gly Asp Met Cys
            20                  25                  30

Ser Ile Thr Phe Glu Phe Val Asp Gln Glu Gln Leu Lys Asp Pro Val
        35                  40                  45

Cys Tyr Leu Lys Lys Ala Phe Leu Leu Val Gln Asp Ile Met Glu Asp
    50                  55                  60

Thr Met Arg Phe Arg Asp Asn Thr Pro Asn Ala Ile Ala Ile Val Gln
65                  70                  75                  80

Leu Gln Glu Leu Ser Leu Arg Leu Lys Ser Cys Phe Thr Lys Asp Tyr
                85                  90                  95

Glu Glu His Asp Lys Ala Cys Val Arg Thr Phe Tyr Glu Thr Pro Leu
            100                 105                 110

Gln Leu Leu Glu Lys Val Lys Asn Val Phe Asn Glu Thr Lys Asn Leu
        115                 120                 125

Leu Asp Lys Asp Trp Asn Ile Phe Ser Lys Asn Cys Asn Asn Ser Phe
    130                 135                 140

Ala Glu Cys Ser Ser
145


<210> SEQ ID NO 14
<211> LENGTH: 149
<212> TYPE: PRT
<213> ORGANISM: Artificial Sequence
<220> FEATURE:
<223> OTHER INFORMATION: Synthetic peptide

<400> SEQUENCE: 14

Glu Glu Val Ser Glu Tyr Cys Ser His Met Ile Gly Ser Gly His Leu
1               5                   10                  15

Gln Ser Leu Gln Arg Leu Ile Asp Ser Gln Met Glu Thr Ser Ser Gln
            20                  25                  30

Ile Thr Phe Glu Phe Val Asp Gln Glu Gln Leu Lys Asp Pro Val Cys
        35                  40                  45

Tyr Leu Lys Lys Ala Phe Leu Leu Val Gln Asp Ile Met Glu Asp Glu
    50                  55                  60

Pro Val Arg Gly Asp Asn Ile Asn Pro Asn Ala Ile Ala Ile Val Gln
65                  70                  75                  80

Leu Gln Glu Leu Ser Leu Arg Leu Lys Ser Cys Phe Thr Lys Asp Tyr
                85                  90                  95

Glu Glu His Asp Lys Ala Cys Val Arg Thr Phe Tyr Glu Thr Pro Leu
            100                 105                 110
```

```
Gln Leu Leu Glu Lys Val Lys Asn Val Phe Asn Glu Thr Lys Asn Leu
        115                 120                 125

Leu Asp Lys Asp Trp Asn Ile Phe Ser Lys Asn Cys Asn Asn Ser Phe
    130                 135                 140

Ala Glu Cys Ser Ser
145


<210> SEQ ID NO 15
<211> LENGTH: 157
<212> TYPE: PRT
<213> ORGANISM: Artificial Sequence
<220> FEATURE:
<223> OTHER INFORMATION: Synthetic peptide

<400> SEQUENCE: 15

Glu Glu Val Ser Glu Tyr Cys Ser His Met Ile Gly Ser Gly His Leu
1               5                   10                  15

Gln Ser Leu Gln Arg Leu Ile Asp Ser Gln Arg Glu Thr Ser Ser Gln
            20                  25                  30

Ile Thr Phe Glu Phe Val Asp Gln Glu Gln Leu Lys Asp Pro Val Cys
        35                  40                  45

Tyr Leu Lys Lys Ala Phe Leu Leu Val Gln Asp Ile Met Glu Asp Thr
    50                  55                  60

Met Arg Phe Arg Asp Asn Thr Glu Pro Val Arg Gly Asp Asn Ile Asn
65                  70                  75                  80

Pro Asn Ala Ile Ala Ile Val Gln Leu Gln Glu Leu Ser Leu Arg Leu
                85                  90                  95

Lys Ser Cys Phe Thr Lys Asp Tyr Glu Glu His Asp Lys Ala Cys Val
            100                 105                 110

Arg Thr Phe Tyr Glu Thr Pro Leu Gln Leu Leu Glu Lys Val Lys Asn
        115                 120                 125

Val Phe Asn Glu Thr Lys Asn Leu Leu Asp Lys Asp Trp Asn Ile Phe
    130                 135                 140

Ser Lys Asn Cys Asn Asn Ser Phe Ala Glu Cys Ser Ser
145                 150                 155


<210> SEQ ID NO 16
<211> LENGTH: 457
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (25)..(25)
<223> OTHER INFORMATION: X is Gln or Thr
<220> FEATURE:
<221> NAME/KEY: MISC_FEATURE
<222> LOCATION: (26)..(26)
<223> OTHER INFORMATION: X is Thr or Tyr
<220> FEATURE:
<221> NAME/KEY: MISC_FEATURE
<222> LOCATION: (27)..(27)
<223> OTHER INFORMATION: X is Ser or Pro
<220> FEATURE:
<221> NAME/KEY: MISC_FEATURE
<222> LOCATION: (31)..(31)
<223> OTHER INFORMATION: X is Seq or Met
<220> FEATURE:
<221> NAME/KEY: MISC_FEATURE
<222> LOCATION: (31)..(31)
<223> OTHER INFORMATION: X is Ser or Met
<220> FEATURE:
<221> NAME/KEY: MISC_FEATURE
<222> LOCATION: (32)..(32)
```

<223> OTHER INFORMATION: X is Pro or Cys

<400> SEQUENCE: 16

```
Glu Glu Val Ser Glu Tyr Cys Ser His Met Ile Gly Ser Gly His Leu
1               5                   10                  15

Gln Ser Leu Gln Arg Leu Ile Asp Xaa Xaa Xaa Arg Gly Asp Xaa Xaa
            20                  25                  30

Ser Ile Thr Phe Glu Phe Val Asp Gln Glu Gln Leu Lys Asp Pro Val
        35                  40                  45

Cys Tyr Leu Lys Lys Ala Phe Leu Leu Val Gln Asp Ile Met Glu Asp
    50                  55                  60

Thr Met Arg Phe Arg Asp Asn Thr Pro Asn Ala Ile Ala Ile Val Gln
65                  70                  75                  80

Leu Gln Glu Leu Ser Leu Arg Leu Lys Ser Cys Phe Thr Lys Asp Tyr
                85                  90                  95

Glu Glu His Asp Lys Ala Cys Val Arg Thr Phe Tyr Glu Thr Pro Leu
            100                 105                 110

Gln Leu Leu Glu Lys Val Lys Asn Val Phe Asn Glu Thr Lys Asn Leu
        115                 120                 125

Leu Asp Lys Asp Trp Asn Ile Phe Ser Lys Asn Cys Asn Asn Ser Phe
    130                 135                 140

Ala Glu Cys Ser Ser Gln Asp Val Val Thr Lys Pro Asp Cys Asn Cys
145                 150                 155                 160

Leu Tyr Pro Lys Ala Ile Pro Ser Ser Asp Pro Ala Ser Val Ser Pro
                165                 170                 175

His Gln Pro Leu Ala Pro Ser Met Ala Pro Val Ala Gly Leu Thr Trp
            180                 185                 190

Glu Asp Ser Glu Gly Thr Glu Gly Ser Ser Leu Leu Pro Gly Glu Gln
        195                 200                 205

Pro Leu His Thr Val Asp Pro Gly Ser Ala Lys Gln Arg Pro Pro Arg
    210                 215                 220

Ser Thr Cys Gln Ser Phe Glu Pro Pro Glu Thr Pro Val Val Lys Asp
225                 230                 235                 240

Ser Thr Ile Gly Gly Ser Pro Gln Pro Arg Pro Ser Val Gly Ala Phe
                245                 250                 255

Asn Pro Gly Met Glu Asp Ile Leu Asp Ser Ala Met Gly Thr Asn Trp
            260                 265                 270

Val Pro Glu Glu Ala Ser Gly Glu Ala Ser Glu Ile Pro Val Pro Gln
        275                 280                 285

Gly Thr Glu Leu Ser Pro Ser Arg Pro Gly Gly Gly Ser Met Gln Thr
    290                 295                 300

Glu Pro Ala Arg Pro Ser Asn Phe Leu Ser Ala Ser Ser Pro Leu Pro
305                 310                 315                 320

Ala Ser Ala Lys Gly Gln Gln Pro Ala Asp Val Thr Gly Thr Ala Leu
                325                 330                 335

Pro Arg Val Gly Pro Val Arg Pro Thr Gly Gln Asp Trp Asn His Thr
            340                 345                 350

Pro Gln Lys Thr Asp His Pro Ser Ala Leu Leu Arg Asp Pro Pro Glu
        355                 360                 365

Pro Gly Ser Pro Arg Ile Ser Ser Leu Arg Pro Gln Gly Leu Ser Asn
    370                 375                 380

Pro Ser Thr Leu Ser Ala Gln Pro Gln Leu Ser Arg Ser His Ser Ser
385                 390                 395                 400
```

```
Gly Ser Val Leu Pro Leu Gly Glu Leu Glu Gly Arg Arg Ser Thr Arg
            405                 410                 415

Asp Arg Arg Ser Pro Ala Glu Pro Glu Gly Gly Pro Ala Ser Glu Gly
            420                 425                 430

Ala Ala Arg Pro Leu Pro Arg Phe Asn Ser Val Pro Leu Thr Asp Thr
        435                 440                 445

Gly His Glu Arg Gln Ser Glu Gly Ser
    450                 455


<210> SEQ ID NO 17
<211> LENGTH: 457
<212> TYPE: PRT
<213> ORGANISM: Artificial Sequence
<220> FEATURE:
<223> OTHER INFORMATION: Synthetic peptide

<400> SEQUENCE: 17

Glu Glu Val Ser Glu Tyr Cys Ser His Met Ile Gly Ser Gly His Leu
1               5                   10                  15

Gln Ser Leu Gln Arg Leu Ile Asp Ser Gln Met Glu Thr Ser Ser Gln
            20                  25                  30

Ile Thr Phe Glu Phe Val Asp Gln Glu Gln Leu Lys Asp Pro Val Cys
        35                  40                  45

Tyr Leu Lys Lys Ala Phe Leu Leu Val Gln Asp Ile Met Glu Asp Glu
    50                  55                  60

Pro Val Arg Gly Asp Asn Ile Asn Pro Asn Ala Ile Ala Ile Val Gln
65                  70                  75                  80

Leu Gln Glu Leu Ser Leu Arg Leu Lys Ser Cys Phe Thr Lys Asp Tyr
                85                  90                  95

Glu Glu His Asp Lys Ala Cys Val Arg Thr Phe Tyr Glu Thr Pro Leu
            100                 105                 110

Gln Leu Leu Glu Lys Val Lys Asn Val Phe Asn Glu Thr Lys Asn Leu
        115                 120                 125

Leu Asp Lys Asp Trp Asn Ile Phe Ser Lys Asn Cys Asn Asn Ser Phe
    130                 135                 140

Ala Glu Cys Ser Ser Gln Asp Val Val Thr Lys Pro Asp Cys Asn Cys
145                 150                 155                 160

Leu Tyr Pro Lys Ala Ile Pro Ser Ser Asp Pro Ala Ser Val Ser Pro
                165                 170                 175

His Gln Pro Leu Ala Pro Ser Met Ala Pro Val Ala Gly Leu Thr Trp
            180                 185                 190

Glu Asp Ser Glu Gly Thr Glu Gly Ser Ser Leu Leu Pro Gly Glu Gln
        195                 200                 205

Pro Leu His Thr Val Asp Pro Gly Ser Ala Lys Gln Arg Pro Pro Arg
    210                 215                 220

Ser Thr Cys Gln Ser Phe Glu Pro Pro Glu Thr Pro Val Val Lys Asp
225                 230                 235                 240

Ser Thr Ile Gly Gly Ser Pro Gln Pro Arg Pro Ser Val Gly Ala Phe
                245                 250                 255

Asn Pro Gly Met Glu Asp Ile Leu Asp Ser Ala Met Gly Thr Asn Trp
            260                 265                 270

Val Pro Glu Glu Ala Ser Gly Glu Ala Ser Glu Ile Pro Val Pro Gln
        275                 280                 285

Gly Thr Glu Leu Ser Pro Ser Arg Pro Gly Gly Gly Ser Met Gln Thr
    290                 295                 300
```

```
Glu Pro Ala Arg Pro Ser Asn Phe Leu Ser Ala Ser Ser Pro Leu Pro
305                 310                 315                 320

Ala Ser Ala Lys Gly Gln Gln Pro Ala Asp Val Thr Gly Thr Ala Leu
                325                 330                 335

Pro Arg Val Gly Pro Val Arg Pro Thr Gly Gln Asp Trp Asn His Thr
            340                 345                 350

Pro Gln Lys Thr Asp His Pro Ser Ala Leu Leu Arg Asp Pro Pro Glu
        355                 360                 365

Pro Gly Ser Pro Arg Ile Ser Ser Leu Arg Pro Gln Gly Leu Ser Asn
    370                 375                 380

Pro Ser Thr Leu Ser Ala Gln Pro Gln Leu Ser Arg Ser His Ser Ser
385                 390                 395                 400

Gly Ser Val Leu Pro Leu Gly Glu Leu Glu Gly Arg Arg Ser Thr Arg
                405                 410                 415

Asp Arg Arg Ser Pro Ala Glu Pro Glu Gly Gly Pro Ala Ser Glu Gly
            420                 425                 430

Ala Ala Arg Pro Leu Pro Arg Phe Asn Ser Val Pro Leu Thr Asp Thr
        435                 440                 445

Gly His Glu Arg Gln Ser Glu Gly Ser
    450                 455


<210> SEQ ID NO 18
<211> LENGTH: 158
<212> TYPE: PRT
<213> ORGANISM: Artificial Sequence
<220> FEATURE:
<223> OTHER INFORMATION: Synthetic peptide

<400> SEQUENCE: 18

Glu Glu Val Ser Glu Tyr Cys Ser His Met Ile Gly Ser Gly His Leu
1               5                   10                  15

Gln Ser Leu Gln Arg Leu Ile Asp Ser Gln Met Glu Thr Ser Cys Gln
            20                  25                  30

Ile Thr Phe Glu Phe Val Asp Gln Glu Gln Leu Lys Asp Pro Val Cys
        35                  40                  45

Tyr Leu Lys Lys Ala Phe Leu Leu Val Gln Asp Ile Met Glu Asp Thr
    50                  55                  60

Met Arg Phe Arg Asp Asn Thr Pro Asn Ala Ile Ala Ile Val Gln Leu
65                  70                  75                  80

Gln Glu Leu Ser Leu Arg Leu Lys Ser Cys Phe Thr Lys Asp Tyr Glu
                85                  90                  95

Glu His Asp Lys Ala Cys Val Arg Thr Phe Tyr Glu Thr Pro Leu Gln
            100                 105                 110

Leu Leu Glu Lys Val Lys Asn Val Phe Asn Glu Thr Lys Asn Leu Leu
        115                 120                 125

Asp Lys Asp Trp Asn Ile Phe Ser Lys Asn Cys Asn Asn Ser Phe Ala
    130                 135                 140

Glu Cys Ser Ser Gln Gly His Glu Arg Gln Ser Glu Gly Ser
145                 150                 155


<210> SEQ ID NO 19
<211> LENGTH: 159
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
```

-continued

```
<222> LOCATION: (25)..(27)
<223> OTHER INFORMATION: Xaa can be any naturally occurring amino acid
<220> FEATURE:
<221> NAME/KEY: misc_feature
<222> LOCATION: (31)..(33)
<223> OTHER INFORMATION: Xaa can be any naturally occurring amino acid

<400> SEQUENCE: 19

Glu Glu Val Ser Glu Tyr Cys Ser His Met Ile Gly Ser Gly His Leu
1               5                   10                  15

Gln Ser Leu Gln Arg Leu Ile Asp Xaa Xaa Xaa Arg Gly Asp Xaa Xaa
            20                  25                  30

Xaa Ile Thr Phe Glu Phe Val Asp Gln Glu Gln Leu Lys Asp Pro Val
        35                  40                  45

Cys Tyr Leu Lys Lys Ala Phe Leu Leu Val Gln Asp Ile Met Glu Asp
    50                  55                  60

Thr Met Arg Phe Arg Asp Asn Thr Pro Asn Ala Ile Ala Ile Val Gln
65                  70                  75                  80

Leu Gln Glu Leu Ser Leu Arg Leu Lys Ser Cys Phe Thr Lys Asp Tyr
                85                  90                  95

Glu Glu His Asp Lys Ala Cys Val Arg Thr Phe Tyr Glu Thr Pro Leu
            100                 105                 110

Gln Leu Leu Glu Lys Val Lys Asn Val Phe Asn Glu Thr Lys Asn Leu
        115                 120                 125

Leu Asp Lys Asp Trp Asn Ile Phe Ser Lys Asn Cys Asn Asn Ser Phe
    130                 135                 140

Ala Glu Cys Ser Ser Gln Gly His Glu Arg Gln Ser Glu Gly Ser
145                 150                 155
```